US009061067B2

(12) United States Patent
Dörwald et al.

(10) Patent No.: US 9,061,067 B2
(45) Date of Patent: Jun. 23, 2015

(54) POLYPEPTIDE PROTRACTING TAGS

(75) Inventors: Florencio Zaragoza Dörwald, Smørum (DK); Christine Bruun Schiødt, Brønshøj (DK); Thomas Kruse Hansen, Herlev (DK); Kjeld Madsen, Værløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 25 days.

(21) Appl. No.: 13/327,378

(22) Filed: Dec. 15, 2011

(65) Prior Publication Data

US 2012/0088716 A1    Apr. 12, 2012

Related U.S. Application Data

(63) Continuation of application No. 11/631,889, filed as application No. PCT/EP2005/052874 on Jun. 21, 2005, now abandoned.

(60) Provisional application No. 60/587,075, filed on Jul. 12, 2004, provisional application No. 60/664,551, filed on Mar. 23, 2005.

(30) Foreign Application Priority Data

Jul. 8, 2004   (DK) .................................. 2004 01083
Mar. 18, 2005  (EP) .................................... 05102167

(51) Int. Cl.
*A61K 31/41*    (2006.01)
*A61K 38/27*    (2006.01)
*C07D 257/04*   (2006.01)
*C07K 1/113*    (2006.01)
*C07K 14/61*    (2006.01)
*A61K 47/48*    (2006.01)
*C07K 1/00*     (2006.01)

(52) U.S. Cl.
CPC .......... *A61K 47/48061* (2013.01); *C07K 1/113* (2013.01); *C07K 1/006* (2013.01); *A61K 38/27* (2013.01); *A61K 31/41* (2013.01); *C07D 257/04* (2013.01); *C07K 14/61* (2013.01); *A61K 47/48023* (2013.01)

(58) Field of Classification Search
None
See application file for complete search history.

(56) References Cited

U.S. PATENT DOCUMENTS

| | | | |
|---|---|---|---|
| 3,869,437 A | 3/1975 | Lindsay et al. | |
| 4,829,053 A | 5/1989 | Raddatz et al. | |
| 5,710,153 A | 1/1998 | Ohmoto et al. | |
| 5,776,927 A * | 7/1998 | Abelman et al. | 514/210.17 |
| 5,854,277 A | 12/1998 | Kluender et al. | |
| 5,883,107 A * | 3/1999 | Levy et al. | 514/305 |
| 5,905,140 A | 5/1999 | Hansen | |
| 6,492,531 B1 | 12/2002 | Woodruff | |
| 8,067,362 B2 * | 11/2011 | Kodra et al. | 514/6.3 |
| 8,541,368 B2 * | 9/2013 | Lau et al. | 514/7.2 |
| 2004/0254119 A1 | 12/2004 | West et al. | |
| 2005/0096466 A1 * | 5/2005 | Schwinden et al. | 540/200 |

FOREIGN PATENT DOCUMENTS

| | | |
|---|---|---|
| DE | 19521653 A1 | 12/1996 |
| EP | 47661 A1 | 3/1982 |
| EP | 624596 A2 | 11/1994 |
| EP | 712861 A2 | 4/2003 |
| JP | 60-004165 A | 1/1985 |
| JP | 9136878 | 5/1997 |
| JP | 2002/522482 A | 7/2002 |
| WO | 92/01476 A1 | 2/1992 |
| WO | 96/15096 A1 | 5/1996 |
| WO | 99/58518 | 11/1999 |
| WO | 00/41548 A2 | 7/2000 |
| WO | 02/058690 A2 | 8/2002 |
| WO | 02/066035 A2 | 8/2002 |
| WO | 03/000180 A2 | 1/2003 |
| WO | 03/013573 | 2/2003 |
| WO | 03/027081 A2 | 4/2003 |
| WO | 03/045371 A1 | 6/2003 |
| WO | 03/061567 A2 | 7/2003 |
| WO | 03/062248 A2 | 7/2003 |
| WO | 03/082861 A2 | 10/2003 |
| WO | 03/099805 A1 | 12/2003 |
| WO | 03/103635 A1 | 12/2003 |
| WO | 2004/050657 A2 | 6/2004 |
| WO | 2004/056347 | 7/2004 |
| WO | 2004/080480 | 9/2004 |
| WO | 2005/027978 A2 | 3/2005 |
| WO | 2005/028516 A2 | 3/2005 |
| WO | 2005/058958 A2 | 6/2005 |

OTHER PUBLICATIONS

Folkes et al., 2002, "Design, Synthesis and In Vitro Evaluation of Potent, Novel, Small Molecule Inhibitors of Plasminogen Activator Inhibitor-1", Bioorganic & Medicinal Chemistry Letters, vol. 12, pp. 1063-1066.
Chou et al., 1997, "A Radioimmunoassay for LY315902, an analog of Glucagon-like Insulinotropic Peptide, and its Application in the Study of Canine Pharmacokinetics", Journal of Pharmaceutical Sciences, vol. 86, Part 7, pp. 768-773.
Knudsen, 2000, "Potent Derivatives of Glucagon-like Peptide-1 with Pharmacokinetic Properties Suitable for Once Daily Administration", Journal Med. Chem., vol. 43, Part 9, pp. 1664-1669.
Zobel et al., 2003, "Phosphate Ester Serum Albumin Affinity Tags Greatly Improve Peptide Half-Life In Vivo", Bioorganic & Medicinal Chemistry Letters, vol. 13, pp. 1513-1515.
Devadas et al., 1992, "Substrate Specificity of *Saccharomyces cerevisiae* Myristoyl-CoA: Protein N-Myristoyltransferase", The Journal of Biological Chemistry, vol. 267, No. 11, pp. 7224-7239.
Chemical Abstracts Service, Columbus Ohio, Database Registry XP000002658736, (1989).
Koehler et al. "Albumin affinity tags increase peptide half-life in vivo" Bioorg. Med. Chem. Lett. vol. 12: 2883-2886 (2002).

* cited by examiner

*Primary Examiner* — Jeffrey E Russel
(74) *Attorney, Agent, or Firm* — Jianjie Hu

(57) ABSTRACT

The invention relates to methods for increasing the plasma half-life of a molecule, such as human growth hormone, comprising covalently linking the molecule to a heterocyclic carboxylic acid bioisostere.

11 Claims, No Drawings

SEQUENCE LISTING

```
<160> NUMBER OF SEQ ID NOS: 43

<210> SEQ ID NO 1
<211> LENGTH: 31
<212> TYPE: PRT
<213> ORGANISM: homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: Gila monster

<400> SEQUENCE: 2

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-3-(2-aminoimidazol-4-yl)propionic
      acid, beta-hydroxy-histidine, homohistidine,
      N-alpha-acetyl-histidine, alpha-fluoromethyl-histidine,
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Lys, Aib, 1-aminocyclopropanecarboxylic acid,
      1-aminocyclobutanecarboxylic acid, 1-aminocyclopentanecarboxylic
      acid, 1-aminocyclohexanecarboxylic acid,
      1-aminocycloheptanecarboxylic
<220> FEATURE:
<221> NAME/KEY: MISC_FEATURE
<222> LOCATION: (10)..(10)
<223> OTHER INFORMATION: Xaa at position 10 is Val or Leu.
<220> FEATURE:
<221> NAME/KEY: MISC_FEATURE
<222> LOCATION: (12)..(12)
<223> OTHER INFORMATION: Xaa at position 12 is Ser, Lys or Arg.
<220> FEATURE:
<221> NAME/KEY: MISC_FEATURE
<222> LOCATION: (13)..(13)
<223> OTHER INFORMATION: Xaa at position 13 is Tyr or Gln.
<220> FEATURE:
<221> NAME/KEY: MISC_FEATURE
<222> LOCATION: (14)..(14)
<223> OTHER INFORMATION: Xaa at position 14 is Leu or Met.
<220> FEATURE:
<221> NAME/KEY: MISC_FEATURE
<222> LOCATION: (16)..(16)
<223> OTHER INFORMATION: Xaa at position 16 is Gly, Glu or Aib.
<220> FEATURE:
<221> NAME/KEY: MISC_FEATURE
<222> LOCATION: (17)..(17)
<223> OTHER INFORMATION: Xaa at position 17 is Gln, Glu, Lys or Arg.
<220> FEATURE:
<221> NAME/KEY: MISC_FEATURE
<222> LOCATION: (19)..(19)
<223> OTHER INFORMATION: Xaa at position 19 is Ala or Val.
<220> FEATURE:
<221> NAME/KEY: MISC_FEATURE
<222> LOCATION: (20)..(20)
<223> OTHER INFORMATION: Xaa at position 20 is Lys, Glu or Arg.
<220> FEATURE:
<221> NAME/KEY: MISC_FEATURE
<222> LOCATION: (21)..(21)
<223> OTHER INFORMATION: Xaa at position 21 is Glu or Leu.
<220> FEATURE:
<221> NAME/KEY: MISC_FEATURE
<222> LOCATION: (24)..(24)
<223> OTHER INFORMATION: Xaa at position 24 is Ala, Glu or Arg.
<220> FEATURE:
<221> NAME/KEY: MISC_FEATURE
<222> LOCATION: (27)..(27)
<223> OTHER INFORMATION: Xaa at position 27 is Val or Lys.
<220> FEATURE:
<221> NAME/KEY: MISC_FEATURE
<222> LOCATION: (28)..(28)
<223> OTHER INFORMATION: Xaa at position 28 is Lys, Glu, Asn or Arg.
<220> FEATURE:
<221> NAME/KEY: MISC_FEATURE
<222> LOCATION: (29)..(29)
```

```
<223> OTHER INFORMATION: Xaa at position 29 is Gly or Aib.
<220> FEATURE:
<221> NAME/KEY: MISC_FEATURE
<222> LOCATION: (30)..(30)
<223> OTHER INFORMATION: Xaa at position 30 is Arg, Gly or Lys.
<220> FEATURE:
<221> NAME/KEY: MISC_FEATURE
<222> LOCATION: (31)..(31)
<223> OTHER INFORMATION: Xaa at position 31 is Gly, Ala, Glu, Pro, Lys,
      amide or is absent.
<220> FEATURE:
<221> NAME/KEY: MISC_FEATURE
<222> LOCATION: (32)..(32)
<223> OTHER INFORMATION: Xaa at position 32 is Lys, Ser, amide or is
      absent.
<220> FEATURE:
<221> NAME/KEY: MISC_FEATURE
<222> LOCATION: (33)..(33)
<223> OTHER INFORMATION: Xaa at position 33 is Ser, Lys, amide or is
      absent.
<220> FEATURE:
<221> NAME/KEY: MISC_FEATURE
<222> LOCATION: (34)..(34)
<223> OTHER INFORMATION: Xaa at position 34 is Gly, amide or is absent.
<220> FEATURE:
<221> NAME/KEY: MISC_FEATURE
<222> LOCATION: (35)..(35)
<223> OTHER INFORMATION: Xaa at position 35 is Ala, amide or is absent.
<220> FEATURE:
<221> NAME/KEY: MISC_FEATURE
<222> LOCATION: (36)..(36)
<223> OTHER INFORMATION: Xaa at position 36 is Pro, amide or is absent.
<220> FEATURE:
<221> NAME/KEY: MISC_FEATURE
<222> LOCATION: (37)..(37)
<223> OTHER INFORMATION: Xaa at position 37 is Pro, amide or is absent.
<220> FEATURE:
<221> NAME/KEY: MISC_FEATURE
<222> LOCATION: (38)..(38)
<223> OTHER INFORMATION: Xaa at position 38 is Pro, amide or is absent.
<220> FEATURE:
<221> NAME/KEY: MISC_FEATURE
<222> LOCATION: (39)..(39)
<223> OTHER INFORMATION: Xaa at position 39 is Ser, amide or is absent.
<220> FEATURE:
<221> NAME/KEY: MISC_FEATURE
<222> LOCATION: (40)..(40)
<223> OTHER INFORMATION: Xaa at position 40 is amide or is absent.

<400> SEQUENCE: 3

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
                20                  25                  30

Xaa Xaa Xaa Xaa Xaa Xaa Xaa Xaa
        35                  40

<210> SEQ ID NO 4
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-3-(2-aminoimidazol-4-yl)propionic
      acid, beta-hydroxy-histidine, homohistidine,
      N-alpha-acetyl-histidine, alpha-fluoromethyl-histidine,
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Lys, Aib, 1-aminocyclopropanecarboxylic acid,
```

```
        1-aminocyclobutanecarboxylic acid,
        1-aminocyclopentanecarboxylic acid,
        1-aminocyclohexanecarboxylic acid,
        1-aminocycloheptanecarboxylic
<220> FEATURE:
<221> NAME/KEY: MISC_FEATURE
<222> LOCATION: (12)..(12)
<223> OTHER INFORMATION: Xaa at position 12 is Ser, Lys or Arg.
<220> FEATURE:
<221> NAME/KEY: MISC_FEATURE
<222> LOCATION: (16)..(16)
<223> OTHER INFORMATION: Xaa at position 16 is Gly, Glu or Aib.
<220> FEATURE:
<221> NAME/KEY: MISC_FEATURE
<222> LOCATION: (17)..(17)
<223> OTHER INFORMATION: Xaa at position 17 is Gln, Glu, Lys or Arg.
<220> FEATURE:
<221> NAME/KEY: MISC_FEATURE
<222> LOCATION: (20)..(20)
<223> OTHER INFORMATION: Xaa at position 20 is Lys, Glu or Arg.
<220> FEATURE:
<221> NAME/KEY: MISC_FEATURE
<222> LOCATION: (24)..(24)
<223> OTHER INFORMATION: Xaa at position 24 is Ala, Glu or Arg.
<220> FEATURE:
<221> NAME/KEY: MISC_FEATURE
<222> LOCATION: (28)..(28)
<223> OTHER INFORMATION: Xaa at position 28 is Lys, Glu or Arg.
<220> FEATURE:
<221> NAME/KEY: MISC_FEATURE
<222> LOCATION: (29)..(29)
<223> OTHER INFORMATION: Xaa at position 29 is Gly or Aib.
<220> FEATURE:
<221> NAME/KEY: MISC_FEATURE
<222> LOCATION: (30)..(30)
<223> OTHER INFORMATION: Xaa at position 30 is Arg or Lys.
<220> FEATURE:
<221> NAME/KEY: MISC_FEATURE
<222> LOCATION: (31)..(31)
<223> OTHER INFORMATION: Xaa at position 31 is Gly, Ala, Glu or Lys.
<220> FEATURE:
<221> NAME/KEY: MISC_FEATURE
<222> LOCATION: (32)..(32)
<223> OTHER INFORMATION: Xaa at position 32 is Lys, amide or is absent.

<400> SEQUENCE: 4

Xaa Xaa Glu Gly Thr Phe Thr Ser Asp Val Ser Xaa Tyr Leu Glu Xaa
1               5                   10                  15

Xaa Ala Ala Xaa Glu Phe Ile Xaa Trp Leu Val Xaa Xaa Xaa Xaa Xaa
            20                  25                  30

<210> SEQ ID NO 5
<211> LENGTH: 44
<212> TYPE: PRT
<213> ORGANISM: Artificial Sequence
<220> FEATURE:
<223> OTHER INFORMATION: Synthetic

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 6
<211> LENGTH: 31
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 6

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Xaa Arg Lys
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Synthetic

<400> SEQUENCE: 8

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Synthetic

<400> SEQUENCE: 9

His Gly Glu Gly Thr Phe Thr Ser Asp Val Ser Arg Tyr Leu Glu Glu
1               5                   10                  15

Glu Ala Ala Arg Glu Phe Ile Glu Trp Leu Val Arg Gly Arg Gly Lys
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(16)
```

```
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 10

Ala Glu Gly Thr Phe Thr Ser Asp Val Ser Ser Tyr Leu Glu Gly Xaa
1               5                   10                  15

Ala Ala Arg Glu Phe Ile Ala Trp Leu Val Arg Gly Xaa Lys
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 11

His Xaa Glu Gly Thr Phe Thr Ser Asp Val Ser Ser Tyr Leu Glu Xaa
1               5                   10                  15

Gln Ala Ala Arg Glu Phe Ile Ala Trp Leu Val Arg Xaa Arg Lys
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)

<400> SEQUENCE: 12

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Lys
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Synthetic

<400> SEQUENCE: 13

Ala Glu Gly Thr Phe Thr Ser Asp Val Ser Ser Tyr Leu Glu Gly Gln
1               5                   10                  15
```

```
Ala Ala Lys Glu Phe Ile Ala Trp Leu Val Arg Gly Arg Gly
            20                  25                  30

<210> SEQ ID NO 14
<211> LENGTH: 28
<212> TYPE: PRT
<213> ORGANISM: Artificial Sequence
<220> FEATURE:
<223> OTHER INFORMATION: Synthetic

<400> SEQUENCE: 14

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Lys
            20                  25

<210> SEQ ID NO 15
<211> LENGTH: 39
<212> TYPE: PRT
<213> ORGANISM: Artificial Sequence
<220> FEATURE:
<223> OTHER INFORMATION: Synthetic

<400> SEQUENCE: 15

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 16
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)

<400> SEQUENCE: 16

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 17
<211> LENGTH: 39
<212> TYPE: PRT
<213> ORGANISM: Artificial Sequence
<220> FEATURE:
<223> OTHER INFORMATION: Synthetic

<400> SEQUENCE: 17

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Lys
            20                  25                  30

Ser Gly Ala Pro Pro Pro Ser
        35

<210> SEQ ID NO 18
```

```
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)

<400> SEQUENCE: 18

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Synthetic

<400> SEQUENCE: 19

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Synthetic

<400> SEQUENCE: 20

His Ala Glu Gly Thr Phe Thr Lys Asp Val Ser Ser Tyr Leu Glu Gly
1               5                   10                  15

Gln Ala Ala Arg Glu Phe Ile Ala Trp Leu Val Arg Gly Arg Gly
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Synthetic

<400> SEQUENCE: 21

His Ala Glu Gly Thr Phe Thr Ser Asp Val Ser Lys Tyr Leu Glu Gly
1               5                   10                  15

Gln Ala Ala Arg Glu Phe Ile Ala Trp Leu Val Arg Gly Arg Gly
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Synthetic

<400> SEQUENCE: 22

His Gly Glu Gly Thr Phe Thr Ser Asp Val Ser Lys Tyr Leu Glu Gly
1               5                   10                  15
```

Gln Ala Ala Arg Glu Phe Ile Ala Trp Leu Val Arg Gly Arg Gly
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)

<400> SEQUENCE: 23

His Xaa Glu Gly Thr Phe Thr Ser Asp Val Ser Lys Tyr Leu Glu Gly
1               5                   10                  15

Gln Ala Ala Arg Glu Phe Ile Ala Trp Leu Val Arg Gly Arg Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic

<400> SEQUENCE: 24

Ala Glu Gly Thr Phe Thr Ser Asp Val Ser Lys Tyr Leu Glu Gly Gln
1               5                   10                  15

Ala Ala Arg Glu Phe Ile Ala Trp Leu Val Arg Gly Arg Gly
            20                  25                  30

<210> SEQ ID NO 25
<211> LENGTH: 27
<212> TYPE: PRT
<213> ORGANISM: Artificial Sequence
<220> FEATURE:
<223> OTHER INFORMATION: Synthetic

<400> SEQUENCE: 25

His Ala Glu Gly Thr Phe Thr Ser Asp Val Ser Lys Tyr Leu Glu Gly
1               5                   10                  15

Gln Ala Ala Arg Glu Phe Ile Ala Trp Leu Val
            20                  25

<210> SEQ ID NO 26
<211> LENGTH: 32
<212> TYPE: PRT
<213> ORGANISM: Artificial Sequence
<220> FEATURE:
<223> OTHER INFORMATION: Synthetic

<400> SEQUENCE: 26

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic

<400> SEQUENCE: 27

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 28

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Xaa Arg Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 29

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Gly
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)

<400> SEQUENCE: 30

His Xaa Glu Gly Thr Phe Thr Ser Asp Val Ser Ser Tyr Leu Glu Xaa

```
1               5                   10                  15
Gln Ala Ala Lys Glu Phe Ile Ala Trp Leu Val Lys Gly Arg Gly
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 31

His Xaa Glu Gly Thr Phe Thr Ser Asp Val Ser Ser Tyr Leu Glu Xaa
1               5                   10                  15
Gln Ala Ala Arg Glu Phe Ile Ala Trp Leu Val Arg Xaa Arg Gly Lys
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 32

His Xaa Glu Gly Thr Phe Thr Ser Asp Val Ser Ser Tyr Leu Glu Gly
1               5                   10                  15
Gln Ala Ala Arg Glu Phe Ile Ala Trp Leu Val Arg Xaa Arg Gly Lys
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)

<400> SEQUENCE: 33

His Xaa Glu Gly Thr Phe Thr Ser Asp Val Ser Ser Tyr Leu Glu Xaa
1               5                   10                  15
Gln Ala Ala Arg Glu Phe Ile Ala Trp Leu Val Arg Gly Arg Gly Lys
```

<210> SEQ ID NO 34
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 34

His Xaa Glu Gly Thr Phe Thr Ser Asp Val Ser Ser Tyr Leu Glu Xaa
1               5                   10                  15

Gln Ala Ala Arg Glu Phe Ile Ala Trp Leu Val Lys Xaa Arg Gly Lys
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 35

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Lys Xaa Arg Gly Lys
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)

<400> SEQUENCE: 36

His Xaa Glu Gly Thr Phe Thr Ser Asp Val Ser Ser Tyr Leu Glu Xaa
1               5                   10                  15

Gln Ala Ala Arg Glu Phe Ile Ala Trp Leu Val Lys Gly Arg Gly Lys
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 37

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Arg Xaa Arg Gly Lys
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 38

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Xaa Arg Gly Lys
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)

<400> SEQUENCE: 39

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Arg Gly Arg Gly Lys
            20                  25                  30

<210> SEQ ID NO 40
<211> LENGTH: 32
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 40

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Lys Xaa Arg Ala Lys
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 41

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg Ala Lys
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (16)..(16)
<223> OTHER INFORMATION: Xaa = Aib (2-Aminoisobutyric acid)

<400> SEQUENCE: 42

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Lys Gly Arg Ala Lys
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (2)..(2)
<223> OTHER INFORMATION: Xaa = Aib (2-Aminoisobutyric acid)
<220> FEATURE:
<221> NAME/KEY: MISC_FEATURE
<222> LOCATION: (29)..(29)
<223> OTHER INFORMATION: Xaa = Aib (2-Aminoisobutyric acid)

<400> SEQUENCE: 43

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Lys
            20                  25                  30
```

POLYPEPTIDE PROTRACTING TAGS

CROSS-REFERENCE TO RELATED APPLICATIONS

This application is a continuation of U.S. application Ser. No. 11/631,889, filed Oct. 31, 2008, which is a 35 U.S.C. §371 national stage of PCT/EP2005/052874, filed Jun. 21, 2005, which claimed priority of Danish Patent Application PA 2004 01083, filed Jul. 8, 2004, U.S. Provisional Patent Application 60/587,075, filed Jul. 12, 2004, European Patent Application 05102167.3 filed Mar. 18, 2005, and U.S. Provisional Patent Application 60/664,551 filed Mar. 23, 2005.

FIELD OF THE INVENTION

The present invention relates to compounds comprising a heterocyclic carboxylic acid bioisostere, methods for preparing the compounds and the medical applications of such compounds.

BACKGROUND OF THE INVENTION

It is often desirable to maintain well-defined concentrations of a given compound in the blood stream for a long time. This would for instance be the case when an immunogen is administered and a strong immune response is desired, or when a therapeutic target has to be exposed continuously to a therapeutic agent for a long time. Currently there are no universally applicable strategies to enhance the plasma half-life of any type of compound. The number of known endogenous polypeptides with interesting biological activities is growing rapidly, also as a result of the ongoing exploration of the human genome. Due to their biological activities, many of these polypeptides could in principle be used as therapeutic agents. Endogenous peptides are, however, not always suitable as drug candidates because these peptides often have half-lives of few minutes due to rapid degradation by peptidases and/or due to renal filtration and excretion in the urine. The half-life of polypeptides in human plasma varies strongly (from a few minutes to more than one week). Similarly, the half-life of small molecule drugs is also highly variable. The reason for this strong variability of plasma half-lives of peptides, proteins, or other compounds is, however, not well understood.

Serum albumin has a half-life of more than one week, and one approach to increasing the plasma half-life of peptides has been to derivatised the peptides with a chemical entity that binds to serum albumin.

Knudsen et al. (*J. Med. Chem.* 2000, 43, 1664-1669) have shown that acylated GLP-1 peptides exhibit high receptor potency and a tenfold increase of plasma half-life in pigs. Zobel et al. (*Bioorg. Med. Chem. Lett.* 2003, 13, 1513-1515) have shown that the plasma half-life of an anticoagulant peptide in rabbits increased by 10-50 fold on derivatisation of the amino terminus with phosphate ester based small molecules binding to serum albumin.

SUMMARY OF THE INVENTION

According to the present invention there is provided a method for increasing the plasma half-life of a molecule, comprising covalently linking this molecule to a heterocyclic carboxylic acid bioisostere.

The present invention also relates to a method for increasing the plasma half-life of a molecule, comprising covalently linking this molecule to a 1H-tetrazole.

According to the present invention there is also provided a method for increasing the plasma half-life of a molecule, comprising converting said molecule into a compound of the general formula (I):

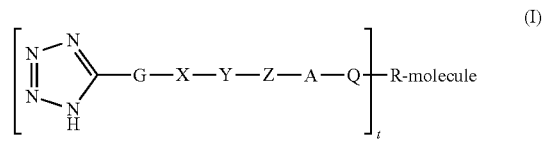

wherein
G, X, and Y independently represent
 a bond, —S—, —O—, —NH—, —$(CH_2)_{1-10}$—, or
 arylene, optionally substituted with one or more alkyl, amino, cycloalkyl, aryl, heteroaryl, halogen, nitro, lower alkoxy, hydroxy, MeCONH—, alkanoyl, or cyano, or
 heteroarylene, optionally substituted with one or more alkyl, amino, cycloalkyl, aryl, heteroaryl, halogen, nitro, lower alkoxy, hydroxy, MeCONH—, alkanoyl, or cyano, and
Z represents a bond or
 —$(CH_2)_n$—, —O—$(CH_2)_n$—, —S—$(CH_2)_n$—, —$(OCH_2CH_2)_n$—, —$(CF_2)_n$—, —O—$CH_2$—$(CF_2)_n$—, —S—$CH_2$—$(CF_2)_n$—, wherein n is 1-40, and
A represents
 —C(=O)—, —O—C(=O)—, —NH—C(=O)—, —C(C=O)NH—S(=O)$_2$—, —S(=O)$_2$NH—C(=O)—, —$(CH_2)_{1-5}$—, —O—$(CH_2)_{1-5}$—, or —O—$(CH_2)_{1-5}$—C(=O)—, and
Q represents a bond or
 —[NH—$(CH_2CH_2O)_m$—$(CH_2)_p$-E-C(=O)]$_q$—, or
 —O—$(CH_2CH_2O)_m$—$(CH_2)_p$-E-C(=O)—, or
 —S—$(CH_2CH_2O)_m$—$(CH_2)_p$-E-C(=O)—, wherein E is a bond, O, S, or NH, and m, p, and q independently are 1-40, and
R represents a bond or a polyradical, such as [—NH(CH$_2$)$_4$CH(NH—)—C(=O)—]$_{1-5}$, and
t is 1-40, and
the term 'molecule' refers to a compound comprising an amino group or a mercapto group, to which the group A or Q may be covalently The present invention thus provides compounds of the general formula (I):

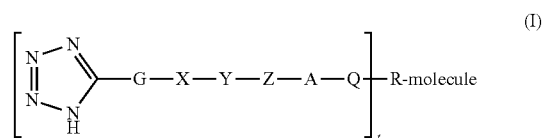

wherein
G, X, and Y independently represent
 a bond, —S—, —O—, —NH—, —$(CH_2)_{1-10}$—, or
 arylene, optionally substituted with one or more alkyl, amino, cycloalkyl, aryl, heteroaryl, halogen, nitro, lower alkoxy, hydroxy, MeCONH—, alkanoyl, or cyano, or
 heteroarylene, optionally substituted with one or more alkyl, amino, cycloalkyl, aryl, heteroaryl, halogen, nitro, lower alkoxy, hydroxy, MeCONH—, alkanoyl, or cyano, and Z represents a bond or
—(CH$_2$)$_n$—, —O—(CH$_2$)$_n$—, —S—(CH$_2$)$_n$—, —(OCH$_2$CH$_2$)$_n$—, —(CF$_2$)$_n$—, —O—CH$_2$—(CF$_2$)$_n$—, —S—CH$_2$—(CF$_2$)$_n$—, wherein n is 1-40, and A represents
—C(=O)—, —O—C(=O)—, —NH—C(=O)—, —C(=O)NH—S(=O)$_2$—, —S(=O)$_2$NH—C(=O)—, —(CH$_2$)$_{1-5}$—, —O—(CH$_2$)$_{1-5}$—, or —O—(CH$_2$)$_{1-5}$—C(=O)—, and Q represents a bond or
—[NH—(CH$_2$CH$_2$O)$_m$—(CH$_2$)$_p$-E-C(=O)]$_q$—, or
—O—(CH$_2$CH$_2$O)$_m$—(CH$_2$)$_p$-E-C(=O)—, or
—S—(CH$_2$CH$_2$O)$_m$—(CH$_2$)$_p$-E-C(=O)—, wherein E is a bond, O, S, or NH, and m, p, and q independently are 1-40, and R represents a bond or a polyradical, such as [—NH(CH$_2$)$_4$CH(NH—)—C(=O)—]$_{1-5}$, and t is 1-40, and the term 'molecule' refers to a compound comprising an amino group or a mercapto group, to which the group A or Q may be covalently linked.

The present invention also provides a compound according to formula (I), wherein G, X and Y are all a bond.

The present invention also provides a compound according to formula (I), wherein G, X and Y are all selected from —(CH$_2$)$_{1-10}$—.

The present invention also provides a compound according to formula (I), wherein t is 1.

DEFINITIONS

In the present specification, the following terms have the indicated meaning:

The term "polyradical" means a molecule or molecular moiety with more than one unshared electron. A polyradical according to this definition may be used to covalently link two or more (mono-)radicals together.

The term "small molecule drug" means a therapeutic agent with a molecular weight <1500 g/mol.

The term "therapeutic agent" means a peptide, protein, small molecule drug, or any other type of compound, able to elicit a biological response.

The term "plasma half-life" means the time required for the concentration of a given compound present in the plasma of a living mammal, such as a human, to decrease to one half of its original concentration.

The term "analog" refers to a polypeptide in which less than 30% of the amino acids of the original polypeptide have been removed or replaced by other amino acids (including stereoisomeric, unnatural or chemically modified amino acids) or have been chemically modified, for instance by acylation or alkylation of the side chain. The term "analog" also refers to polypeptides in which the N-terminal amino group has been removed, alkylated with lower alkyl, or acylated with lower alkanoic, arylalkanoic, heteroarylalkanoic, or benzoic acids. The term "analog" also includes polypeptides in which the C-terminal carboxyl group has been removed or converted to an amide by condensation with ammonia, lower alkyl amines, lower dialkyl amines, aziridine, azetidine, pyrrolidine, piperidine, or azepine. The term "analog" also includes polypeptides in which the disulfide functionalities between two or more cystein groups have been reduced or the connectivity between two or more cystein groups has been modified.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. An example of a derivative of GLP-1(7-37) is Arg$^{34}$Lys$^{26}$(N$^\epsilon$-(γ-Glu(N$^\alpha$-hexadecanoyl)))-GLP-1(7-37) (Derivative of SEQ ID NO: 7).

The term "unnatural amino acid" refers to any compound comprising at least one primary or secondary amino group and at least one carboxyl group, without being L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, proline, L-serine, L-threonine, L-tryptophan, L-tyrosine, or L-valine.

The term "GLP-1(7-37)" refers to a peptide with the amino acid sequence

```
                                  (SEQ ID No. 1)
HAEGTFTSDVSSYLEGQAAKEFIAWLVKGRG.
```

The term "GLP-1 peptide" as used herein means GLP-1(7-37), a GLP-1 analog, a GLP-1 derivative or a derivative of a GLP-1 analog. In one embodiment the GLP-1 peptide is an insulinotropic agent.

The term "exendin-4(1-39)" refers to a peptide with the amino acid sequence

```
                                  (SEQ ID No. 2)
HGEGTFTSDLSKQMEEEAVRLFIEWLKNGGPSSGAPPPS.
```

The term "insulinotropic agent" as used herein means a compound which is an agonist of the human GLP-1 receptor, i.e. a compound which stimulates the formation of cAMP in a suitable medium containing the human GLP-1 receptor. The potency of an insulinotropic agent is determined by calculating the EC$_{50}$ value from the dose-response curve as described below.

Baby hamster kidney (BHK) cells expressing the cloned human GLP-1 receptor (BHK-467-12A) were grown in DMEM media with the addition of 100 IU/mL penicillin, 100 μL/mL streptomycin, 10% fetal calf serum and 1 mg/mL Geneticin G-418 (Life Technologies). Plasma membranes were prepared by homogenisation in buffer (10 mM Tris-HCl, 30 mM NaCl and 1 mM dithiothreitol, pH 7.4, containing, in addition, 5 mg/L leupeptin (Sigma, St. Louis, Mo., USA), 5 mg/L pepstatin (Sigma), 100 mg/L bacitracin (Sigma), and 16 mg/L aprotinin (Calbiochem-Novabiochem, La Jolla, Calif.). The homogenate was centrifuged on top of a layer of 41 w/v % sucrose. The white band between the two layers was diluted in buffer and centrifuged. Plasma membranes were stored at −80° C. until used.

The functional receptor assay was carried out by measuring cAMP as a response to stimulation by the insulinotropic agent. Incubation were carried out in 96-well microtiter plates in a total volume of 140 μL and with the following final concentrations: 50 mM Tris-HCl, 1 mM EGTA, 1.5 mM MgSO$_4$, 1.7 mM ATP, 20 mM GTP, 2 mM 3-isobutyl-1-methylxanthine (IBMX), 0.01% Tween-20, pH 7.4. Compounds to be tested for agonist activity were dissolved and diluted in buffer. GTP was freshly prepared for each experiment: 2.5 μg of membrane was added to each well and the mixture was incubated for 90 min at room temperature in the dark with shaking. The reaction was stopped by the addition of 25 μL of 0.5 M HCl. Formed cAMP was measured by a scintillation proximity assay (RPA 542, Amersham, UK).

Dose-response curves were plotted for the individual compounds and EC$_{50}$ values calculated using GraphPad Prism software.

The term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV.

Resistance of a peptide to degradation by dipeptidyl aminopeptidase IV is determined by the following degradation assay:

Aliquots of the peptide (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

The term "factor VII" refers to the human factor VII of the blood clotting cascade.

The term "bioisostere" refers to a molecular fragment capable of mimicking the biological properties of another molecular fragment. Typical bioisosteres of carboxylic acids include tetrazoles, phenols, N-acylsulfonamides, or other compounds with an acidic NH- or OH-group.

The term "halogen" means F, Cl, Br or I.

The term "alkyl" as used herein is intended to mean straight, branched, or cyclic $C_1$-$C_{10}$ alkyl.

The term "lower alkyl" refers to $C_1$-$C_6$ alkyl.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "arylene" as used herein is intended to include arene-derived diradicals such as 1,2-phenylene, 1,3-phenylene, 1,4-phenylene, 1,2-naphthylene, 1,4-naphthylene, 4,4'-biphenylene, 4,4''-terphenylene, 4,4'''-quaterphenylene, and the like.

The term "heteroarylene" as used herein is intended to include heteroarene-derived diradicals, such as 1,2,4-pyrazol-2,5-diyl, imidazol-1,2-diyl, thiazol-2,4-diyl, and the like, as well as combinations of arylene with heteroarylene diradicals, such as (4-phenylimidazole)-4,1'-diyl, (3,5-diphenyl-1,2,4-oxadiazole)-4,4''-diyl, and the like.

The term "aryloxy" as used herein refers to the radical —O-aryl where aryl is as defined above. Non-limiting examples are phenoxy, naphthoxy, anthracenyloxy, phenanthrenyloxy, fluorenyloxy, indenyloxy and the like.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indanyl, indolinyl, oxazolidinyl, oxazolinyl, oxazepinyl and the like.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

DETAILED DESCRIPTION OF THE INVENTION

In one aspect the present invention provides a method for increasing the plasma half-life of a molecule, comprising covalently linking this molecule to a heterocyclic carboxylic acid bioisostere.

In another aspect the present invention provides a method for increasing the plasma half-life of a molecule, comprising covalently linking this molecule to a 1H-tetrazole.
In In another aspect the present invention provides a method for increasing the plasma half-life of a molecule, comprising converting said molecule into a compound of the general formula (I):

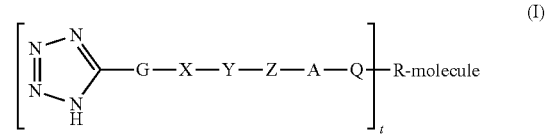

wherein
G, X, and Y independently represent
   a bond, —S—, —O—, —NH—, —(CH$_2$)$_{1-10}$-, or
   arylene, optionally substituted with one or more alkyl, amino, cycloalkyl, aryl, heteroaryl, halogen, nitro, lower alkoxy, hydroxy, MeCONH—, alkanoyl, or cyano, or
   heteroarylene, optionally substituted with one or more alkyl, amino, cycloalkyl, aryl, heteroaryl, halogen, nitro, lower alkoxy, hydroxy, MeCONH—, alkanoyl, or cyano, and Z represents a bond or
—(CH$_2$)$_n$—, —O—(CH$_2$)$_n$—, —S—(CH$_2$)$_n$—, —(OCH$_2$CH$_2$)$_n$—, —(CF$_2$)$_n$—, —O—CH$_2$—(CF$_2$)$_n$—, —S—CH$_2$—(CF$_2$)$_n$—, wherein n is 1-40, and A represents
—C(=O)—, —O—C(=O)—, —NH—C(=O)—, —C(=O)NH—S(=O)$_2$—, —S(=O)$_2$NH—C(=O)—, —(CH$_2$)$_{1-5}$—, —O—(CH$_2$)$_{1-5}$—, or —O—(CH$_2$)$_{1-5}$—C(=O)—, and Q represents a bond or
[NH—(CH$_2$CH$_2$O)$_m$—(CH$_2$)$_p$-E-C(=O)]$_q$, or —O—(CH$_2$CH$_2$O)$_m$—(CH$_2$)$_p$-E-C(=O)—, or S—(CH$_2$CH$_2$O)$_m$—(CH$_2$)$_p$-E-C(=O)—, wherein E is a bond, O, S, or NH, and m, p, and q independently are 1-40, and R represents a bond or a polyradical, such as [—NH(CH$_2$)$_4$CH(NH—)—C(=O)—]$_{1-5}$, and t is 1-40, and the term 'molecule' refers to a compound comprising an amino group or a mercapto group, to which the group A or Q may be covalently linked.

Tetrazoles are slightly more lipophilic than carboxylic acids, but are resistant to many of the metabolic degradation pathways which befall carboxylic acids. Because tetrazoles cannot act as acylating reagents no protective group is required when acylating a protein with an ω-(tetrazol-5-yl) carboxylic acid.

We have found that the derivatization of polypeptides with tetrazole-containing molecular entities is readily performed, and that, surprisingly, the resulting protein-tetrazole conjugates show highly improved biological and pharmacological properties.

As illustrated by the examples below, between the tetrazole and the molecule of which a prolonged half-life in plasma is required there may be an optional spacer, i.e. a divalent or polyvalent molecular fragment able to covalently connect one or several tetrazoles to the molecule. This divalent or polyvalent molecular fragment may also have an influence on the biological properties of the conjugate compound-tetrazole(s), and structural modifications of this spacer may be used to adjust and improve the properties of the conjugate. This spacer may be a combination of one or several different structural elements selected from but not limited to alkylene chains, partially or fully fluorinated alkylene chains, arylenes, heteroarylenes, oligo(ethylene glycol), amide bonds, lysine, short peptides, short oligoamides, and other, similar fragments.

For connecting the tetrazole-bearing spacer to a compound of interest, such as a therapeutically relevant protein or peptide, various different strategies may be envisioned. Many polypeptides contain amino groups (e.g. the N-terminal amino group or lysine-side-chain amino groups), which can be acylated by a suitable acylating reagent, such as a carboxylic acid in the presence of a coupling reagent, a carboxylic acid O-hydroxysuccinimidyl ester, hydroxybenzotriazole esters, carboxylic acid anhydrides, carboxylic acid halides, carboxylic acid azides, nitrophenyl esters, mixed carboxylic carbonic anhydrides, mixed carboxylic sulfonic anhydrides, imidazolides, and the like. Alternatively, amino-group bearing polypeptides may be derivatized by conversion into a carbamate by treatment with an alkyl haloformiate, an O-succinimidylcarbonate, an alkyl azidoformiate, or a related reagent. Alternatively, amino-group bearing polypeptides may be derivatized by conversion into a urea by treatment with an isocyanate, a carbamoyl halide, a nitrophenyl carbamate, or a related reagent. Alternatively, amino-group bearing polypeptides may be derivatized by conversion into a sulfonamide by treatment with a sulfonyl halide or sulfonyl imidazolide.

All these derivatization reactions can be conducted without the need of any protective group for the tetrazole ring, and are therefore particularly well suited for the derivatization of sensitive polypeptides. Non-limiting, illustrative derivatization procedures of an amino-group-bearing molecule with specific tetrazole derivatives are sketched below:

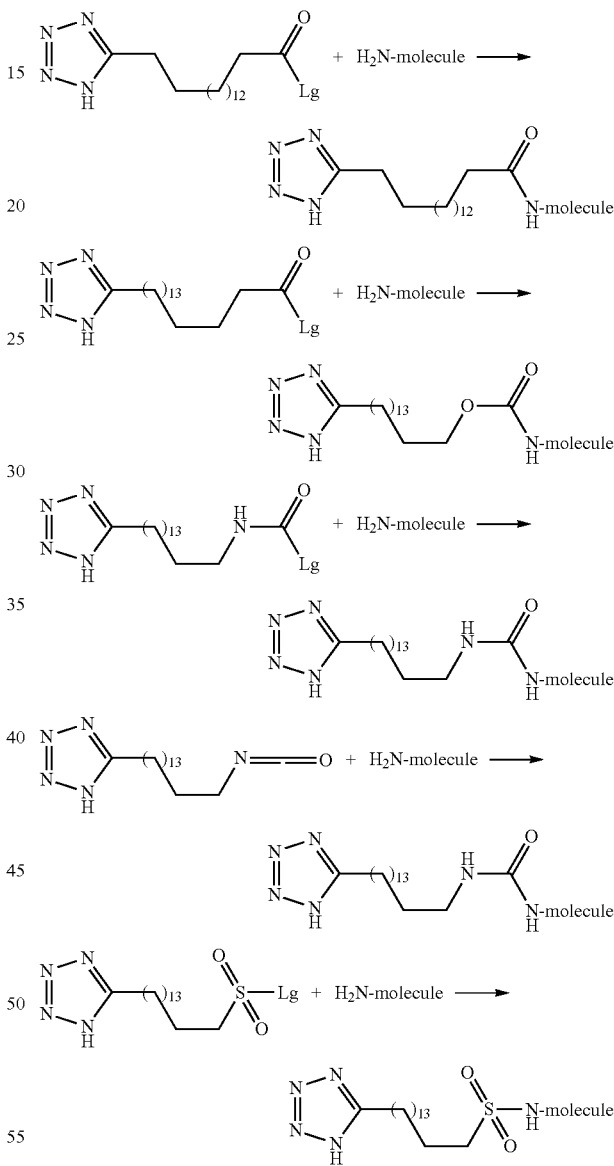

Lg=Cl, F, Br, I, N$_3$, CN, OPh,

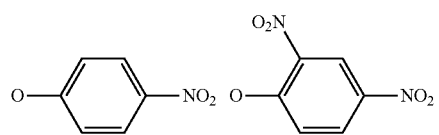

-continued

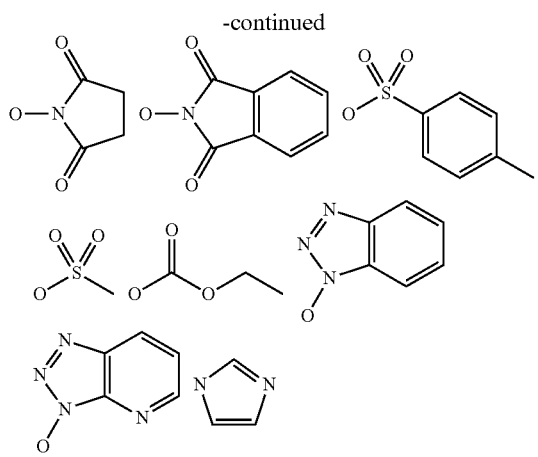

Many polypeptides contain thiol groups, which can be alkylated by treatment with a suitable alkylating reagent, such as an alkyl halide, an alkyl sulfonate, an N-alkylmaleimide, an acrylamide, or a related alkylating reagent, to covalently bind the tetrazole-bearing fragment to the polypeptide. Alternatively, thiol groups may also be arylated by treatment with a suitable arylating reagent, such as an aryl halide, an aryl iodonium salt, an aryldiazonium salt or a similar reagent.

Polypeptides with N-terminal serine or a related functional group (a 1,2-diol, a 2-aminoethanol) can be oxidized by treatment with periodate to an aldehyde. This aldehyde reacts with O-alkylhydroxylamines to yield oximes, and may therefore be used to attach an O-alkylhydroxylamine-containing tetrazole to the polypeptide. The aldehyde formed by oxidation of N-terminal serine also reacts with 2-aminoethylthiols (HS—C—C—NH) to yield thiazolidines, or with hydrazines to yield hydrazones, and these reactions may also be used for the attachment of a tetrazole-bearing fragment to a polypeptide. Aldehydes also react with C,H-acidic compounds such as 1,3-diketones, 3-oxobutyramides, malonodinitriles, barbituric acid derivatives, malonic acid derivatives, and the like to yield alcohols (aldol addition) or alkenes (Knoevenagel condensation). These reactions may also be used to attach tetrazoles to polypeptides.

Enzymes enable the selective derivatization of polypeptides. Thus, carboxypeptidases can be used to form amides from amines and the C-terminal carboxylic acid group of a polypeptide. Transglutaminases may be used to form new amides from amines and the side chain of glutamine. If these enzymatic reactions are performed with a tetrazole-bearing amine, compounds as claimed in this invention will result. Alternatively, these enzymatic reactions may also be conducted with an amine which contains a functional group which enables a selective covalent attachment of a tetrazole-bearing fragment in a second operation. Such functional groups may be aldehydes, ketones, hydroxylamines, alkoxylamines, hydrazines, thiols, azides, 2-aminoethylthiols, 3-aminopropylthiols, 2-hydroxyethylthiols, 3-hydroxypropylthiols, alkynes, alkenes, nitriles, C,H-acidic compounds, or other functional groups which enable the selective covalent attachment of a tetrazole-bearing fragment. Treatment of an amine containing one or several of these functional groups will yield a polypeptide, which can be selectively derivatized.

A methodology for the production of proteins containing unnatural amino acids by fermentation has recently been described (for instance L. Alfonta et al., *J. Am. Chem. Soc.* 2003, 125, 14662-14663; Z. Zhang et al., *Biochemistry*, 2003, 42, 6735-6746). This methodology may also be used to prepare proteins with tetrazole-containing amino acids directly or proteins with an unnatural amino acid which enables facile chemical derivatization. These could, for instance, be amino acids containing a formyl group, a keto group, an azido group, a mercapto group, an alkoxylamino group, a hydrazino group, an alkyne, an alkene, an aryl iodide, or an aryl bromide. The resulting protein, containing this unnatural amino acid, may then be converted into a tetrazole-containing protein by covalent binding of a suitable tetrazole derivative to the side chain of the unnatural amino acid.

Polypeptides may contain one or several tyrosines. These may be selectively derivatized by azocoupling with an aryldiazonium salt. This technique may also be used to prepare compound according to the present invention, by treating said tyrosine-containing polypeptide with a tetrazole-containing aryldiazonium salt.

In another aspect the present invention provides a compound of the general formula (I):

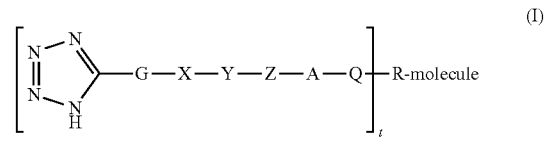

wherein
G, X, and Y independently represent
  a bond, —S—, —O—, —NH—, —(CH$_2$)$_{1-10}$-, or
  arylene, optionally substituted with one or more alkyl, amino, cycloalkyl, aryl, heteroaryl, halogen, nitro, lower alkoxy, hydroxy, MeCONH—, alkanoyl, or cyano, or
  heteroarylene, optionally substituted with one or more alkyl, amino, cycloalkyl, aryl, heteroaryl, halogen, nitro, lower alkoxy, hydroxy, MeCONH—, alkanoyl, or cyano, and
Z represents a bond or
  —(CH$_2$)$_n$—, —O—(CH$_2$)$_n$—, —S—(CH$_2$)$_n$—, —(OCH$_2$CH$_2$)$_n$—, —(CF$_2$)$_n$—, —O—CH$_2$—(CF$_2$)$_n$—, —S—CH$_2$—(CF$_2$)$_n$—, wherein n is 1-40, and
A represents
  —C(=O)—, —O—C(=O)—, —NH—C(=O)—, —C(C=O)NH—S(=O)$_2$—, —S(=O)$_2$NH—C(=O)—, —(CH$_2$)$_{1-5}$—, —O—(CH$_2$)$_{1-5}$—, or —O—(CH$_2$)$_{1-5}$—C(=O)—, and
Q represents a bond or
  —[NH—(CH$_2$CH$_2$O)$_m$—(CH$_2$)$_p$-E-C(=O)]$_q$—, or
  —O—(CH$_2$CH$_2$O)$_m$—(CH$_2$)$_p$-E-C(=O)—, or
  —S—(CH$_2$CH$_2$O)$_m$—(CH$_2$)$_p$-E-C(=O)—, wherein E is a bond, O, S, or NH, and m, p, and q independently are 1-40, and
R represents a bond or a polyradical, such as [—NH(CH$_2$)$_4$CH(NH—)—C(=O)—]$_{1-5}$, and
t is 1-40, and
the term 'molecule' refers to a compound comprising an amino group or a mercapto group, to which the group A or Q may be covalently linked.

In one embodiment the invention provides a compound according to formula (I), wherein G, X and Y are all a bond.

In another embodiment the invention provides a compound according to formula (I), wherein G, X and Y are all selected from —(CH$_2$)$_{1-10}$—.

In another embodiment the invention provides a compound according to formula (I), wherein t is 1.

In another embodiment the invention provides a compound according to formula (I), wherein

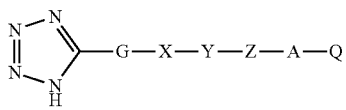

is 16-(5-tetrazolyl)hexadecanoyl,
4-[N-(16-{5-tetrazolyl}hexadecanoyl)sulfamoyl]butyryl,
2-(2-(2-(16-(tetrazol-5-yl)(hexadecanoylamino)ethoxy)ethoxy)acetyl) or
16-(1H-tetrazol-5-yl)hexadecanoic acid [2-(2-{[2-(2-carbamoylmethoxyethoxy)ethylcarbamoyl]methoxy}ethoxy)ethyl]amide.

In another embodiment the invention provides a compound according to formula (I), wherein the molecule is covalently linked to R via the ε-amino group of a lysine residue.

In another embodiment the invention provides a compound according to formula (I), wherein the molecule is covalently linked to R via the thiol group of a cysteine residue.

In another embodiment the invention provides a compound according to formula (I), wherein the molecule is a therapeutic agent.

In another aspect the invention provides a compound according to formula (I), wherein the therapeutic agent is a biopolymer.

In another aspect the invention provides a compound according to formula (I), wherein the therapeutic agent is a polypeptide.

In another aspect the invention provides a compound according to formula (I), wherein the therapeutic agent is a small molecule drug.

In another aspect the present invention provides a compound according to formula (I), wherein the molecule is a polypeptide which is an insulinotropic peptide.

In one embodiment the invention provides a compound according to formula (I), wherein the molecule is a polypeptide which is GLP-1(7-37) or a variant thereof.

In another embodiment the invention provides a compound according to formula (I), wherein the molecule is a polypeptide which is GLP-1(7-37) or an analog thereof.

In another embodiment the invention provides a compound according to formula (I), wherein the molecule is a polypeptide comprising the amino acid sequence of the formula (III):

```
Formula (III)
                                                            (SEQ ID No: 3)
Xaa7-Xaa8-Glu-Gly-Thr-Phe-Thr-Ser-Asp-Xaa16-Ser-Xaa18-Xaa19-Xaa20-Glu-Xaa22-Xaa23-Ala- Xaa25-Xaa26-Xaa27-Phe-Ile-Xaa30-Trp-Leu-Xaa33-Xaa34-Xaa35-Xaa36-Xaa37-Xaa38-Xaa39-

Xaa40-Xaa41-Xaa42-Xaa43-Xaa44-Xaa45-Xaa46
``` wherein $Xaa_7$ is L-histidine, D-histidine, desamino-histidine, 2-amino-3-(2-aminoimidazol-4-yl)propionic acid, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, 1-aminocyclopropanecarboxylic acid, 1-aminocyclobutanecarboxylic acid, 1-aminocyclopentanecarboxylic acid, 1-aminocyclohexanecarboxylic acid, 1-aminocycloheptanecarboxylic acid, or 1-aminocyclooctanecarboxylic acid;
$Xaa_{16}$ is Val or Leu;
$Xaa_{18}$ is Ser, Lys or Arg;
$Xaa_{19}$ is Tyr or Gln;
$Xaa_{20}$ is Leu or Met;
$Xaa_{22}$ is Gly, Glu or Aib;
$Xaa_{23}$ is Gln, Glu, Lys or Arg;
$Xaa_{25}$ is Ala or Val;
$Xaa_{26}$ is Lys, Glu or Arg;
$Xaa_{27}$ is Glu or Leu;
$Xaa_{30}$ is Ala, Glu or Arg;
$Xaa_{33}$ is Val or Lys;
$Xaa_{34}$ is Lys, Glu, Asn or Arg;
$Xaa_{35}$ is Gly or Aib;
$Xaa_{36}$ is Arg, Gly or Lys;
$Xaa_{37}$ is Gly, Ala, Glu, Pro, Lys, amide or is absent;
$Xaa_{38}$ is Lys, Ser, amide or is absent;
$Xaa_{39}$ is Ser, Lys, amide or is absent;
$Xaa_{40}$ is Gly, amide or is absent;
$Xaa_{41}$ is Ala, amide or is absent;
$Xaa_{42}$ is Pro, amide or is absent;
$Xaa_{43}$ is Pro, amide or is absent;
$Xaa_{44}$ is Pro, amide or is absent;
$Xaa_{45}$ is Ser, amide or is absent;
$Xaa_{46}$ is amide or is absent;
provided that if $Xaa_{38}$, $Xaa_{39}$, $Xaa_{40}$, $Xaa_{41}$, $Xaa_{42}$, $Xaa_{43}$, $Xaa_{44}$, $Xaa_{45}$ or $Xaa_{46}$ is absent then each amino acid residue downstream is also absent.

In another embodiment the invention provides a compound according to formula (I), wherein the molecule is a polypeptide comprising the amino acid sequence of formula (IV):

```
Formula (IV)
                                                            (SEQ ID No: 4)
Xaa7-Xaa8-Glu-Gly-Thr-Phe-Thr-Ser-Asp-Val-Ser-Xaa18-Tyr-Leu-Glu-Xaa22-Xaa23-Ala-Ala- Xaa26-Glu-Phe-Ile-Xaa30-Trp-Leu-Val-Xaa34-Xaa35-Xaa36-Xaa37-Xaa38
``` wherein
$Xaa_7$ is L-histidine, D-histidine, desamino-histidine, 2-aminohistidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, 1-aminocyclopropanecarboxylic acid, 1-aminocyclobutanecarboxylic acid, 1-aminocyclopentanecarboxylic acid, 1-aminocyclohexanecarboxylic acid, 1-aminocycloheptanecarboxylic acid, or 1-aminocyclooctanecarboxylic acid;
$Xaa_{18}$ is Ser, Lys or Arg;
$Xaa_{22}$ is Gly, Glu or Aib;
$Xaa_{23}$ is Gln, Glu, Lys or Arg;
$Xaa_{26}$ is Lys, Glu or Arg;
$Xaa_{30}$ is Ala, Glu or Arg;
$Xaa_{34}$ is Lys, Glu or Arg;
$Xaa_{35}$ is Gly or Aib;

Xaa$_{36}$ is Arg or Lys;
Xaa$_{37}$ is Gly, Ala, Glu or Lys;
Xaa$_{38}$ is Lys, amide or is absent.

In another embodiment the invention provides a compound according to formula (I), wherein the molecule is a polypeptide selected from GLP-1(7-35), GLP-1(7-36), GLP-1(7-36)-amide, GLP-1(7-37), GLP-1(7-38), GLP-1(7-39), GLP-1(7-40), GLP-1(7-41) or an analog thereof.

In another embodiment the invention provides a compound according to formula (I), wherein the molecule is a polypeptide comprising no more than fifteen amino acid residues which have been exchanged, added or deleted as compared to GLP-1(7-37) (SEQ ID No: 1), or no more than ten amino acid residues which have been exchanged, added or deleted as compared to GLP-1(7-37) (SEQ ID No: 1).

In another embodiment the invention provides a compound according to formula (I), wherein the molecule is a polypeptide comprising no more than six amino acid residues which have been exchanged, added or deleted as compared to GLP-1(7-37) (SEQ ID No: 1).

In another embodiment the invention provides a compound according to formula (I), wherein the molecule is a polypeptide comprising no more than 4 amino acid residues which are not encoded by the genetic code.

In another embodiment the invention provides a compound according to formula (I), wherein the molecule is a polypeptide which is a DPP-IV protected insulinotropic peptide.

In another embodiment the invention provides a compound according to formula (I), wherein the molecule is a polypeptide comprising an Aib residue in position 8.

In another embodiment the invention provides a compound according to formula (I), wherein the molecule is a GLP-1(7-37) analog wherein the amino acid residue in position 7 of said polypeptide is selected from the group consisting of D-histidine, desamino-histidine, 2-amino-3-(2-aminoimidazol-4-yl)propionic acid, β-hydroxy-histidine, homohistidine, Nα-acetyl-histidine, α-fluoromethyl-histidine, α-methyl-histidine, 3-pyridylalanine, 2-pyridylalanine and 4-pyridylalanine.

In another embodiment the invention provides a compound according to formula (I), wherein the molecule is a GLP-1(7-37) analog selected from the group consisting of Arg$^{34}$GLP-1(7-37) (SEQ ID NO: 7), Lys$^{38}$Arg$^{26,34}$GLP-1(7-38) (SEQ ID NO: 26), Lys$^{38}$Arg$^{26,34}$GLP-1(7-38)-OH (SEQ ID NO: 26), Lys$^{36}$Arg$^{26,34}$GLP-1(7-36) (SEQ ID NO: 27), Aib$^{8,22,35}$GLP-1(7-37) (SEQ ID NO: 28), Aib$^{8,35}$GLP-1(7-37) (SEQ ID NO: 29), Aib$^{8,22}$ GLP-1(7-37) (SEQ ID NO: 30), Aib$^{8,22,35}$Arg$^{26,34}$Lys$^{38}$GLP-1(7-38) (SEQ ID NO: 31), Aib$^{8,35}$Arg$^{26,34}$Lys$^{38}$GLP-1(7-38) (SEQ ID NO: 32), Aib$^{8,22}$Arg$^{26,34}$Lys$^{38}$GLP-1(7-38) (SEQ ID NO: 33), Aib$^{8,22,35}$ Arg$^{26,34}$Lys$^{38}$GLP-1(7-38) (SEQ ID NO: 31), Aib$^{8,35}$Arg$^{26,34}$Lys$^{38}$GLP-1(7-38) (SEQ ID NO: 32), Aib$^{8,22}$ $_{35}$Arg$^{26}$Lys$^{38}$GLP-1(7-38) (SEQ ID NO: 34), Aib$^{8,}$ $_{35}$Arg$^{26}$Lys$^{38}$GLP-1(7-38) (SEQ ID NO: 35), Aib$^{8,}$ $_{22}$Arg$^{26}$Lys$^{38}$GLP-1(7-38) (SEQ ID NO: 36), Aib$^{8,22,}$ $_{35}$Arg$^{34}$Lys$^{38}$GLP-1(7-38) (SEQ ID NO: 37), Aib$^{8,}$ $_{35}$Arg$^{34}$Lys$^{38}$GLP-1(7-38) (SEQ ID NO: 38), Aib$^{8,}$ $_{22}$Arg$^{34}$Lys$^{38}$GLP-1(7-38) (SEQ ID NO: 39), Aib$^{8,22,}$ $_{35}$Ala$^{37}$Lys$^{38}$GLP-1(7-38) (SEQ ID NO: 40), Aib$^{8,}$ $_{35}$Ala$^{37}$Lys$^{38}$GLP-1(7-38) (SEQ ID NO: 41), Aib$^{8,}$ $_{22}$Ala$^{37}$Lys$^{38}$GLP-1(7-38) (SEQ ID NO: 42), Aib$^{8,22,35}$Lys$^{37}$GLP-1(7-37) (SEQ ID NO: 6), Aib$^{8,35}$Lys$^{37}$GLP-1(7-37) (SEQ ID NO: 43) and Aib$^{8,22}$Lys$^{37}$GLP-1(7-38) (SEQ ID NO: 12).

In another embodiment the invention provides a compound according to formula (I), wherein the molecule is GLP-1(7-37) or an analog thereof which is attached to R via the amino acid residue in position 23, 26, 34, 36 or 38 relative to the amino acid sequence SEQ ID No: 1.

In another aspect the present invention provides a compound according to formula (I), wherein the molecule is exendin-4(1-39) (SEQ ID No: 2) or an analog thereof.

In one embodiment the invention provides a compound according to formula (I), wherein the molecule is an exendin-4 analog comprising no more than twelve amino acid residues which have been exchanged, added or deleted as compared to exendin-4(1-39) (SEQ ID No: 2), or no more than eight amino acid residues which have been exchanged, added or deleted as compared to exendin-4(1-39) (SEQ ID No: 2).

In another embodiment the invention provides a compound according to formula (I), wherein the molecule is ZP-10, i.e.

```
                                    (SEQ ID No. 5)
HGEGTFTSDLSKQMEEEAVRLFIEWLKNGGPSSGAPPSKKKKKKamide.
```

In another embodiment the invention provides a compound according to formula (I), wherein said compound is selected from the group consisting of N-ε-26-(16-[5-tetrazolyl]hexadecanoyl)Arg$^{34}$GLP-1-(7-37), (0113-0000-0090) (Derivative of SEQ ID NO: 7)

Gly$^8$,Arg$^{26,34}$GLP-1(7-37)Lys(16-(5-tetrazolyl)hexadecanoyl), (0113-0000-0098) (Derivative of SEQ ID NO: 8)

Gly$^8$,Arg$^{26,34}$GLP-1(7-37)Lys{-4-[N-(16-{5-tetrazolyl}hexadecanoyl)sulfamoyl]butyryl}, (0113-0000-0099) (Derivative of SEQ ID NO: 8)

N-ε-26-{4-[N-(16-{5-tetrazolyl}hexadecanoyl)sulfamoyl]butyryl}Arg$^{34}$GLP-1(7-37), (0113-0000-0100) (Derivative of SEQ ID NO: 7)

N-ε-37-(2-(2-(2-(16-(tetrazol-5-yl)(hexadecanoylamino)ethoxy)ethoxy)acetyl))

Aib$^{8,22,35}$Lys$^{37}$GLP-1(7-37), (NNC 0113-0075) (Derivative of SEQ ID NO: 6)

Gly$^8$, Glu$^{22,23,30}$Arg$^{18,26,34}$GLP-1(7-37)Lys(16-(1H-tetrazol-5-yl)hexadecanoic acid [2-(2-{[2-(2-carbamoyl-methoxyethoxy)ethylcarbamoyl]methoxy}ethoxy)ethyl] amide)-NH$_2$, and (0113-0000-0134) (Derivative of SEQ ID NO: 9)

Gly$^8$Arg$^{26,34}$GLP-1(7-37)Lys(4-(4-(4-(4-(5-tetrazolyl)phenyl)phenyl)phenoxy)butyryl). (NNC 0113-0000-0140) (Derivative of SEQ ID NO: 8)

N-ε$^{38}$-(2-(2-(2-(16-(4-(5-tetrazolyl)phenoxy)hexadecanoyl)ethoxy)ethoxy)acetyl) [Gly8,Arg26,34,Lys38] GLP-1(7-37) peptide 0113-0000-0160 (Derivative of SEQ ID NO: 8)

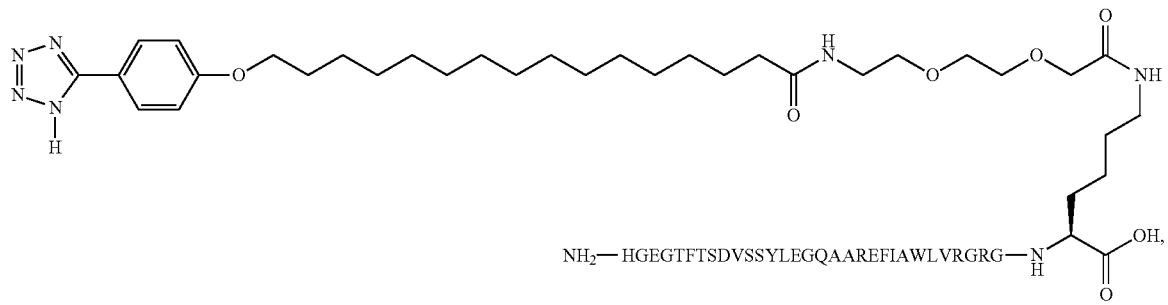
N-epsilon37-(2-(2-(2-(16-(4-(5-Tetrazolyl)phenoxy)
hexadecanoyl)ethoxy)ethoxy)acetyl)[Aib8,22,35,
Lys37]GLP-1 (7-37) 0113-0000-0161 (Derivative of
SEQ ID NO: 6)
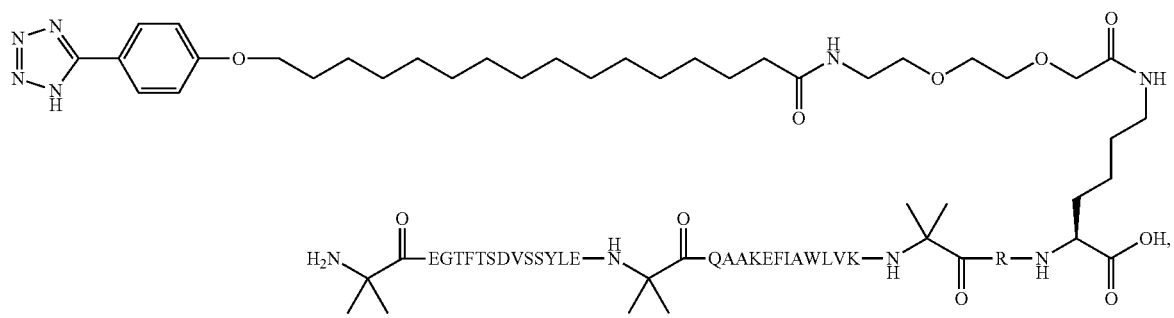
$N^{\epsilon 38}$-(2-(2-(2-(16-(Tetrazol-5-yl)hexadecanoyl)ethoxy)
ethoxy)acetyl) [Aib8,Arg26,34,Lys38]GLP-1(7-37)
peptide 0113-0000-0208 (Derivative of SEQ ID NO: 16)
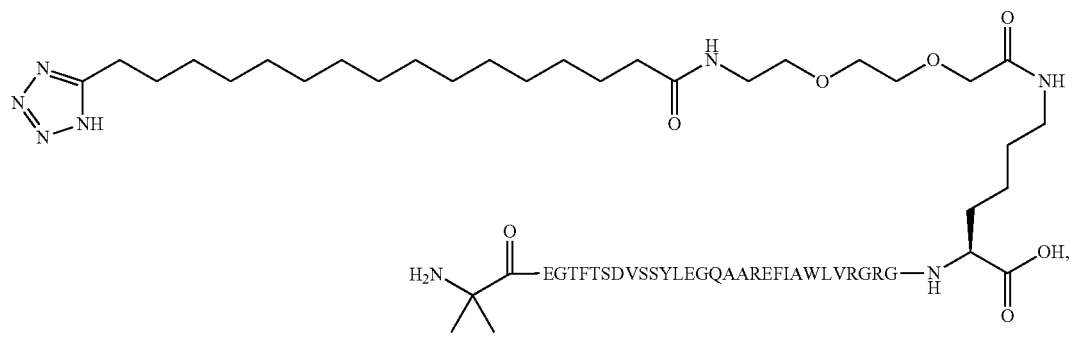
$N^{\epsilon 38}$-(4-(N-(16-(Tetrazol-5-yl)hexadecanoyl)sulfamoyl)
butyryl) [Aib8,Arg26,34,Lys38]GLP-1(7-37) peptide
0113-0000-210 (Derivative of SEQ ID NO: 16)

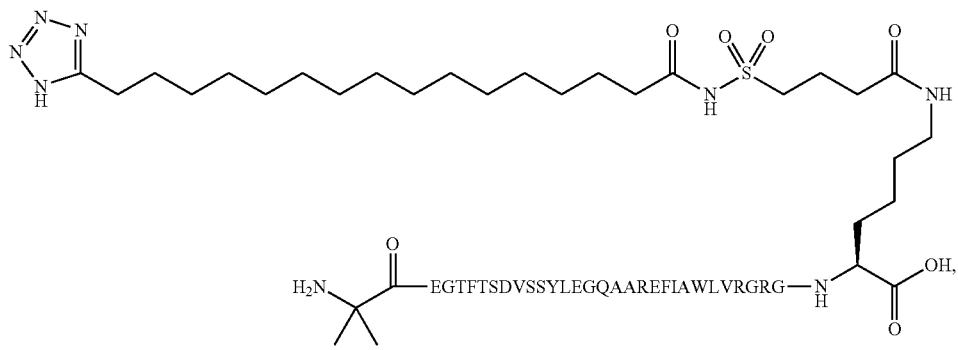
N-epsilon32-(4-[N-(16-{5-Tetrazolyl}hexadecanoyl)sulfamoyl]butyryl)-[Lys32]Exendin[1-39] peptide 0113-0000-0211 (Derivative of SEQ ID NO:17)
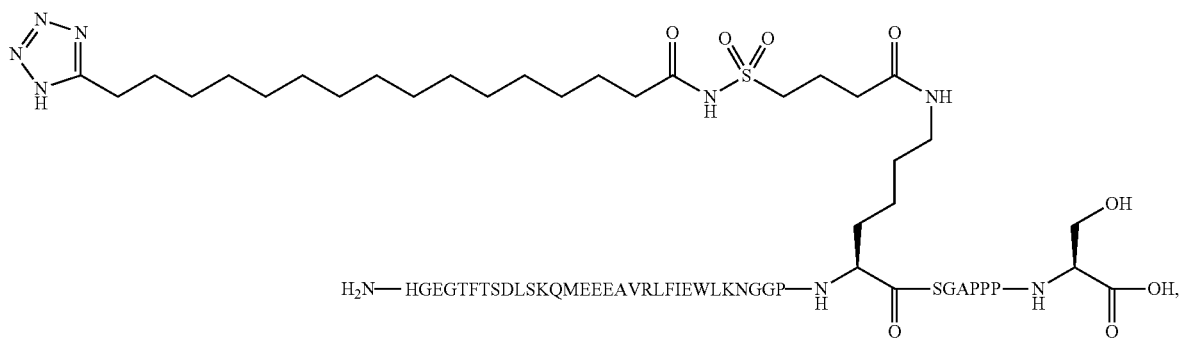
(0113-0000-0150, PrnC) N-epsilon37-(16-(4'-(Tetrazol-5-yl)biphenyl)-4-yloxy)hexadecanoyl) [3-(4-imidazolyl)propionyl7,Aib22,35,Arg26,34,Lys37]GLP-1 (7-37) peptide (Derivative of SEQ ID NO: 10)
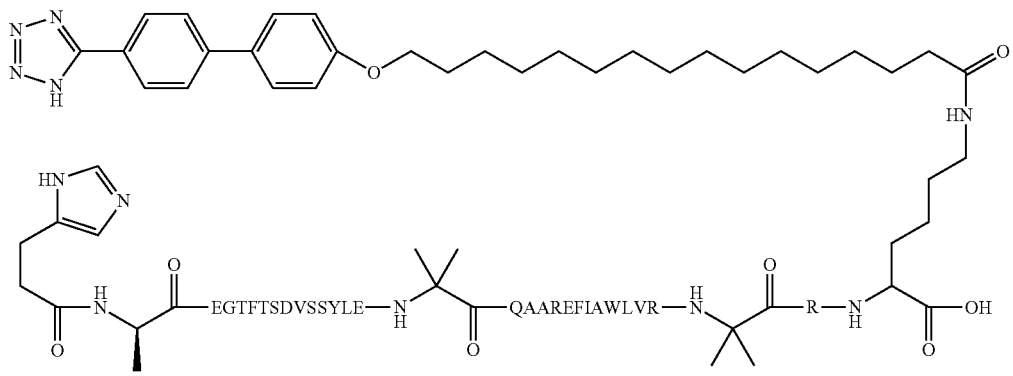
(0113-0000-0151, PrnC) N-epsilon37-(16-(Tetrazol-5-yl)hexadecanoyl) [3-(4-imidazolyl)propionyl7,Aib22,35,Arg26,34,Lys37]GLP-1 (7-37) (Derivative of SEQ ID NO: 10)

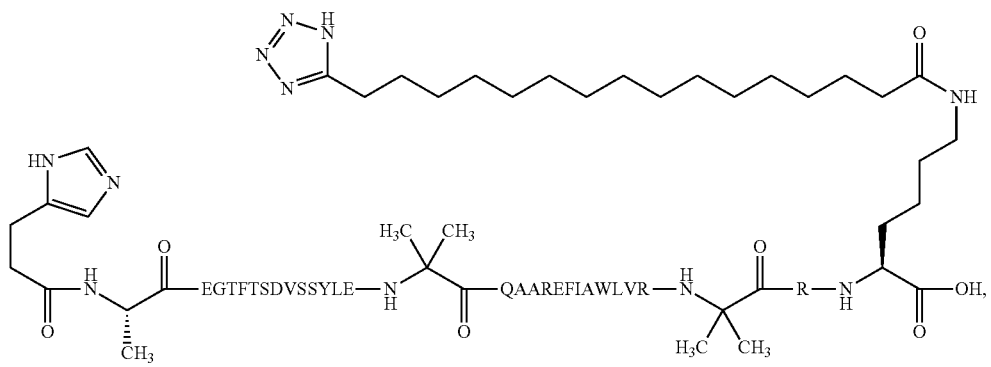
(0113-0000-0152, PrnC) N-epsilon37-(16-(4-(Tetrazol-5-yl)phenoxy)hexadecanoyl) [3-(4-imidazolyl)propionyl7,Aib22,35,Arg26,34,Lys37]GLP-1 (7-37) (Derivative of SEQ ID NO: 10)
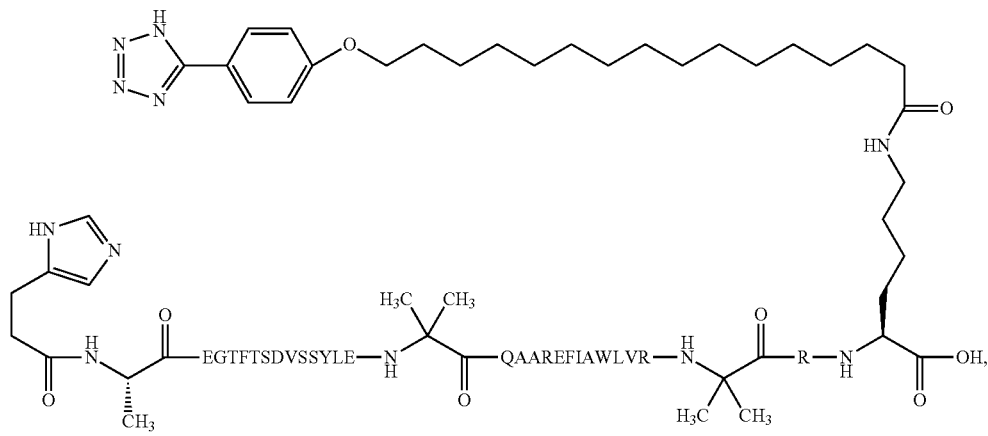
(0113-0000-0153, PrnC) N-epsilon37-(4-(4-(Tetrazol-5-yl)[1,1',4',1"]terphenyl-4"yloxy)butyroyl) [3-(4-imidazolyl)propionyl7,Aib22,35,Arg26,34, Lys37]GLP-1 (7-37) (Derivative of SEQ ID NO: 10)
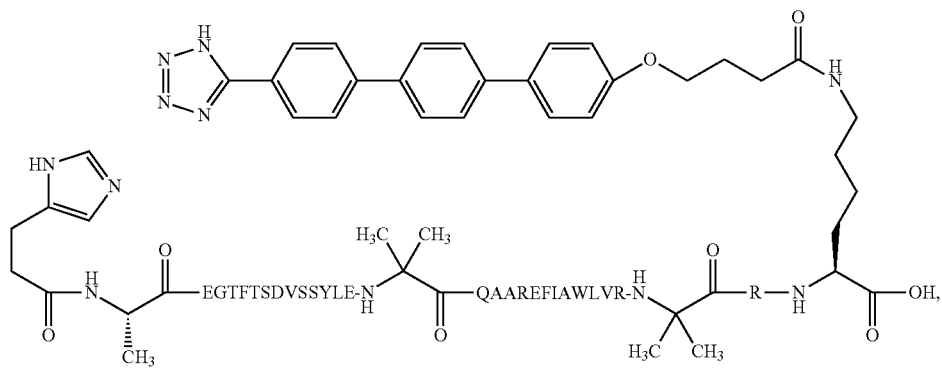
(0113-0000-0154, PrnC) N-epsilon37-(2-(2-(2-(16-(Tetrazol-5-yl)hexadecanoyl)amino)ethoxy)ethoxy)acetyl) [Aib8,22,35,Arg26,34,Lys37] GLP-1 (7-37) (Derivative of SEQ ID NO: 11)

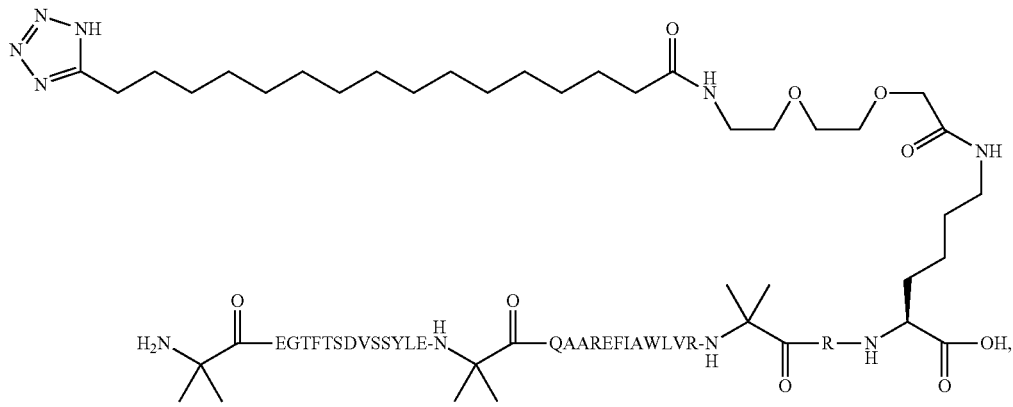
(0113-0000-0155, PrnC) N-epsilon37-(2-(2-(2-(16-(Tetrazol-5-yl)(hexadecanoylamino)ethoxy)ethoxy)acetyl))[3-(4-imidazolyl)propionyl7,Aib22,35,Arg26,34,Lys37] GLP-1 (7-37) peptide (Derivative of SEQ ID NO: 10)
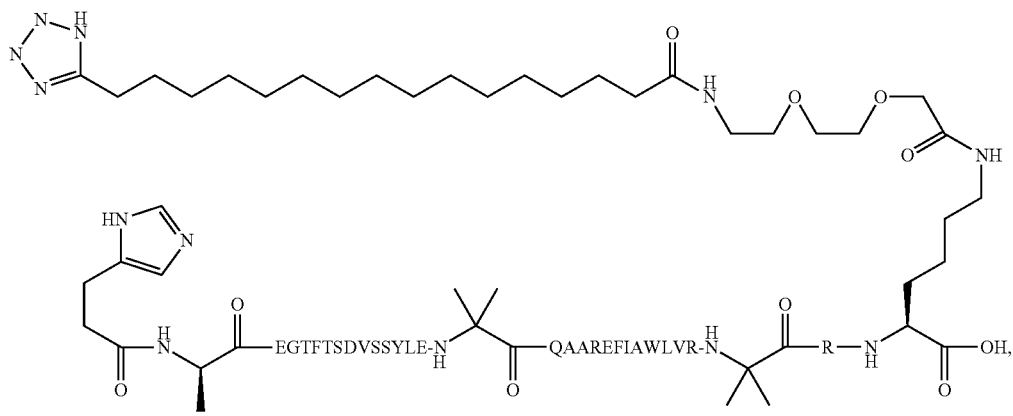
(0113-0000-0156, PrnC) N-epsilon37-(2-(2-(2-(16-(Tetrazol-5-yl)hexadecanoyl)amino)ethoxy)ethoxy)acetyl))[3-(4-imidazolyl)propionyl7,Aib8,22,35,Arg26,34,Lys37] GLP-1 (7-37) peptide (Derivative of SEQ ID NO: 11)
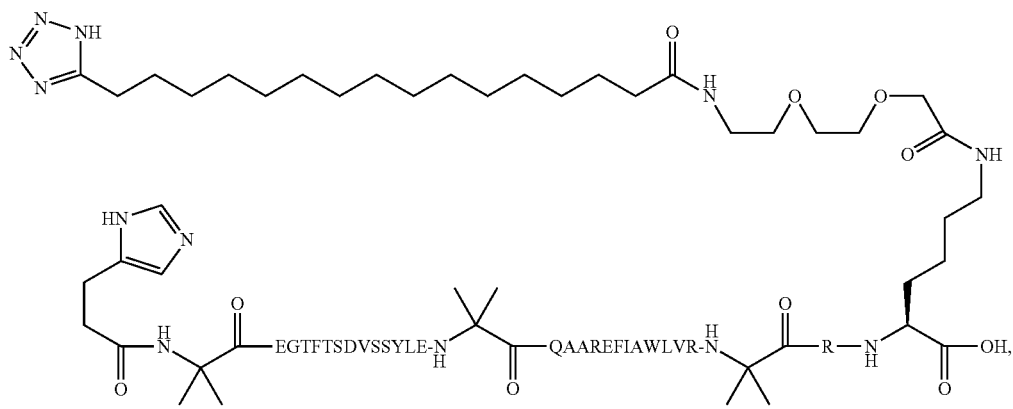

(0113-0000-0202, PrnC) N-epsilon20-(2-(2-(2-(2-(2-(2-(2-(2-(16-(Tetrazol-5-yl)hexadecanoylamino)ethoxy)ethoxy)acetylamino)ethoxy)ethoxy)acetylamino)ethoxy)ethoxy)acetyl) [Lys20] Exendin-4 (1-39)amide (Derivative of SEQ ID NO: 15)

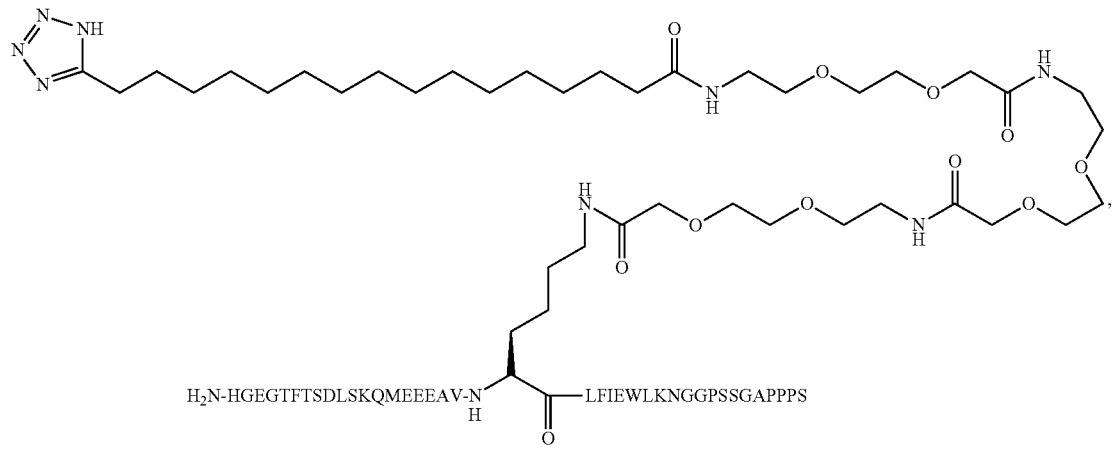

NNC 0100-0000-0508 $N^{\epsilon B29}$-(16-2H-Tetrazol-5-yl-hexadecanoyl) gamma-Glu-des(B30) human insulin, $N^{B29\epsilon}$-4-[4''-(1H-Tetrazol-5-yl)-[1,1';4',1'']terphenyl-4-yloxy]-butyroyl des(B30) insulin

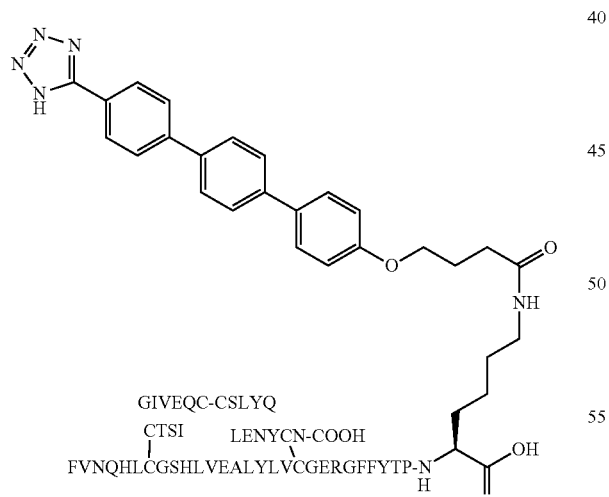

0100-0000-0435, $N^{B29\epsilon}$-16-[4'-(1H-tetrazol-5-yl)-biphenyl-4-yloxy]-hexadecanoyl des(B30) insulin

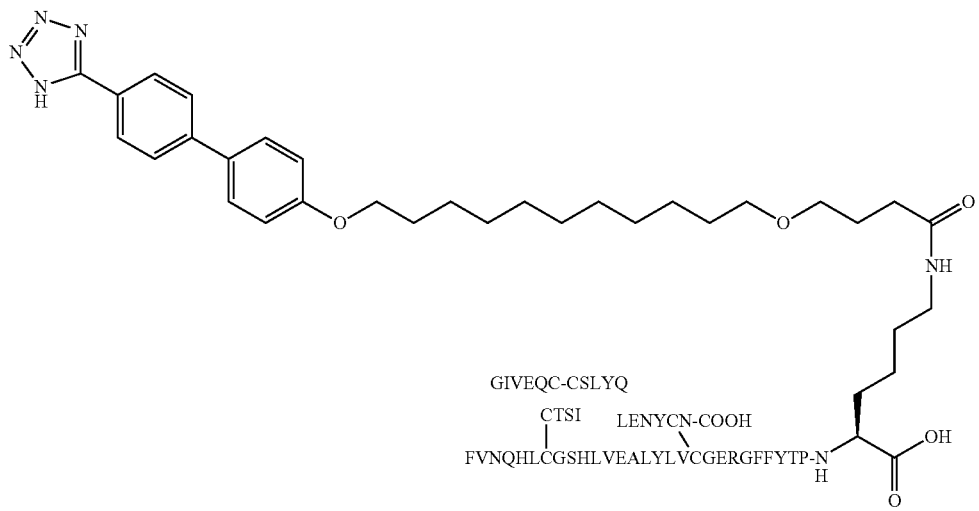
0100-0000-0536,
(0113-0000-0139; HSt)N$^{\epsilon 37}$-16-(4-(4-(5-Tetrazolyl)phenyl)phenyloxy)hexadecanoyl)-[Gly8,Arg26,34]GLP-1-(7-37) peptide (Derivative of SEQ ID NO: 8)
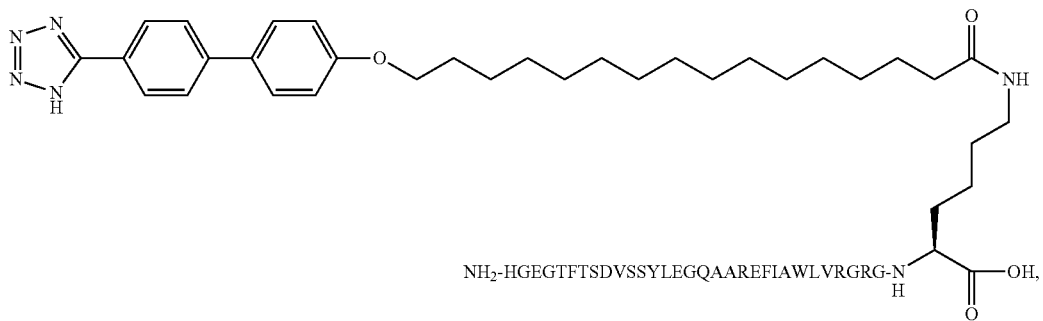
(0113-0000-0140; HSt)N$^{\epsilon 37}$-(4-(4-(4-(4-(5-Tetrazolyl)phenyl)phenyl)phenoxy)butyryl)[Gly8,Arg26,34]GLP-1-(7-37) peptide (Derivative of SEQ ID NO: 8)
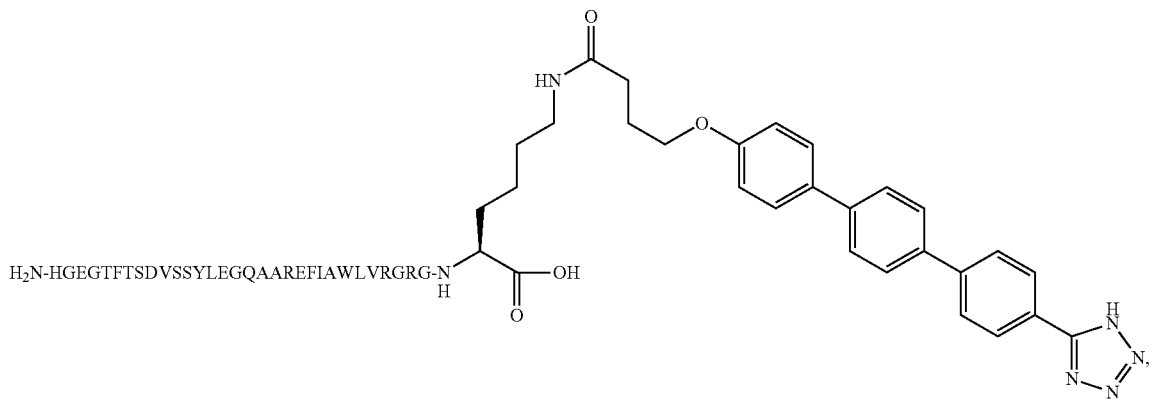
(0113-0000-0166; HSt)N$^{\epsilon 37}$-(17,17-Bis(5-tetrazolyl)heptadecanoyl)[Gly8,Arg26,34]GLP-1-(7-37) peptide (Derivative of SEQ ID NO: 8)

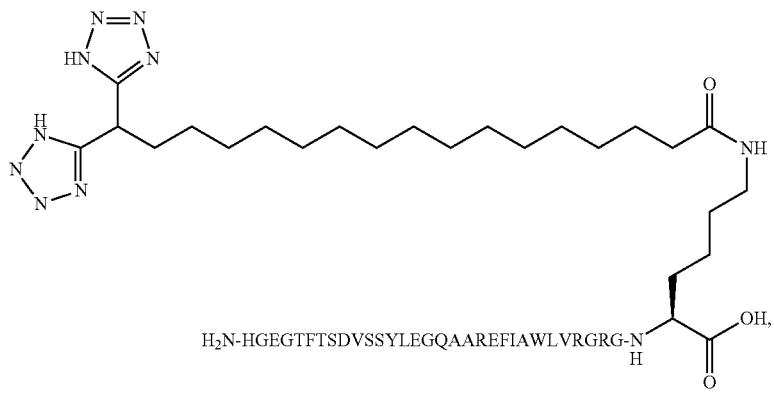
(0113-0000-0169; HSt)N$^{\varepsilon 37}$-(4-(4'-{5-[4-(5-Tetrazolyl)phenyl]-[1,2,4]oxadiazol-3-yl}biphenyl-4-yloxy)butyryl)[Gly8,Arg26,34]GLP-1-(7-37) peptide (Derivative of SEQ ID NO: 8)
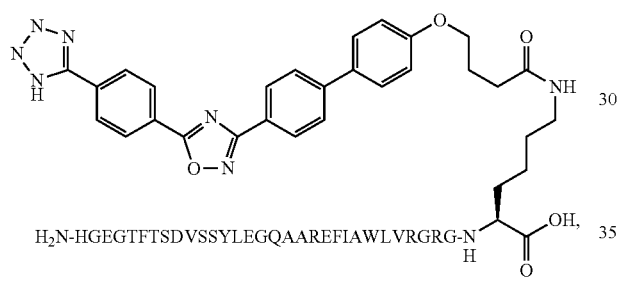
(0113-0000-0174; HSt)N$^{\varepsilon 37}$-(16-(4,5-Bis(5-Tetrazolyl)imidazol-1-yl)hexadecanoyl)[Gly8,Arg26,34]GLP-1-(7-37) peptide (Derivative of SEQ ID NO: 8)
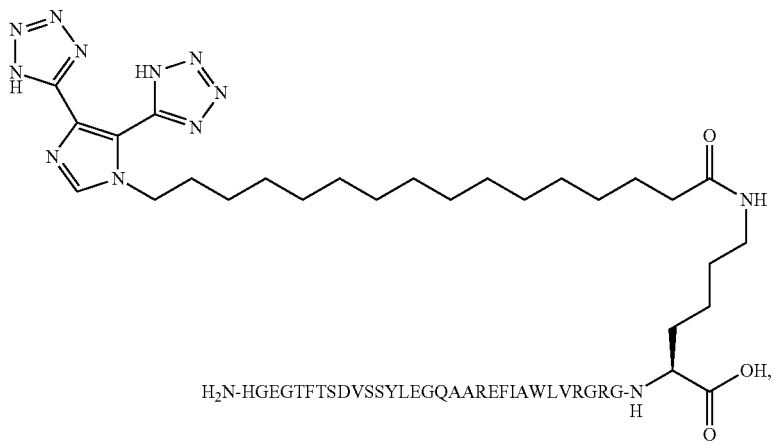
(0113-0000-0197; HSt)N$^{\varepsilon 37}$-((2-(2-(16-(5-Tetrazolyl)hexadecanoylamino)ethoxy)ethoxy)acetyl)[Gly8,Arg26,34]GLP-1-(7-37) peptide (Derivative of SEQ ID NO: 8)

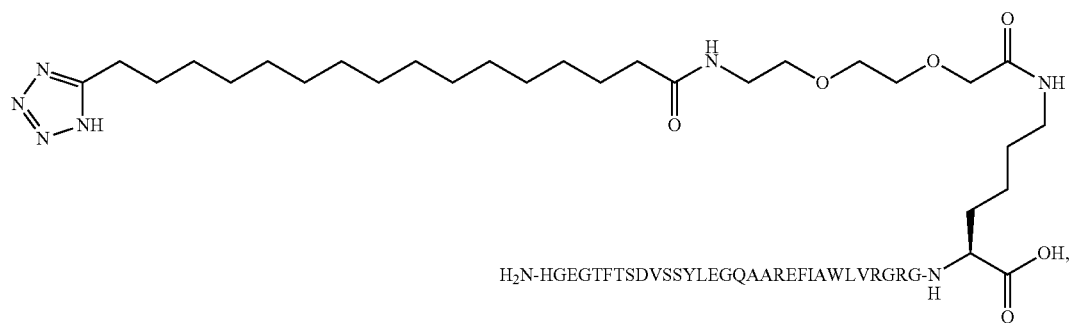
(0113-0000-0184; HSt)N^ε26-(4-{16-(Tetrazol-5-yl)hexadecanoylsulfamoyl}butyryl)[(3-(4-imidazolyl)propionyl7,Arg34]GLP-1-(7-37) peptide (Derivative of SEQ ID NO: 13)
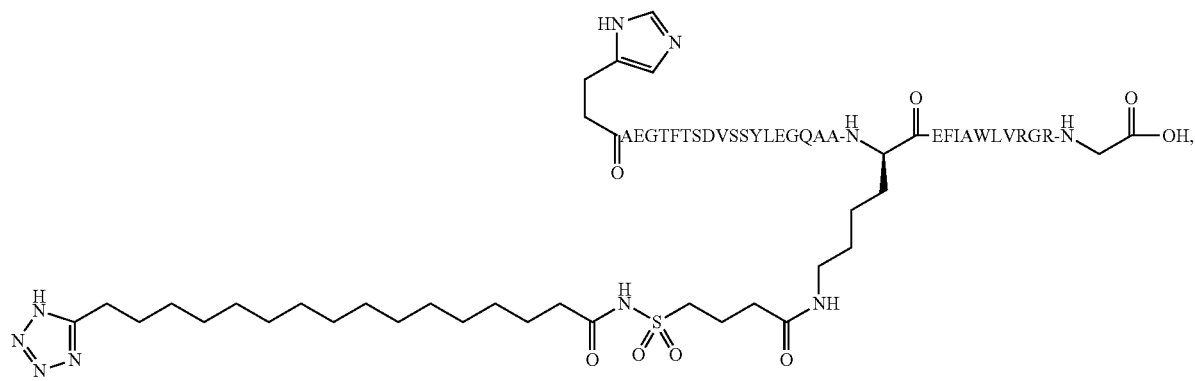
(0113-0000-0196; HSt)N^ε34-(16-{Tetrazol-5-yl}hexadecanoyl)-[Gly8, Arg26] GLP-1 (7-34) peptideamide (Derivative of SEQ ID NO: 14)
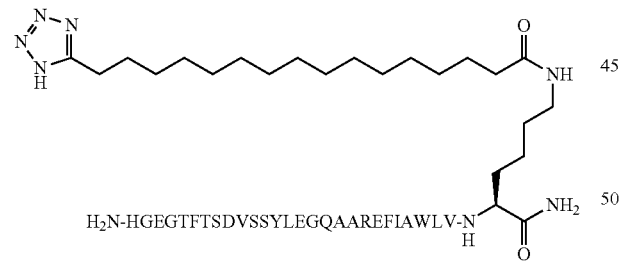
(0113-0000-0205; HSt)N^ε26-({2-[2-(4-(16-(Tetrazol-5-yl)hexadecanoylsulfamoyl)butyrylamino)ethoxy]ethoxy}acetyl)-[Arg34] GLP-1 (7-37) peptide (Derivative of SEQ ID NO: 7)
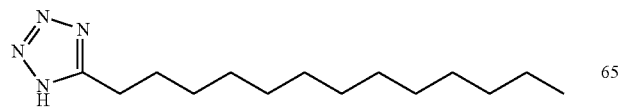

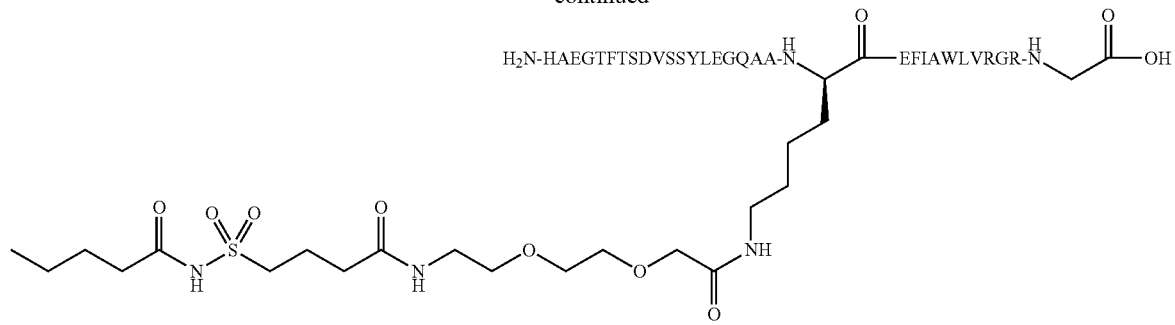

(0113-0000-0206; HSt)N$^{\epsilon34}$-({2-[2-(4-(16-(Tetrazol-5-yl)hexadecanoylsulfamoyl)butyrylamino)ethoxy]ethoxy}acetyl)-[Arg26] GLP-1 (7-34) peptideamide (Derivative of SEQ ID NO: 14)

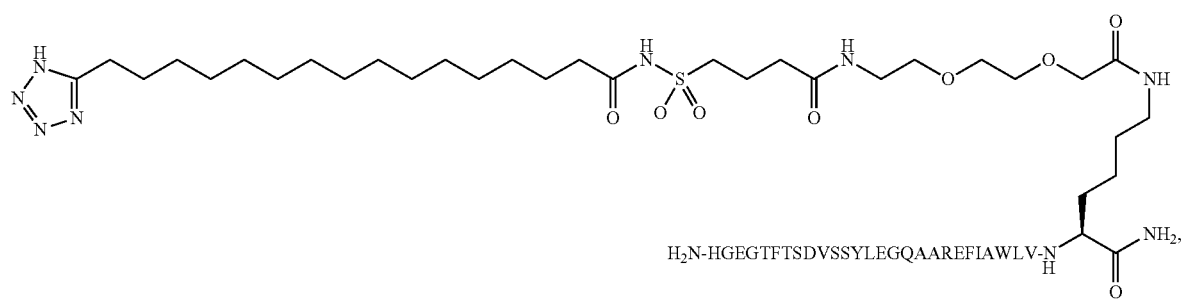

(0113-0000-0207; HSt)N$^{\epsilon26}$-({2-[2-(4-(16-(Tetrazol-5-yl)hexadecanoylsulfamoyl)butyrylamino)ethoxy]ethoxy}acetyl)-[(3-(4-imidazolyl)propionyl) 7,Arg34] GLP-1 (7-37) peptide (Derivative of SEQ ID NO: 13)

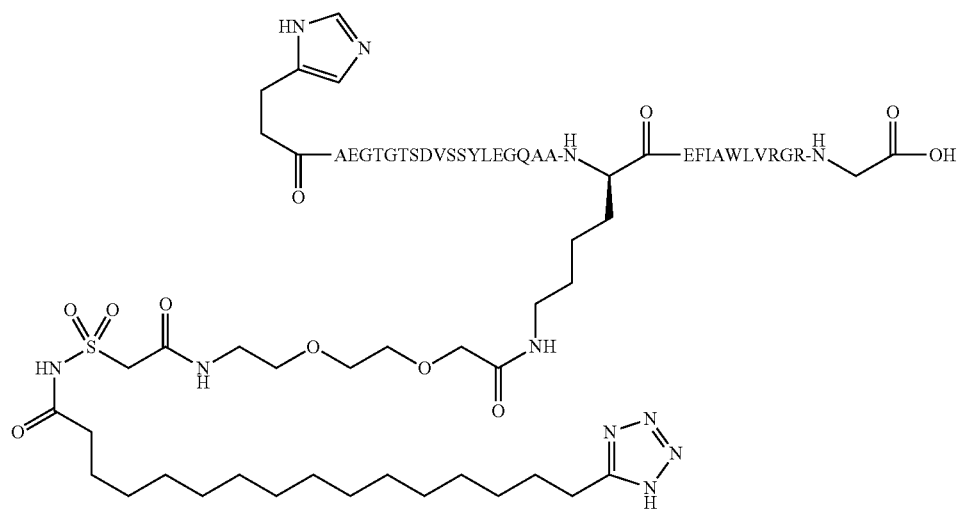

(0113-0000-0214; HSt) N$^{\epsilon26}$-(4-(16-(Tetrazol-5-yl)hexadecanoylsulfamoyl)butyryl)-[Aib8,Arg34]GLP-1-(7-37) peptide (Derivative of SEQ ID NO: 18)

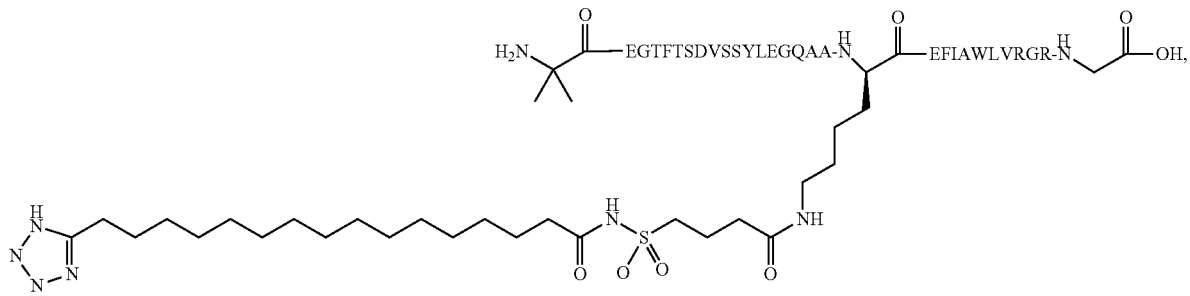
(0113-0000-0223; HSt)N$^{\alpha 7}$(Me)N$^{\epsilon 26}$-(4-(16-(Tetrazol-5-yl)hexadecanoylsulfamoyl)butyryl)-[Arg34]GLP-1-(7-37) peptide (Derivative of SEQ ID NO: 7)
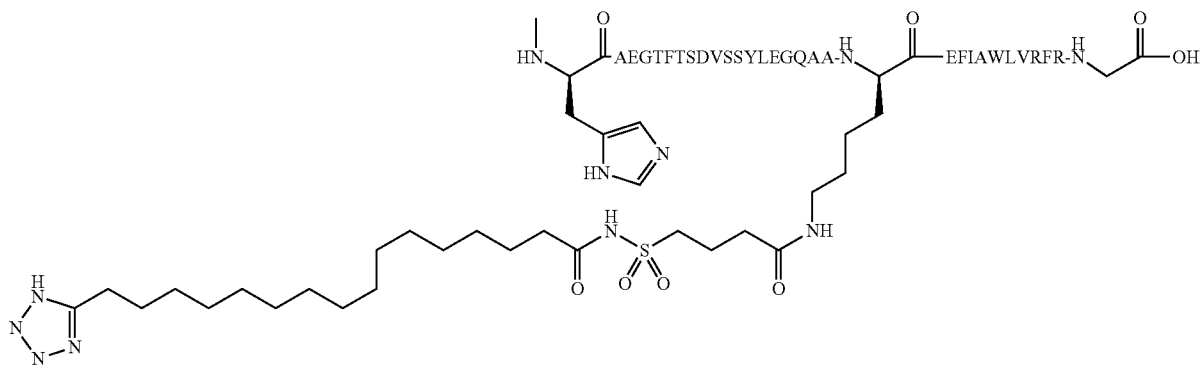
(0113-0000-0224; HSt)N$^{\epsilon 26}$-(4-(16-(Tetrazol-5-yl)hexadecanoylsulfamoyl)butyryl)-[Gly8,Arg34]GLP-1-(7-37) peptide (Derivative of SEQ ID NO: 19)
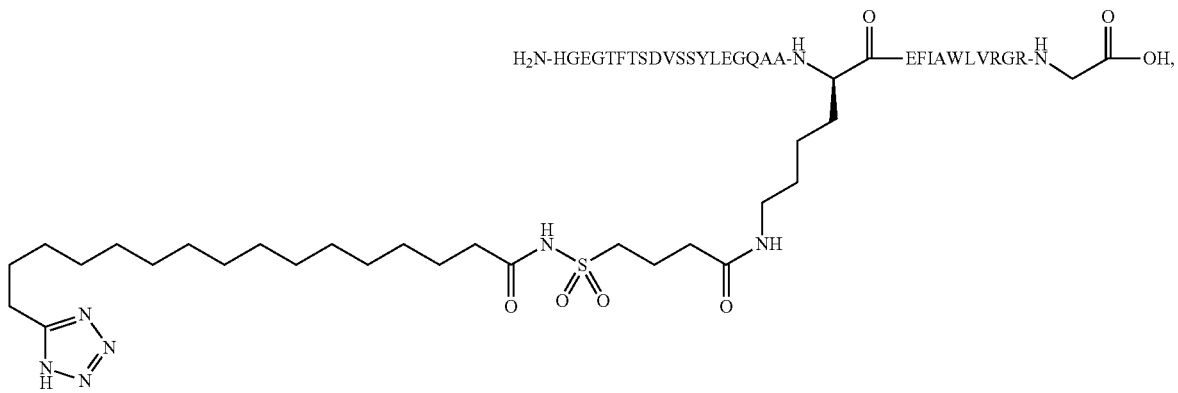
(0113-0000-0244; HSt)N$^{\epsilon 14}$-(4-(16-(Tetrazol-5-yl)hexadecanoylsulfamoyl)butyryl)[Lys14;Arg26,34]GLP-1-(7-37) peptide (Derivative of SEQ ID NO: 20)

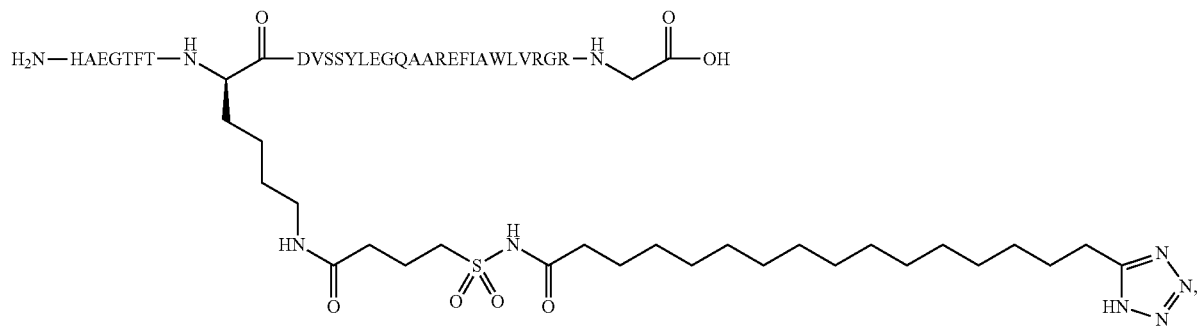
(0113-0000-xxxx; HSt)N^ε18-(4-(16-(Tetrazol-5-yl)hexa-decanoylsulfamoyl)butyryl)[Lys18;Arg26,34]GLP-1-(7-37) peptide (Derivative of SEQ ID NO: 21)
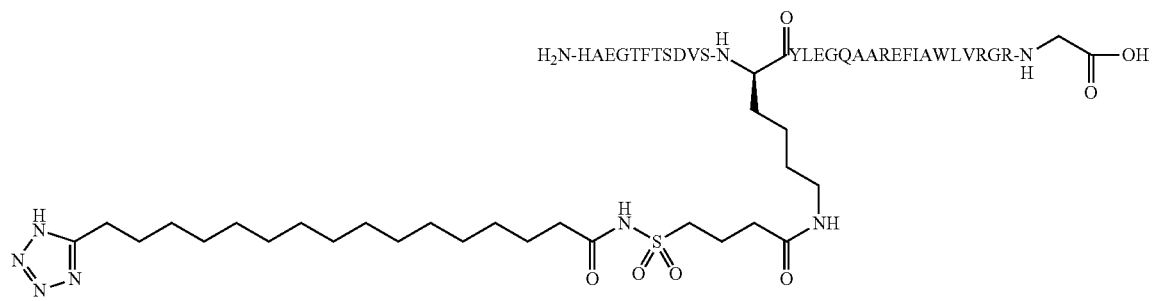
N^ε18-(4-(16-(Tetrazol-5-yl)hexadecanoylsulfamoyl)bu-tyryl)[Gly8;Lys18;Arg26,34]GLP-1-(7-37) peptide (Derivative of SEQ ID NO: 22)
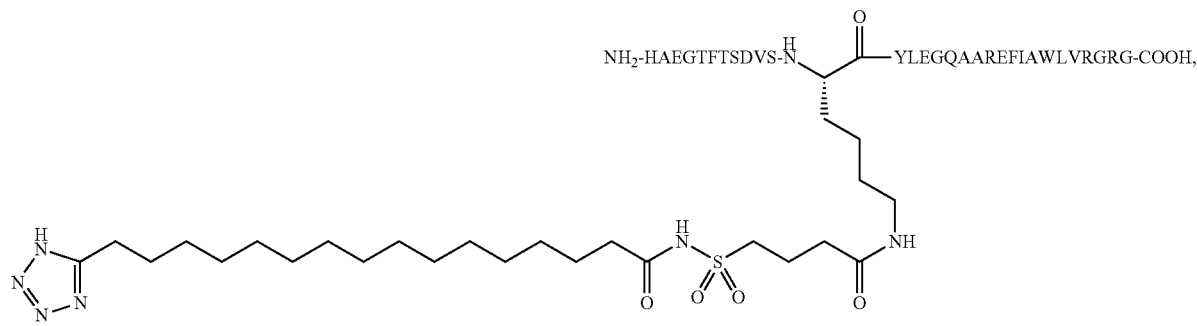
N^ε18-(4-(16-(Tetrazol-5-yl)hexadecanoylsulfamoyl)bu-tyryl)[Aib8,Lys18;Arg26,34]GLP-1-(7-37) peptide (Derivative of SEQ ID NO: 23)

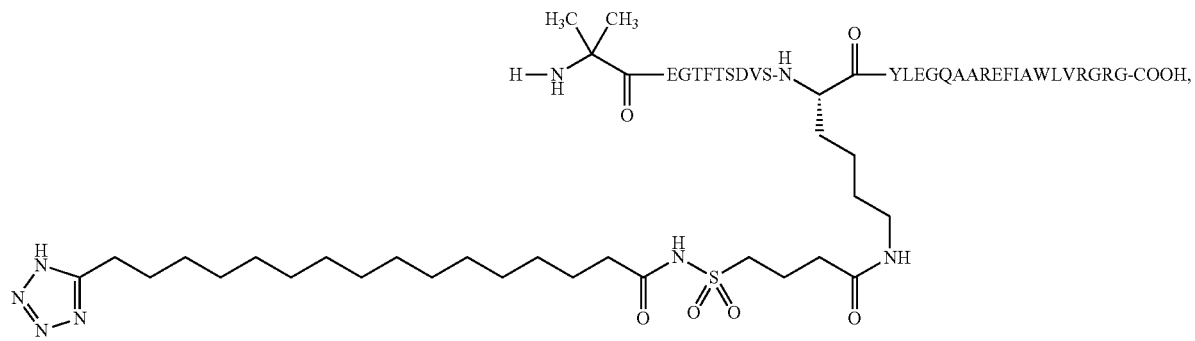

Nᵉ¹⁸-(4-(16-(Tetrazol-5-yl)hexadecanoylsulfamoyl)bu-
tyryl)[3-(4-imidazolyl)propionyl7;Lys18;Arg26,34]GLP-1-
(7-37) peptide (Derivative of SEQ ID NO: 24)

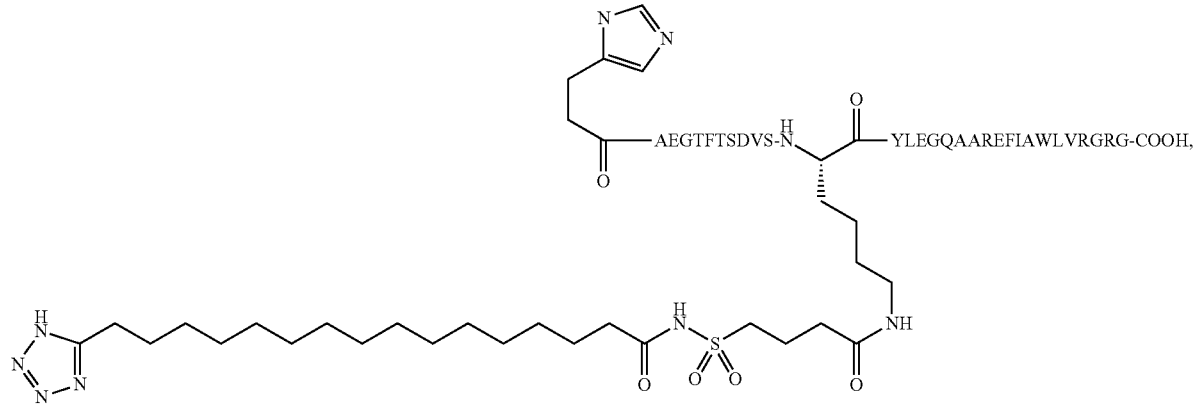

(0113-0000-xxxx; HSt)Nᵉ¹⁸-(4-(16-(Tetrazol-5-yl)hexa-
decanoylsulfamoyl)butyryl)[Lys18;Arg26]GLP-1-(7-
33) peptideamide (Derivative of SEQ ID NO: 25)

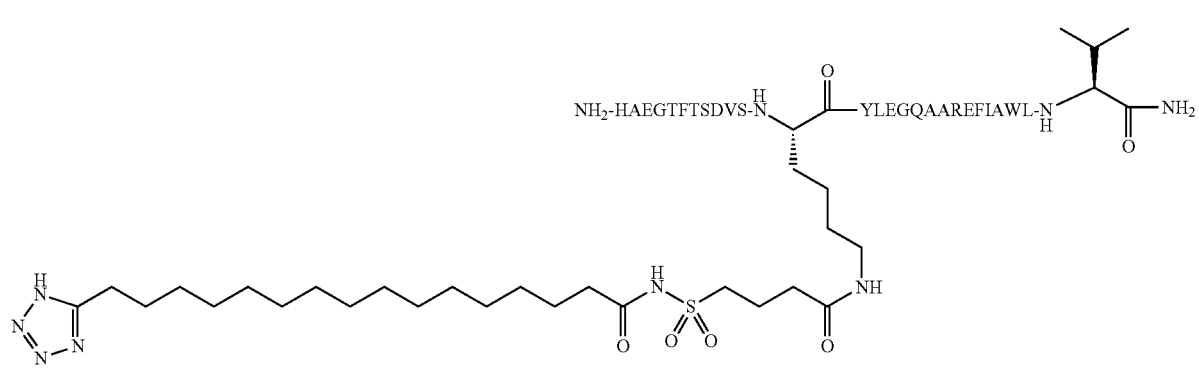

(0113-0000-xxxx; HSt)Nᵉ²⁶-((2-(2-(2-(2-(2-(4-(16-(Tet-
razol-5-yl)hexadecanoylsulfamoyl)butyryl)ethoxy)
ethoxy)acetylamino)ethoxy)ethoxy)acetyl)-[Arg34]
GLP-1-(7-37) peptide (Derivative of SEQ ID NO: 7)

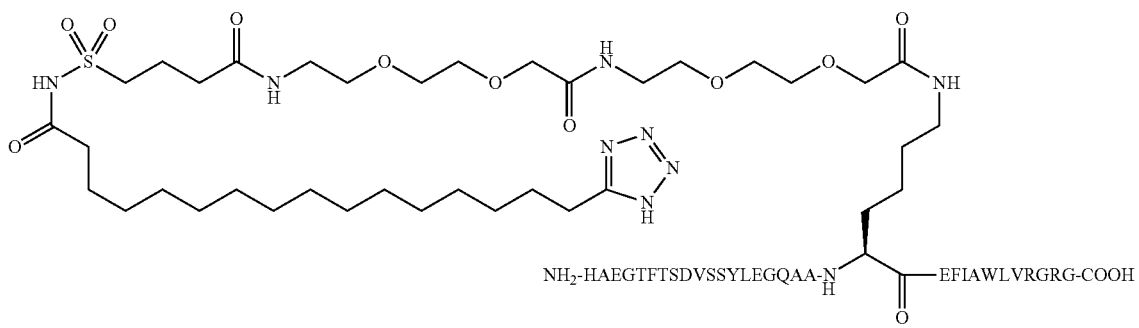
(0113-0000-xxxx; HSt)N^ε26^-((2-(2-(2-(2-(2-(4-(16-(Tetrazol-5-yl)hexadecanoylsulfamoyl)butyryl)ethoxy)ethoxy)acetylamino)ethoxy)ethoxy)acetyl)[Gly8,Arg34]GLP-1-(7-37) peptide (Derivative of SEQ ID NO: 19)
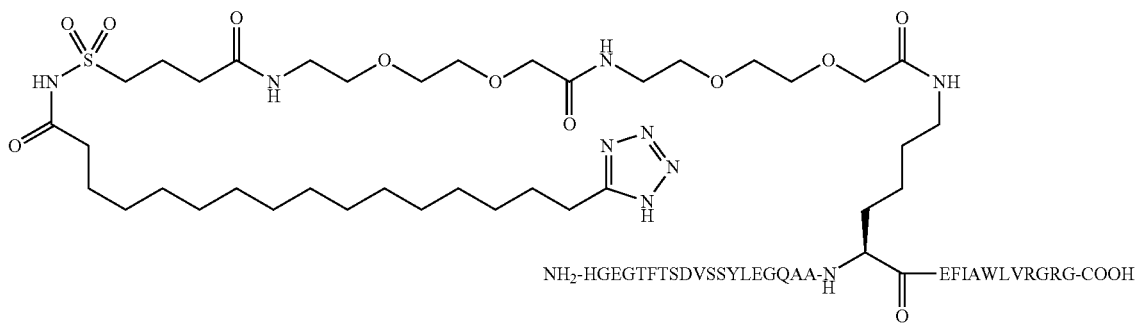
(0113-0000-xxxx; HSt) N^ε26^-((2-(2-(2-(2-(2-(4-(16-(Tetrazol-5-yl)hexadecanoylsulfamoyl)butyryl)ethoxy)ethoxy)acetylamino)ethoxy)ethoxy)acetyl)-[Aib8,Arg34]GLP-1-(7-37) peptide (Derivative of SEQ ID NO: 18)
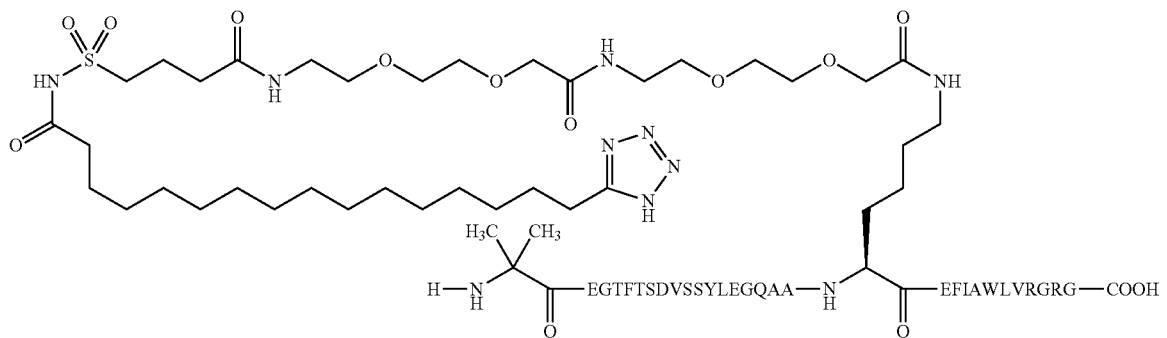

Derivative of SEQ ID NO: 7:
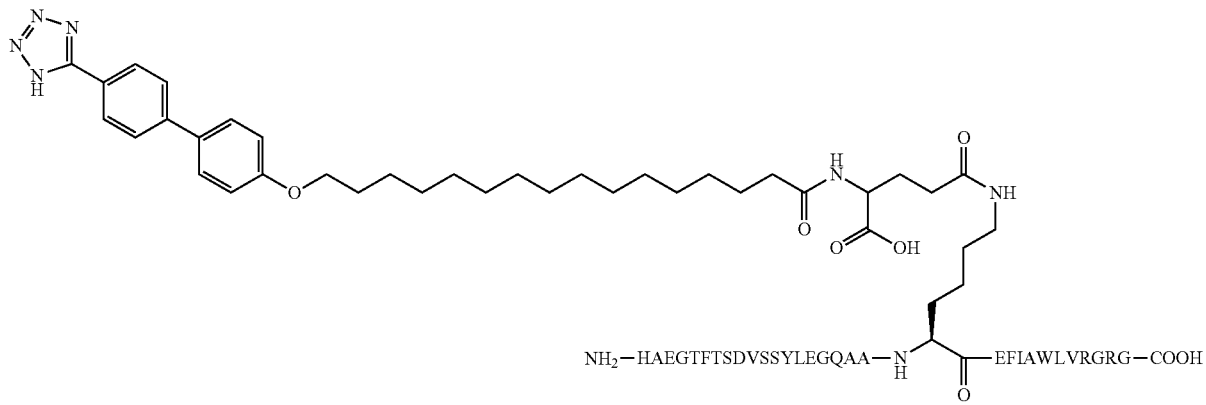
Derivative of SEQ ID NO: 19:
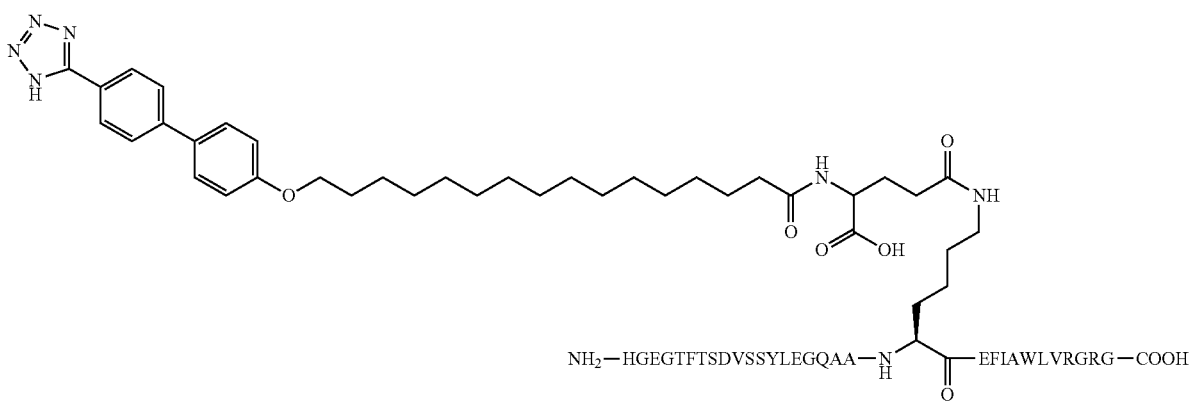
Derivative of SEQ ID NO: 18:
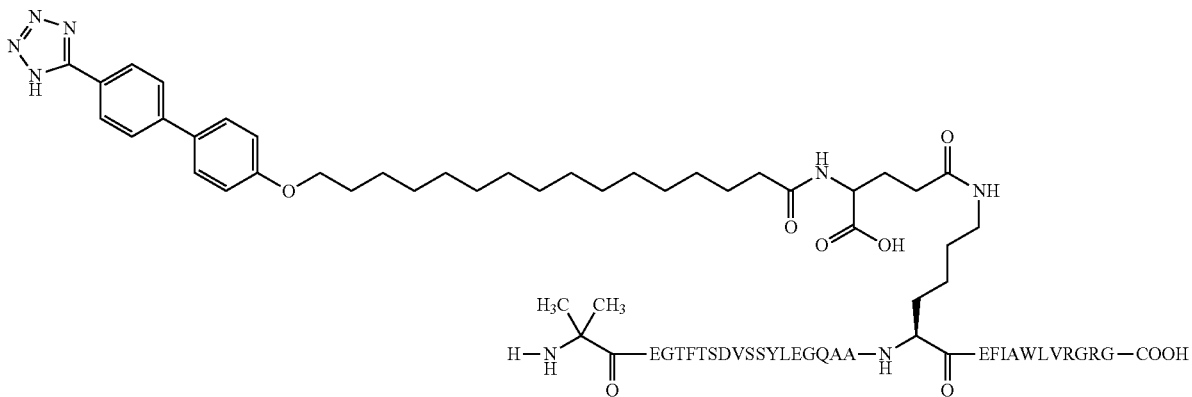

Derivative of SEQ ID NO: 7:
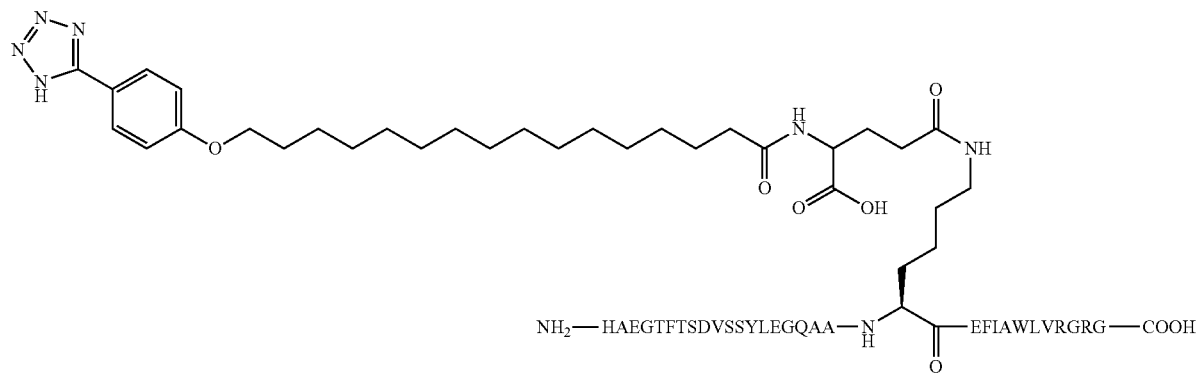
Derivative of SEQ ID NO: 19:
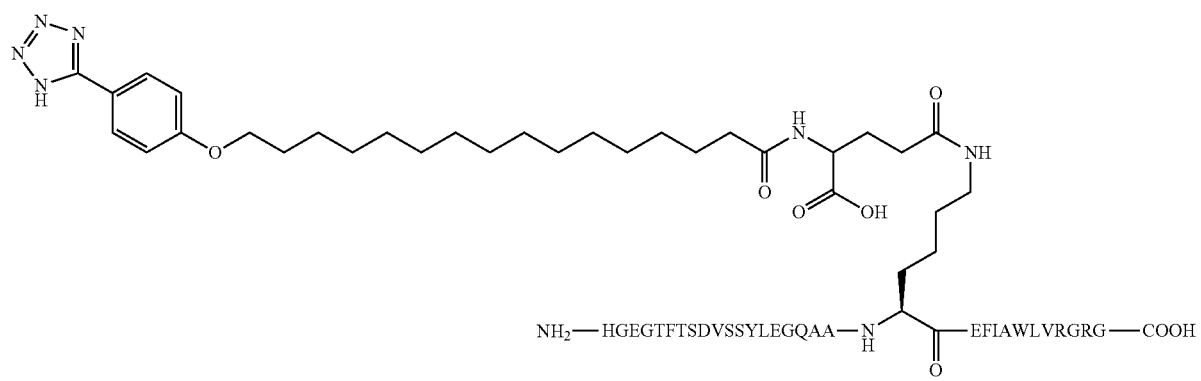
Derivative of SEQ ID NO: 18:
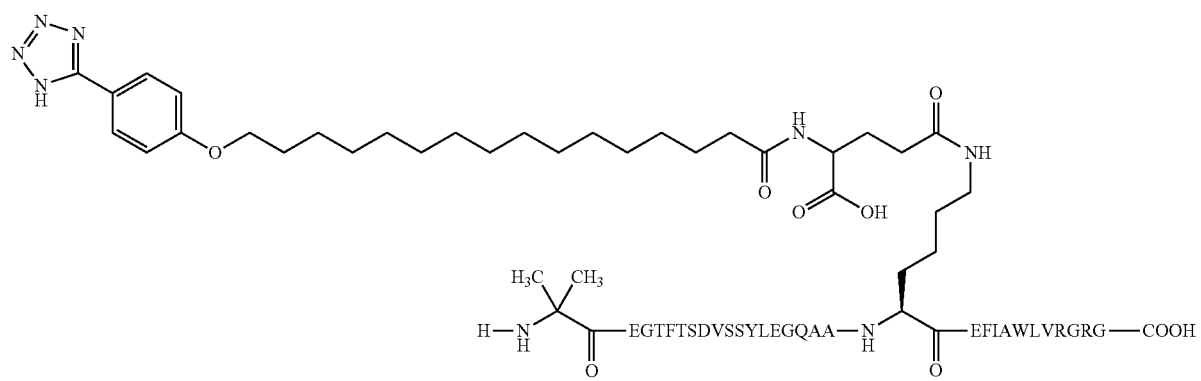

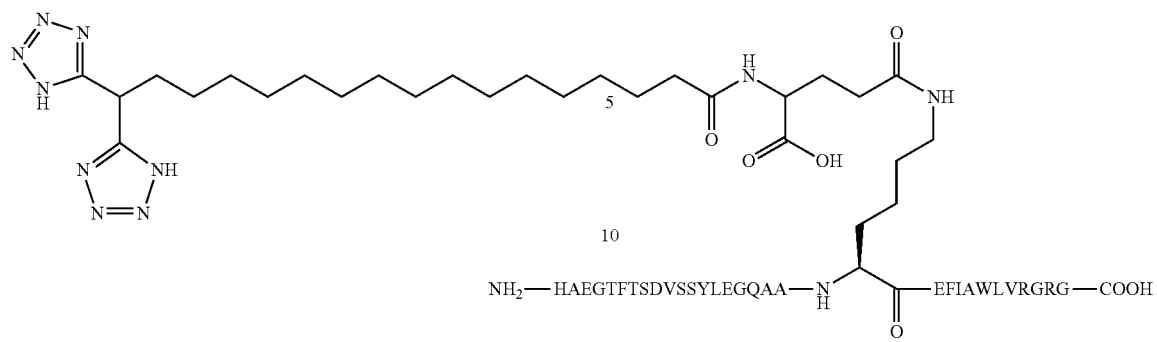
Derivative of SEQ ID NO: 19:
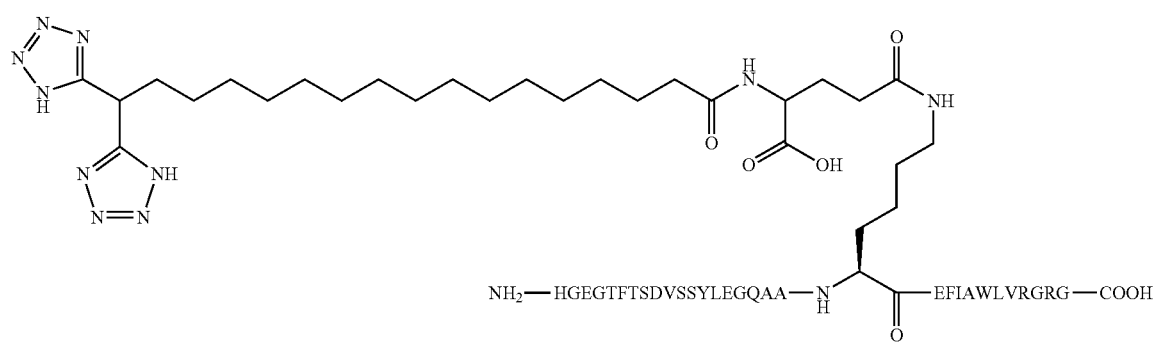
Derivative of SEQ ID NO: 18:
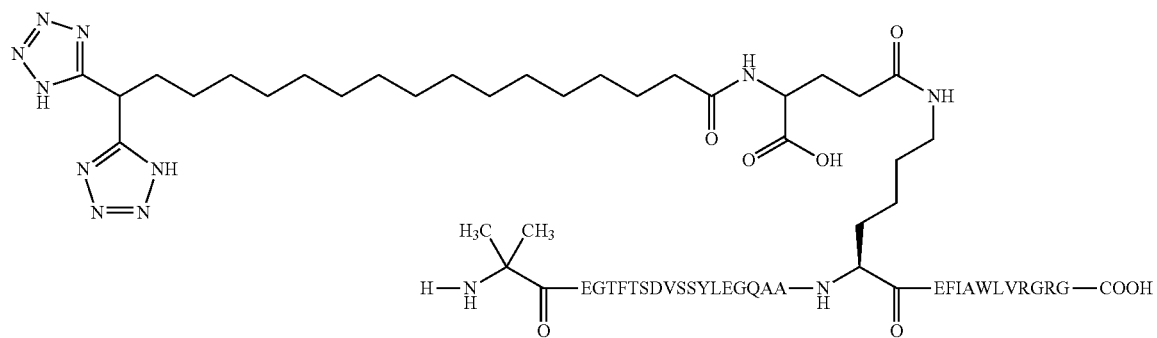

Derivative of SEQ ID NO: 7:
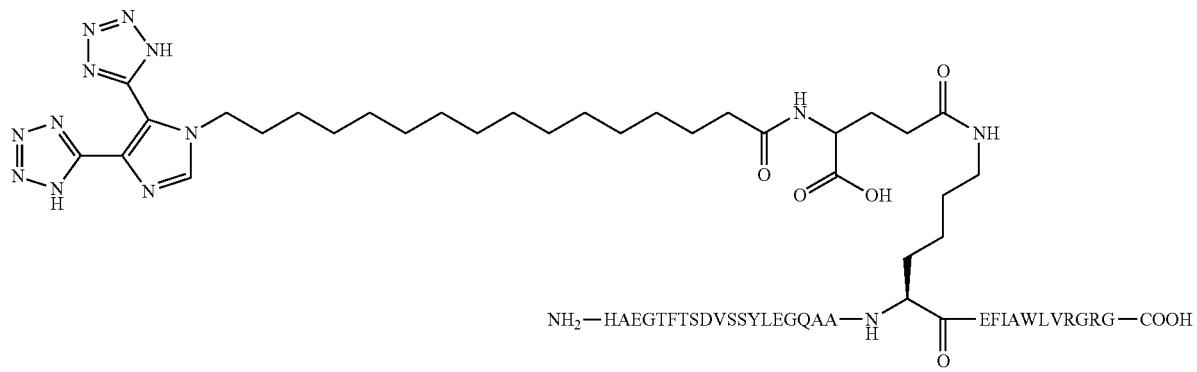
Derivative of SEQ ID NO: 19:
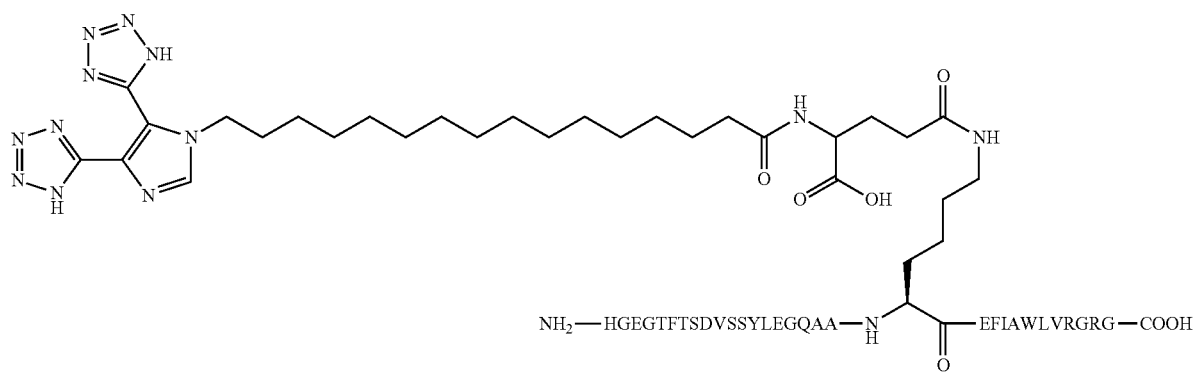
Derivative of SEQ ID NO: 18:
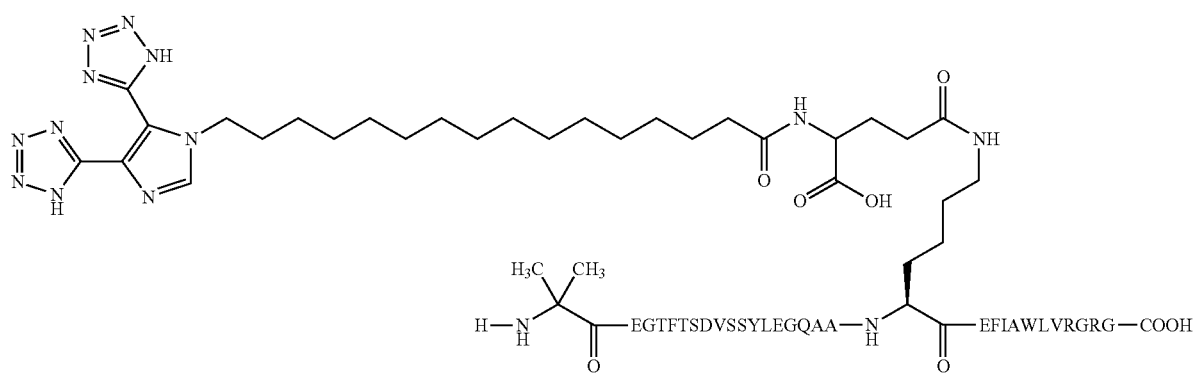

Derivative of SEQ ID NO: 7:
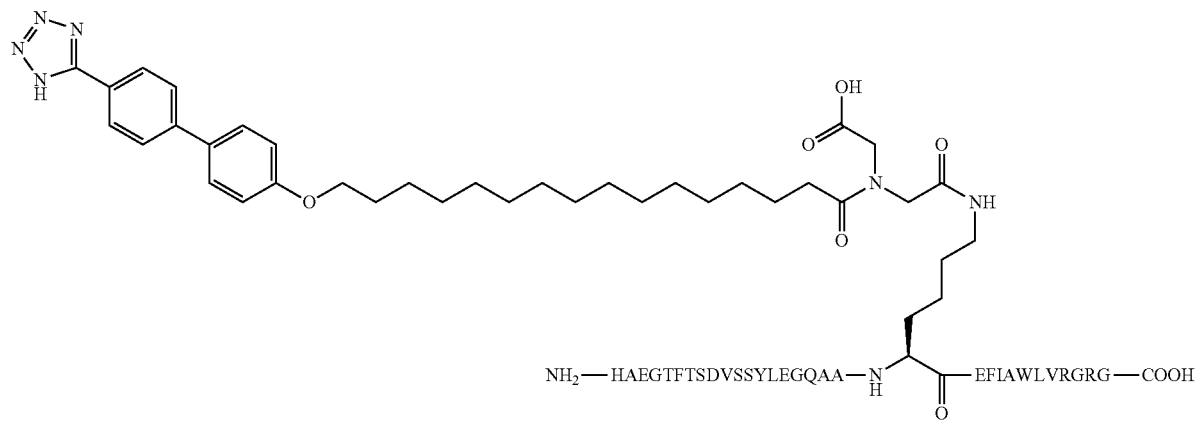
20
Derivative of SEQ ID NO: 7:
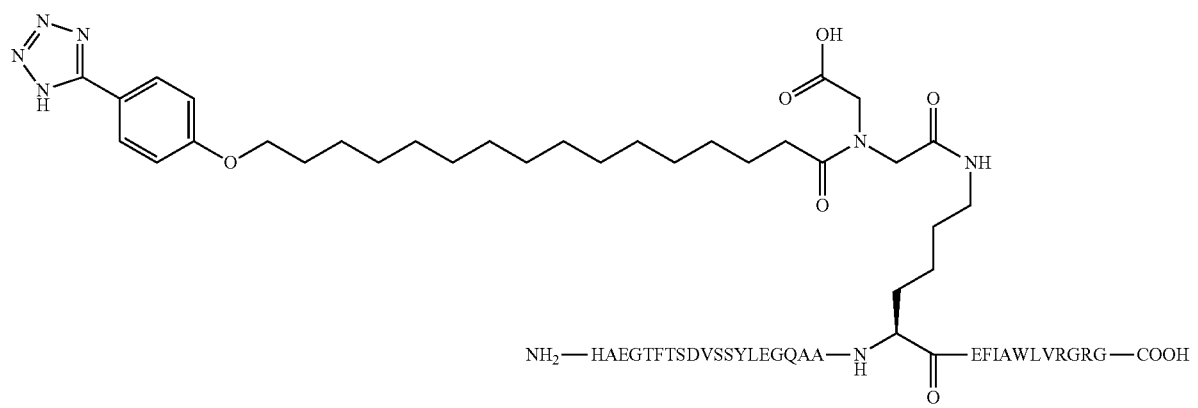
45
Derivative of SEQ ID NO: 7:
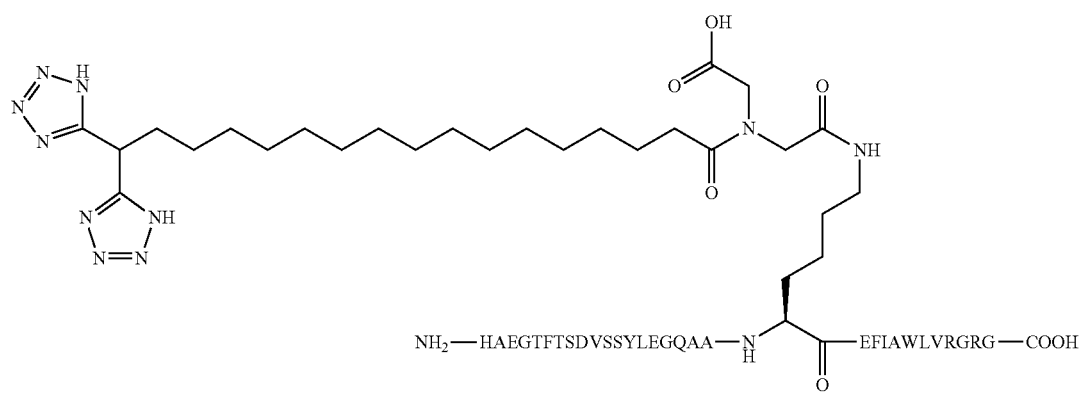

Derivative of SEQ ID NO: 7:
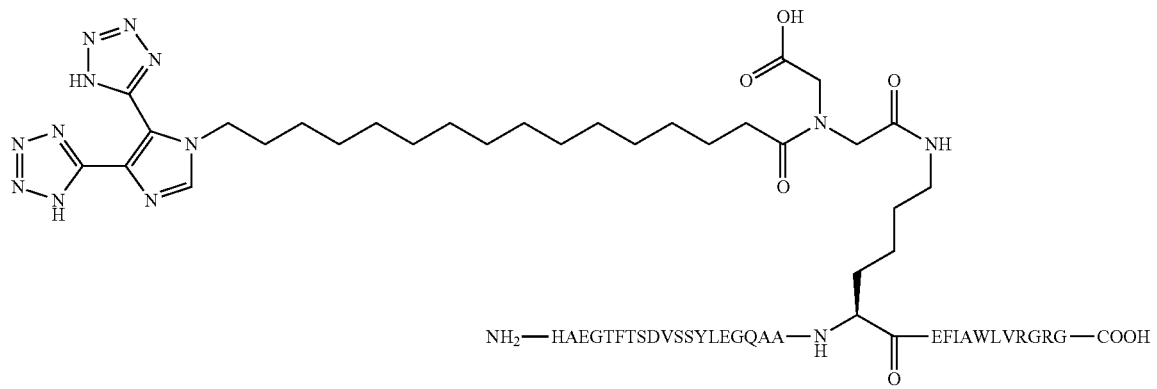
Derivative of SEQ ID NO: 7:
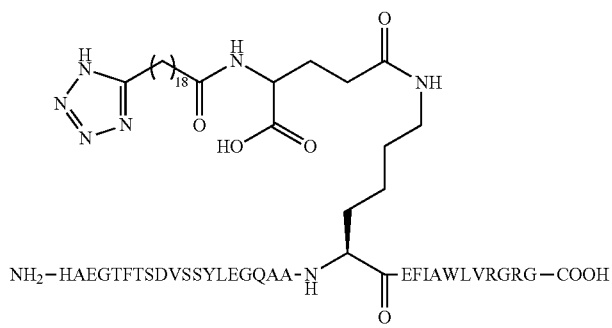
Derivative of SEQ ID NO: 19:
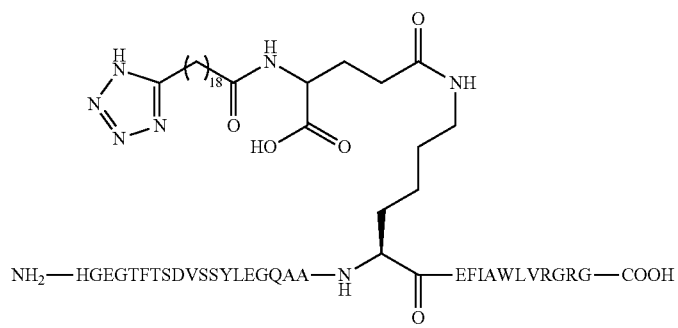
(0113-0000-xxxx; HSt)
$N^{\varepsilon 26}$-(4-(19-(Tetrazol-5-yl)nonadecanoylsulfamoyl)butyryl)[Arg34]GLP-1-(7-37) peptide (Derivative of SEQ ID NO: 7)

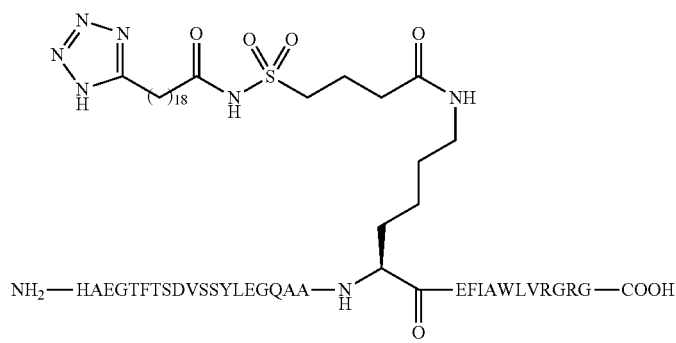
Derivative of SEQ ID NO: 19:
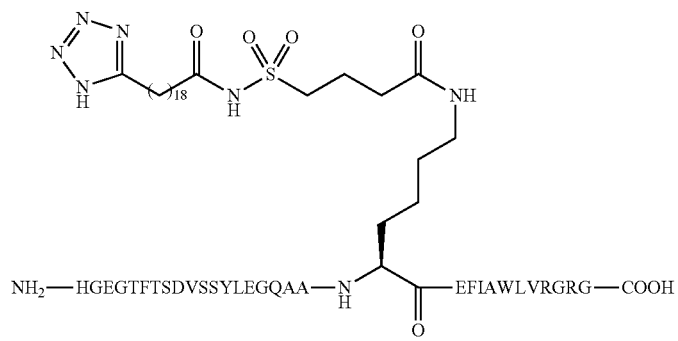
Derivative of SEQ ID NO: 18:
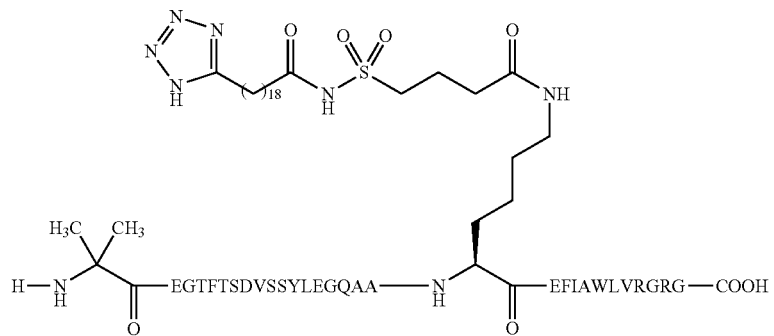
Derivative of SEQ ID NO: 7:
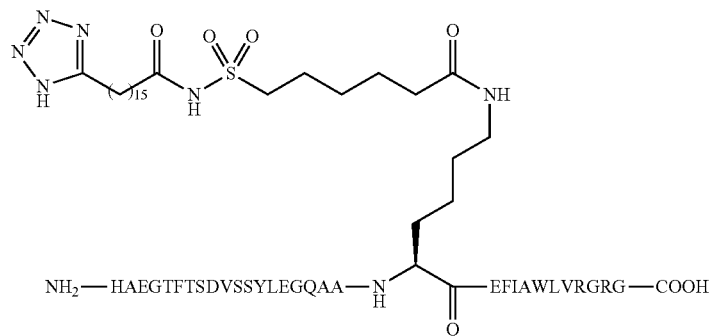

Derivative of SEQ ID NO: 19:
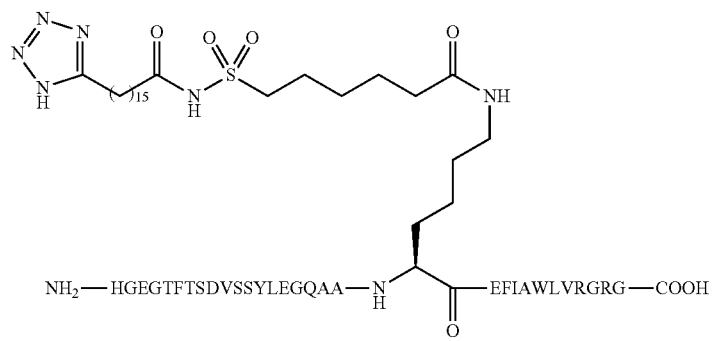
Derivative of SEQ ID NO: 18:
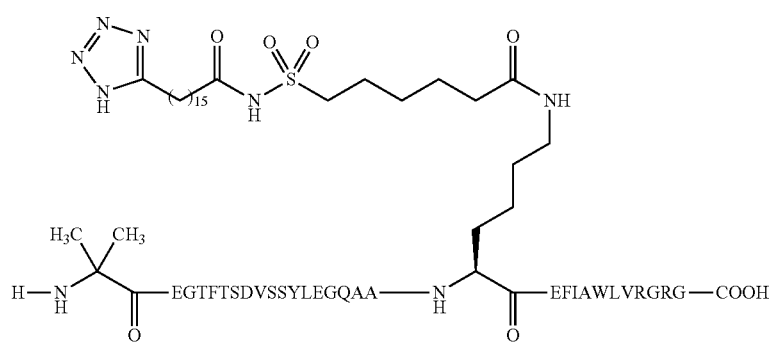
Derivative of SEQ ID NO: 7:
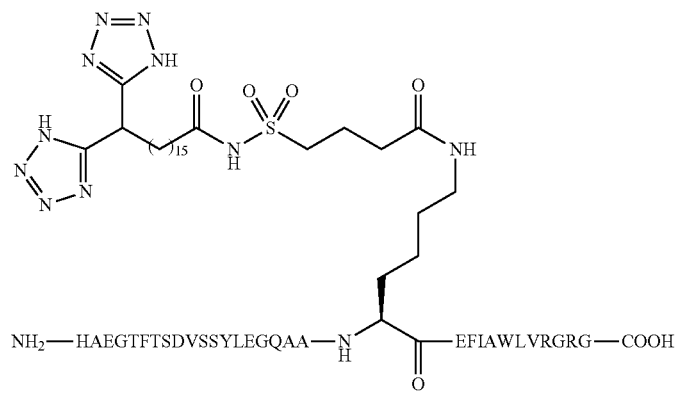

Derivative of SEQ ID NO: 19:
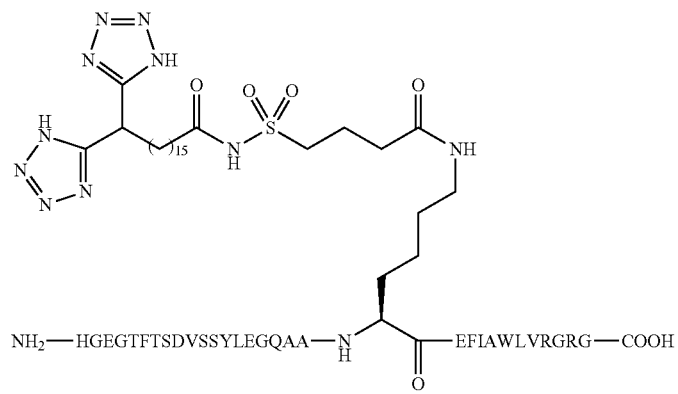
Derivative of SEQ ID NO: 7:
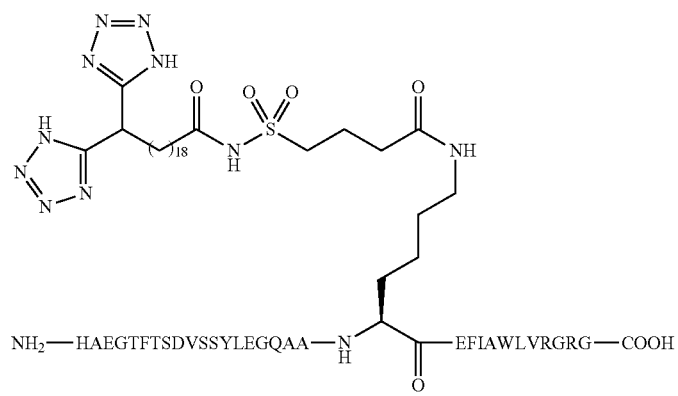
Derivative of SEQ ID NO: 7:
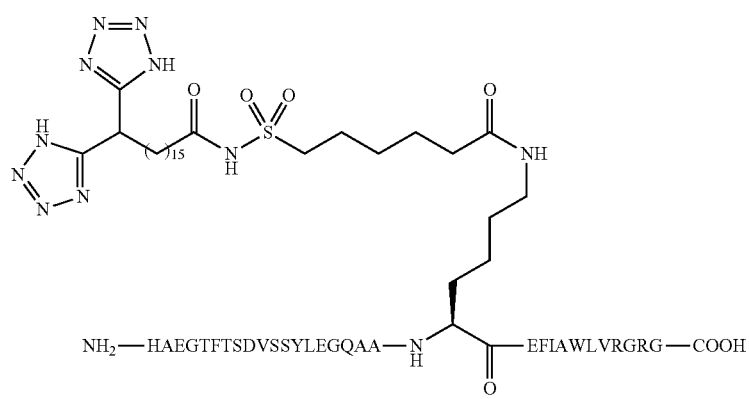

Derivative of SEQ ID NO: 19:
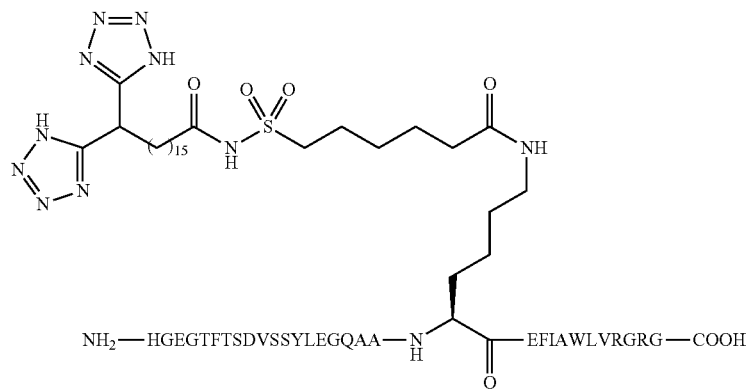
Derivative of SEQ ID NO: 7:
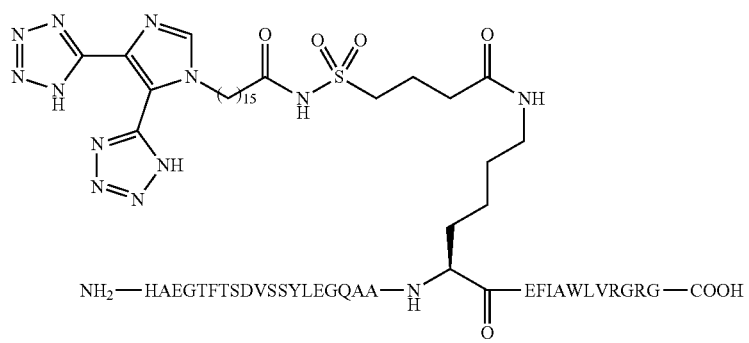
Derivative of SEQ ID NO: 19:
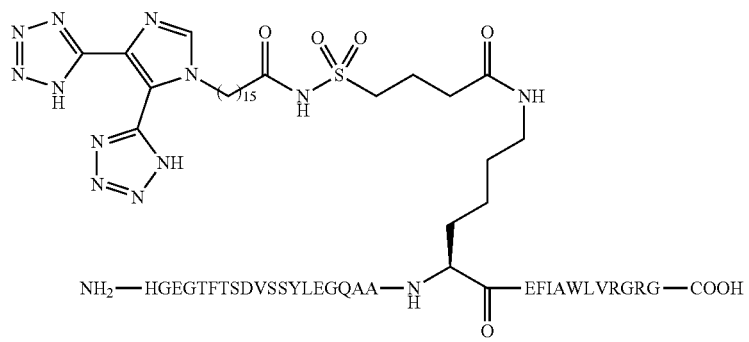

Derivative of SEQ ID NO: 7:
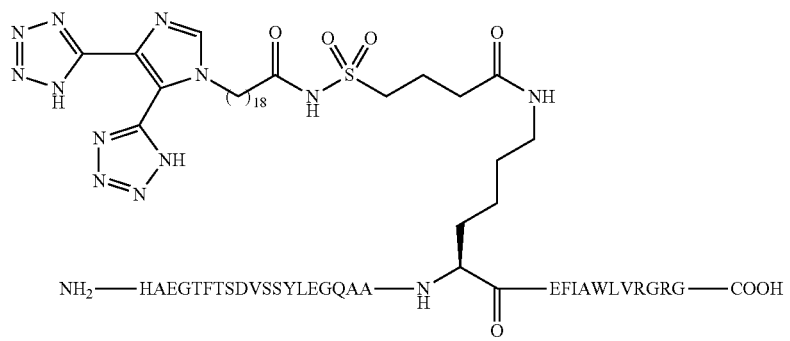
Derivative of SEQ ID NO: 7:
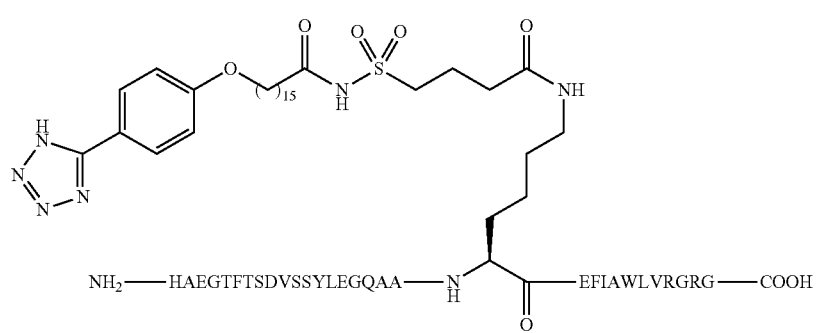
Derivative of SEQ ID NO: 7:
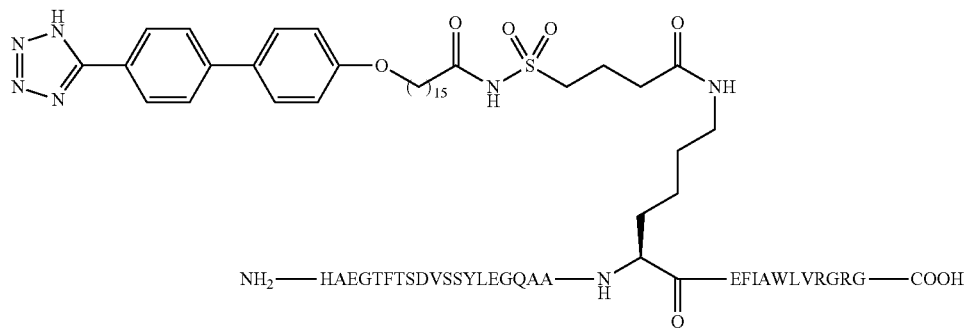
55
Derivative of SEQ ID NO: 7:
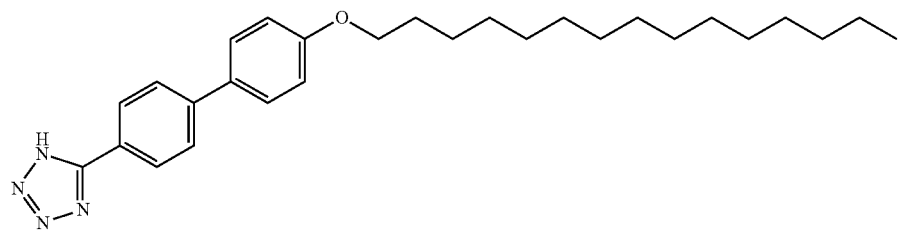

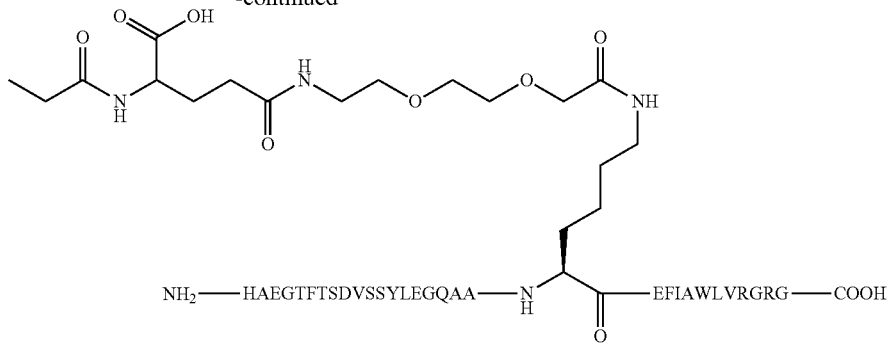
Derivative of SEQ ID NO: 7:
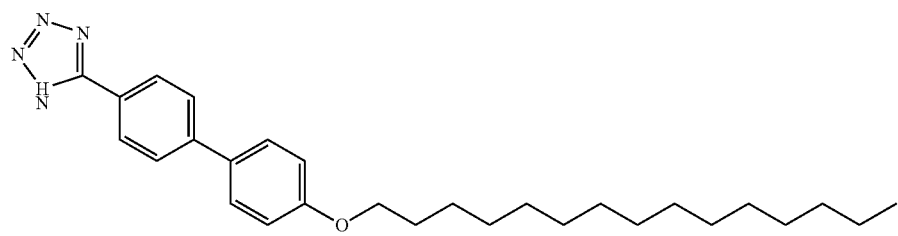
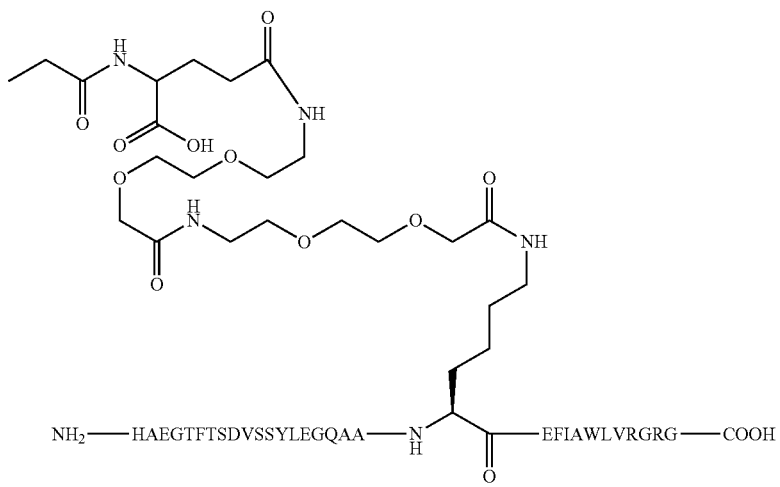
Derivative of SEQ ID NO: 18:
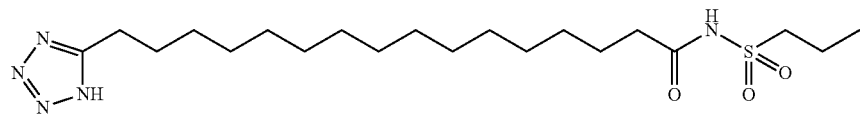

-continued
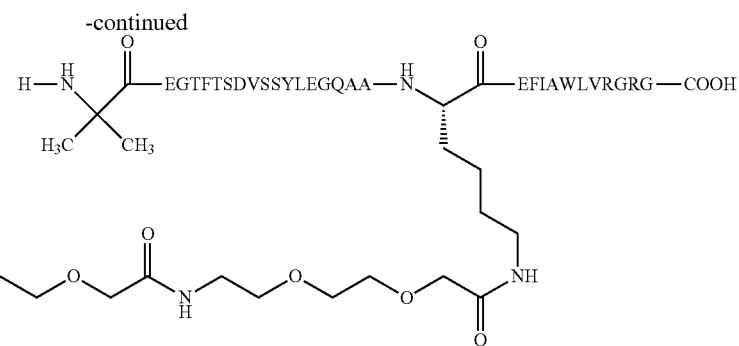
Derivative of SEQ ID NO: 18:
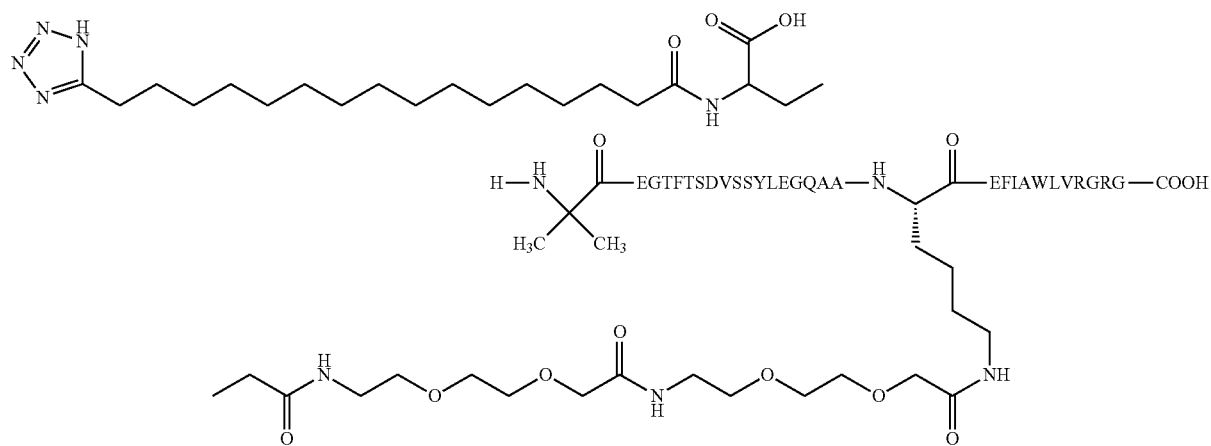
Derivative of SEQ ID NO: 18:
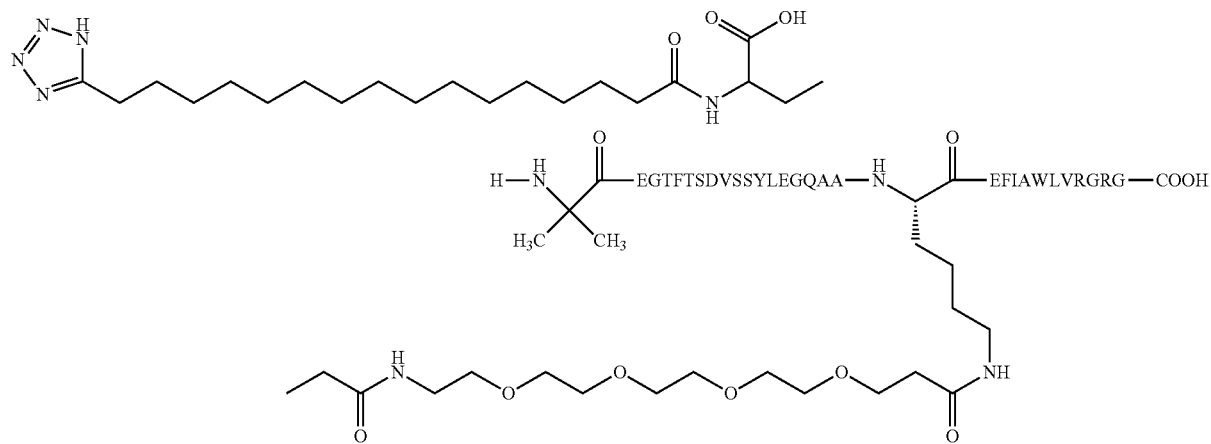
Derivative of SEQ ID NO: 18:
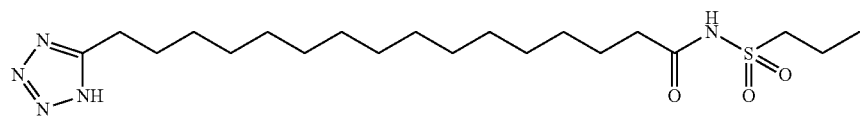

-continued

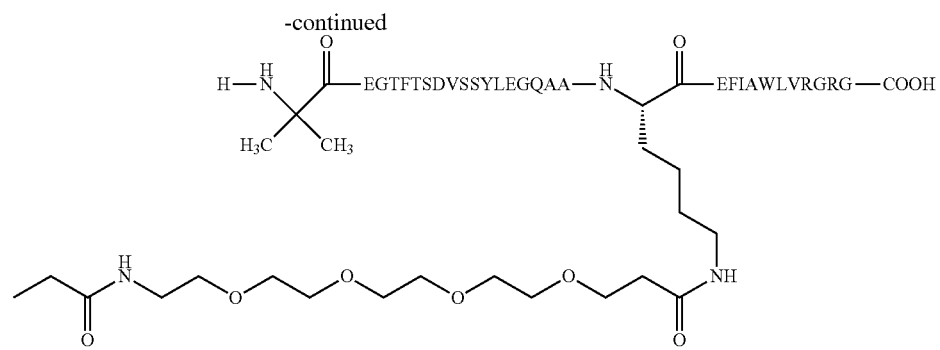

In another aspect the present invention provides a compound according to formula (I), wherein the molecule is human growth hormone or an analog thereof.

In another aspect the present invention provides a compound according to formula (I), wherein the molecule is human insulin or an analog thereof.

In another aspect the present invention provides a compound according to formula (I), wherein the molecule is factor VII or an analog thereof.

In another aspect the present invention provides a compound according to formula (I), wherein the molecule is parathyroid hormone or an analog thereof.

In another aspect the present invention provides a compound according to formula (I), wherein the molecule is human follicle stimulating hormone or an analog thereof.

In another embodiment the present invention provides a compound according to formula (I), wherein the molecule has a molar weight of less than 100 kDa, less than 50 kDa, or less than 10 kDa.

In other aspects the present invention provides a compound according to formula (I), wherein the molecule is selected from the group consisting of a growth factor such as platelet-derived growth factor (PDGF), transforming growth factor α (TGF-α), transforming growth factor β (TGF-β), epidermal growth factor (EGF), vascular endothelial growth factor (VEGF), a somatomedin such as insulin growth factor I (IGF-I), insulin growth factor II (IFG-II), erythropoietin (EPO), thrombopoietin (TPO) or angiopoietin, interferon, pro-urokinase, urokinase, tissue plasminogen activator (t-PA), plasminogen activator inhibitor 1, plasminogen activator inhibitor 2, von Willebrandt factor, a cytokine, e.g. an interleukin such as interleukin (IL) 1, IL-1Ra, IL-2, IL-4, IL-5, IL-6, IL-9, IL-11, IL-12, IL-13, IL-15, IL-16, IL-17, IL-18, IL-20 or IL-21, a colony stimulating factor (CFS) such as GM-CSF, stem cell factor, a tumor necrosis factor such as TNF-α, lymphotoxin-α, lymphotoxin-β, CD40L, or CD30L, a protease inhibitor e.g. aprotinin, an enzyme such as superoxide dismutase, asparaginase, arginase, arginine deaminase, adenosine deaminase, ribonuclease, catalase, uricase, bilirubin oxidase, trypsin, papain, alkaline phosphatase, β-glucoronidase, purine nucleoside phosphorylase or batroxobin, an opioid, e.g. endorphins, enkephalins or non-natural opioids, a hormone or neuropeptide, e.g. calcitonin, glucagon, gastrins, adrenocorticotropic hormone (ACTH), cholecystokinins, lutenizing hormone, gonadotropin-releasing hormone, chorionic gonadotropin, corticotrophin-releasing factor, vasopressin, oxytocin, antidiuretic hormones, thyroid-stimulating hormone, thyrotropin-releasing hormone, relaxin, prolactin, peptide YY, neuropeptide Y, pancreastic polypeptide, leptin, CART (cocaine and amphetamine regulated transcript), a CART related peptide, perilipin, melanocortins (melanocyte-stimulating hormones) such as MC-4, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins and analogs thereof.

In another aspect the present invention provides a compound of the general formula (II)

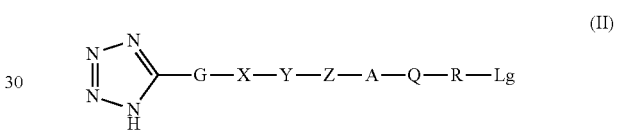

wherein G, X, Y, Z, A, Q, and R represent groups as defined in claim 3, and Lg is a leaving group, such as Cl, Br, I, OH, —OSO$_2$Me, —OSO$_2$CF$_3$, —OTs, —SMe$_2^+$, —OSu, —OBt, —OAt, —OPh, or —O(4-NO$_2$)Ph.

In another aspect the present invention provides the use of a compound according to formula (II) for the synthesis of a compound according to formula (I).

The therapeutic polypeptides can be produced by classical peptide synthesis, e.g. solid phase peptide synthesis using t-Boc or F-Moc chemistry or other well established techniques, see e.g. Green and Wuts, "Protecting Groups in Organic Synthesis", Jogn Wiley & Sons, 1999.

The therapeutic polypeptides can also be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration. For extracellular products the proteinaceous components of the supernatant are isolated by filtration, column chromatography or precipitation, e.g. microfiltration, ultrafiltration, isoelectric precipitation, purification by a variety of chromatographic procedures, e.g. ion exchange chromatography, hydrophobic interaction chromatography, gel filtration chromatography, affinity chromatography, or the like, dependent on the type of polypeptide in question. For intracellular or periplasmic products the cells isolated from the culture medium are disintegrated or permeabilised and extracted to recover the product polypeptide or precursor thereof.

The DNA sequence encoding the therapeutic polypeptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the polypeptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the polypeptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate. For large scale manufacture the selectable marker preferably is not antibiotic resistance, e.g. antibiotic resistance genes in the vector are preferably excised when the vector is used for large scale manufacture. Methods for eliminating antibiotic resistance genes from vectors are known in the art, see e.g. U.S. Pat. No. 6,358,705 which is incorporated herein by reference.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

Pharmaceutical compositions containing a compound according to the present invention may be prepared by conventional techniques, e.g. as described in Remington's *Pharmaceutical Sciences*, 1985 or in Remington: *The Science and Practice of Pharmacy*, $19^{th}$ edition, 1995.

One object of the present invention is to provide a pharmaceutical formulation comprising a compound according to the present invention which is present in a concentration from about 0.1 mg/ml to about 25 mg/ml, and wherein said formulation has a pH from 2.0 to 10.0. The formulation may further comprise a buffer system, preservative(s), isotonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 2.0 to about 10.0.

In a further aspect the invention relates to a pharmaceutical formulation comprising an aqueous solution of a compound according to the present invention, and a buffer, wherein said compound is present in a concentration from about 1 mg/ml or above, and wherein said formulation has a pH from about 7.0 to about 8.5.

In a another embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galacititol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabiliser. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e. R or S-isomers—or L, D or DL-isomer) of a particular amino acid (e.g. alanine, methionine methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used, which denotes the most abundant form of amino acids. The L-form may be an R or an S isomer dependent on the specific amino acid. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include S-ethyl homocysteine and S-butyl homocysteine and suitable cystein analogues include S-methyl-L cystein. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphur containing amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabiliser selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (e.g. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lecitins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyransoide), sphingoglycolipids (e.g. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (e.g. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quarternary ammonium bases) (e.g. cetyl-trimethylammonium bromide, cetylpyridinium chloride), nonionic surfactants (e.g. dodecyl R-D-glucopyranoside), poloxamines (e.g. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the compound, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenization, encapsulation, spray drying, microencapsulation, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the compound according to the present invention in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound according to the present invention is stable for more than 6 weeks of usage and for more than 3 years of storage.

In another embodiment of the invention the pharmaceutical formulation comprising the compound according to the present invention is stable for more than 4 weeks of usage and for more than 3 years of storage.

In a further embodiment of the invention the pharmaceutical formulation comprising the compound according to the present invention is stable for more than 4 weeks of usage and for more than two years of storage.

In an even further embodiment of the invention the pharmaceutical formulation comprising the compound is stable for more than 2 weeks of usage and for more than two years of storage.

In another aspect the present invention relates to the use of a compound according to the invention for the preparation of a medicament.

In one embodiment of the invention a compound according to the invention wherein the therapeutic agent is a GLP-1 peptide is used for the preparation of a medicament for the treatment or prevention of hyperglycemia, type 2 diabetes, impaired glucose tolerance, type 1 diabetes, obesity, hypertension, syndrome X, dyslipidemia, disorders associated with toxic hypervolemia, cognitive disorders, atheroschlerosis, myocardial infarction, coronary heart disease, stroke and other cardiovascular disorders, inflammatory bowel syndrome, dyspepsia and gastric ulcers.

In another embodiment of the invention a compound according to the invention wherein the therapeutic agent is a GLP-1 peptide is used for the preparation of a medicament for delaying or preventing disease progression in type 2 diabetes.

In another embodiment of the invention a compound according to the invention wherein the therapeutic agent is a GLP-1 peptide is used for the preparation of a medicament for decreasing food intake, decreasing β-cell apoptosis, increasing β-cell function and β-cell mass, stimulating β-cell regeneration, and/or for restoring glucose sensitivity to β-cells.

In another embodiment the present invention relates to the use of a compound according to the invention wherein the therapeutic agent is a GLP-2 peptide for the preparation of a medicament for the treatment of small bowel syndrome, inflammatory bowel syndrome or Crohns disease.

In another embodiment the present invention relates to the use of a compound according to the invention wherein the therapeutic agent is an insulin peptide for the preparation of a medicament for the treatment of hyperglycemia, type 1 diabetes, type 2 diabetes or β-cell deficiency.

The treatment with a compound according to the present invention may also be combined with combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, GLP-1 agonists, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyrotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastrin and gastrin analogs.

It should be understood that any suitable combination of the compounds according to the invention with one or more of the above-mentioned compounds and optionally one or more further pharmacologically active substances are considered to be within the scope of the present invention.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

In the examples the following terms are intended to have the following, general meanings:
Boc: tert-butyloxycarbonyl
Bt: 1-benzotriazolyl
DBU: 1,8-diazabicyclo[5.4.0]undec-7-ene
DCM: dichloromethane, methylenechloride
Dde: 1-(4,4-dimethyl-2,6-dioxocyclohexylidene)ethyl
DIC: diisopropylcarbodiimide
DMA: N,N-dimethylacetamide
DMF: N,N-dimethyl formamide
DMSO: dimethyl sulfoxide
DMAP: 4-dimethylaminopyridine
DMPU: 1,3-dimethyltetrahydropyrimidin-2-one
EDC or EDAC N-ethyl-N'-(3-dimethylaminopropyl)carbodiimide hydrochloride
Fmoc: 9-fluorenylmethyloxycarbonyl
HBTU: 2-(1H-Benzotriazol-1-yl-)-1,1,3,3 tetramethyluronium hexafluorophosphate
HOAt: 3-hydroxy-3H-[1,2,3]triazolo[4,5-b]pyridine, 4-aza-3-hydroxybenzotriazole
HOBt: N-hydroxybenzotriazole, 1-hydroxybenzotriazole
HONSu: N-hydroxysuccinimide
NMP: N-methylpyrrolidone
HPLC: high pressure liquid chromatography
Pmc 2,2,5,7,8-pentamethylchroman-6-sulfonyl
r.t. room temperature
Su: succinimidyl
TIS triisopropylsilane
Trt: trityl, triphenylmethyl
Ts: toluenesulfonyl
TSTU O-(1-succinimidyl)-N,N,N',N'-tetramethyluronium hexafluorophosphate
DIEA diisopropylethylamine
H₂O water
CH₃CN acetonitrile
OtBu tert butyl ester
tBu tert butyl
Trt triphenylmethyl
Pmc 2,2,5,7,8-Pentamethyl-chroman-6-sulfonyl
Dde 1-(4,4-Dimethyl-2,6-dioxocyclohexylidene)ethyl
DCM dichloromethane
TFA: trifluoroacetic acid
Et₂O: diethylether NMR spectra were recorded on Bruker 300 MHz and 400 MHz instruments. HPLC-MS was performed on a Perkin Elmer instrument (API 100).

HPLC-systems from Merck-Hitachi (Hibar™ RT 250-4, Lichrosorb™ RP 18, 5.0 µm, 4.0×250 mm, gradient elution, 20% to 80% acetonitrile in water within 30 min, 1.0 ml/min, detection at 254 nm) and Waters (Symmetry™, C18, 3.5 µm, 3.0×150 mm, gradient elution, 5% to 90% acetonitrile in water within 15 min, 1.0 ml/min, detection at 214 nm) were used.

Furthermore, where stated the following HPLC method h8 was used:

The reverse phase analysis was performed using UV detections at 214, 254, 276 and 301 nm on a 218TP54 4.6 mm×150 mm C-18 silica column, which was eluted at 1 ml/min at 42° C. The column was equilibrated with 5% acetonitrile, 85% water and 10% of a solution of 0.5% trifluoroacetic acid in water and eluted by a linear gradient from 5% acetonitrile, 85% water and 10% of a solution of 0.5% trifluoroacetic acid to 90% acetonitrile and 10% of a solution of 0.5% trifluoroacetic acid over 15 min.

Furthermore, where stated the following HPLC method A was used:

The RP-analysis was performed using a Waters 2690 systems fitted with a Waters 996 diode array detector. UV detections were collected at 214, 254, 276, and 301 nm on a 218TP54 4.6 mm×250 mm 5µC-18 silica column (The Seperations Group, Hesperia), which was eluted at 1 ml/min at 42° C. The column was equilibrated with 5% acetonitrile (+0.1% TFA) in an aqueous solution of TFA in water (0.1%). After injection, the sample was eluted by a gradient of 0% to 90% acetonitrile (+0.1% TFA) in an aqueous solution of TFA in water (0.1%) during 50 min.

General Procedure (A)

The compounds of formula (I) according to the invention may be prepared by the general procedure (A):

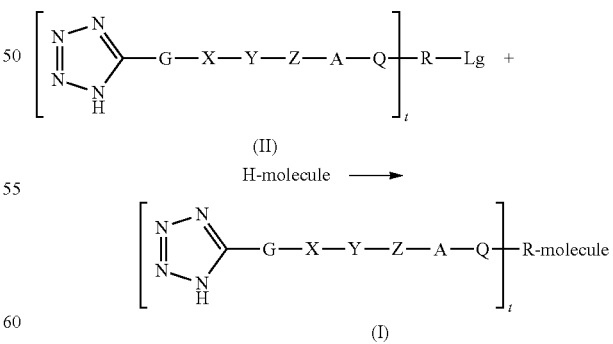

A molecule of which a prolonged half-life in plasma is required and which contains at least one acylable amino group is dissolved in a suitable solvent (water, alcohols, DMF, DMSO, DMPU, or mixtures thereof) and a solution or suspension of (II) in DMF or DMSO is added. The mixture is stirred at room temperature and the progress of the reaction is followed by HPLC. If the reaction proceeds too slowly catalytic amounts of DMAP may be added. The product is isolated by preparative HPLC of the whole reaction mixture.

General Procedure (B)

The compounds of formula (II) according to the invention may be prepared by the general procedure (B):

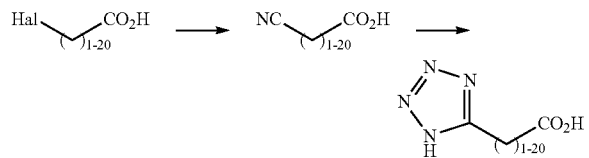

A ω-haloalkanoic acid or ester is treated with a slight excess of NaCN or KCN in a suitable solvent, such as DMF, DMSO, acetone, or an alcohol until complete conversion to the nitrile has taken place. The reaction is followed by analyzing samples by 1H NMR. The resulting ω-cyanoalkanoic acid or ester is isolated by dilution with water and extraction with AcOEt or DCM. Treatment of this ω-cyanoalkanoic acid or ester with NaN3 in the presence of AcOH and NEt$_3$ in DMF at 140° C. until all the starting material is consumed (as determined by $^1$H NMR) yields the corresponding ω-(5-tetrazolyl)alkanoic acid or ester. In the case of the ester, it is converted to the acid by treatment with an excess of NaOH or KOH in a mixture of water and an alcohol. Evaporation of the alcohol and addition of dilute aqueous HCl yields the ω-(5-tetrazolyl)alkanoic acid, which can be isolated by filtration.

Alternatively, the general procedure (B) may also be conducted with an ω-halo alkanoic ester instead of an acid. Saponification of the resulting ω-(tetrazol-5-yl)alkanoic ester to the corresponding acid can be performed by treatment with an excess KOH or NaOH in a mixture of water and ethanol.

General Procedure (C)

The compounds of formula (II) according to the invention may also be prepared by the general procedure (C):

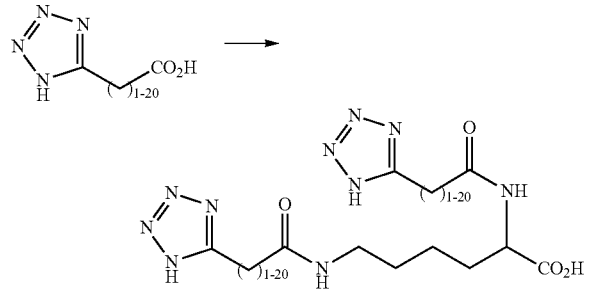

An ω-(5-tetrazolyl)alkanoic acid is converted into an acyl halide or N-hydroxysuccinimidyl ester, and then coupled to lysine methyl ester. Saponification of the resulting product yields N,N'-bis(ω-(5-tetrazolyl)alkanoyl)lysine.

General Procedure (D)

The compounds of formula (II) according to the invention may also be prepared by the general procedure (D):

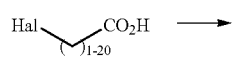

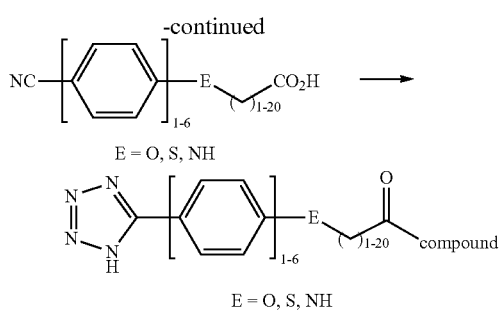

A ω-haloalkanoic acid or ester is treated with a cyanophenol, cyanothiophenol, dicyanophenol, cyanobiphenylol, cyanoterphenylol, cyanoaniline, cyanohydroxyheteroarene, or a related reagent containing at least one cyano group and one arene- or heteroarene-bound hydroxyl group in the presence of a base such as $K_2CO_3$ or DBU in a suitable solvent, such as DMF, DMSO, acetone, or an alcohol until complete conversion to the aryl or heteroarylether, -thioether, or -amine has taken place. The reaction is followed by analyzing samples by 1H NMR. The resulting ω-aryloxy-, ω-arylthio-, or ω-arylaminoalkanoic acid or ester is isolated by dilution with water and extraction with AcOEt or DCM. Treatment of this product with $NaN_3$ in the presence of AcOH and $NEt_3$ in DMF at 140° C. until all the starting material is consumed (as determined by $^1$H NMR) yields the corresponding ω-(5-tetrazolyl)aryloxy-, ω-(5-tetrazolyl)arylthio-, or ω-(5-tetrazolyl)arylaminoalkanoic acid or ester. In the case of the ester, it is converted to the acid by treatment with an excess of NaOH or KOH in a mixture of water and an alcohol. Evaporation of the alcohol and addition of dilute aqueous HCl yields the ω-(5-tetrazolyl)aryl functionalized alkanoic acid, which can be isolated by filtration.

General Procedure (E)

The compounds of formula (II) according to the invention may also be prepared by the general procedure (E):

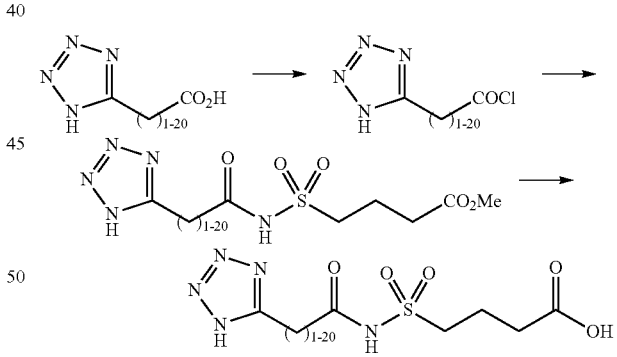

An ω-(5-tetrazolyl)alkanoic or related acid is converted into an acyl halide, and then treated with 4-(sulfamoyl)butyric acid methyl ester and DMAP in a suitable solvent, such as DCM or DCE. The resulting 4-(N-(ω-(5-tetrazolyl)alkanoyl)sulfamoyl)butyric acid methyl ester is saponified to the corresponding acid by treatment with an excess of KOH or NaOH in a mixture of water and methanol.

General procedure (F): Solid phase synthesis, purification and characterization of peptides and derivatized peptides:

The peptides were synthesized on Fmoc protected Rink amide resin (Novabiochem), Fmoc protected Wang resin or chlorotrityl resin using Fmoc strategy on an Applied Biosystems 433A peptide synthesizer in 0.25 mmol scale using the manufacturer supplied FastMoc UV protocols which employ HBTU mediated couplings in NMP and UV monitoring of the deprotection of the Fmoc protection group. The protected amino acid derivatives used were standard Fmoc-amino acids (Anaspec) supplied in preweighed cartridges suitable for the ABI 433A synthesizer with the exception of unnatural amino acids such as Fmoc-Aib-OH (Fmoc-aminoisobutyric acid).

The attachment of sidechains and linkers to specific lysine residues on the crude resin bound protected peptide was carried out in a specific position by incorporation of Fmoc-Lys (Dde)-OH during automated synthesis followed by selective deprotection with hydrazine.

Procedure for removal of Dde-protection. The resin (0.25 mmol) was placed in a manual shaker/filtration apparatus and treated with 2% hydrazine in NMP (20 ml, 2×12 min) to remove the DDE group and wash with NMP (4×20 ml).

Procedure for attachment of sidechains to Lysine residues.

The amino acid (4 molar equivalents relative to resin) was dissolved in NMP (10 ml). HOBt (4 molar equivalents relative to resin) and diisopropylcarbodiimide (4 molar equivalents relative to resin) were added and the solution was stirred for 15 min. The solution was added to the resin and DIPEA (4 molar equivalents relative to resin) was added. The resin was shaken 24 hours at room temperature. The resin was washed with NMP (2×20 ml), NMR/DCM (1:1; 2×20 ml) and DCM (2×20 ml).

Procedure for removal of Fmoc-protection: The resin (0.25 mmol) was placed in a filter flask in a manual shaking apparatus and treated with NMP/DCM (1:1) (2×20 ml) and with NMP (20 ml), a solution of 20% piperidine in NMP (3×20 ml, 10 min each). The resin was washed with NMP (2×20 ml), NMP/DCM (1:1) (2×20 ml) and DCM (2×20 ml).

Procedure for cleaving the peptide from the resin:

The peptide was cleaved from the resin by stirring for 180 min at room temperature with a mixture of TFA, water and triisopropylsilane (95:2.5:2.5). The cleavage mixture was filtered and the filtrate was concentrated to an oil by a stream of nitrogen. The crude peptide was precipitated from this oil with 45 ml diethyl ether and washed 3 times with 45 ml diethyl ether.

Purification: The crude peptide was purified by semi-preparative HPLC on a 25 mm×250 mm column packed with 5µ C-18 silica.

After drying the crude peptide was dissolved in 5 ml 50% acetic acid H2O and diluted to 20 ml with H2O and injected on the column which then was eluted with a gradient of 40-60% CH3CN in 0.1% TFA 10 ml/min during 50 min at 40° C. The peptide containing fractions were collected. The purified peptide was lyophilized after dilution of the eluate with water. The final product obtained was characterised by analytical RP-HPLC (retention time) and by LCMS The RP-HPLC analysis was performed using UV detection at 214 nm and a Vydac 218TP54 4.6 mm×250 mm 5µ C-18 silica column (The Separations Group, Hesperia, USA) which was eluted at 1 ml/min at 42° C. Two different elution conditions were used:

A1: Equilibration of the column with in a buffer consisting of 0.1 M (NH4)2SO4, which was adjusted to pH 2.5 with concentrated H2SO4 and elution by a gradient of 0% to 60% CH3CN in the same buffer during 50 min.

B1: Equilibration of the column with 0.1% TFA/H2O and elution by a gradient of 0% CH3CN/0.1% TFA/H2O to 60% CH3CN/0.1% TFA/H2O during 50 min.

B6: Equilibration of the column with 0.1% TFA/H2O and elution by a gradient of 0% CH3CN/0.1% TFA/H2O to 90% CH3CN/0.1% TFA/H2O during 50 min.

LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detector controlled by HP Chemstation software. The HPLC pump is connected to two eluent reservoirs containing:

A: 10 mM NH4OH in water
B: 10 mM NH4OH in 90% acetonitrile

The analysis was performed at 23° C. by injecting an appropriate volume of the sample (preferably 20 µl) onto the column which is eluted with a gradient of A and B. The HPLC conditions, detector settings and mass spectrometer settings used are giving in the following table.

| Column: | Waters Xterra MS C-18 × 3 mm id 5 µm |
|---|---|
| Gradient: | 5%-100% acetonitrile linear during 6.5 min at 1.5 ml/min |
| Detection: | 210 nm (analogue output from DAD) |
| ELS: | analogue output from ELS |
| MS | ionisation mode API-ES. Scan 100-1000 amu step 0.1 amu |

Typical Procedure:

A resin (Fmoc-Gly-Wang resin, 0.6 mmol/g Novabiochem 0.25 mmole) was used to produce the primary sequence on an ABI 433A machine according to manufacturers guidelines. The resin (0.25 mmole) was placed in a manual shaker/filtration apparatus and treated with 2% hydrazine in NMP in (2×12 min. 2×20 ml) to remove the Dde group. The resin was washed with NMP (4×20 ml). Fmoc-8-amino-3,6-dioxaoctanoic acid (Neosystem FA03202) (4 molar equivalents relative to resin) was dissolved in NMP/DCM (1:1, 20 ml). HOBt (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 24 hours at room temperature. The resin was washed with NMP (4×20 ml). A solution of 20% piperidine in NMP (3×20 ml, 10 min each) was added to the resin while shaking. The resin was washed with NMP (4×20 ml). 16-(Tetrazol-5-yl)hexadecanoyl-ONSu ester (4 molar equivalents relative to resin) was dissolved in NMP (20 ml). The solution was added to the resin and DIPEA (4 molar equivalents relative to resin) was added. The resin was shaken 24 hours at room temperature. The resin was washed with NMP (2×20 ml), NMP/DCM (1:1) (2×20 ml) and DCM (2×20 ml). The peptide was cleaved from the resin by stirring for 180 min at room temperature with a mixture of TFA, water and triisopropylsilane (95:2.5:2.5; 15 ml). The cleavage mixture was filtered and the filtrate was concentrated to an oil in vacuum. The crude peptide was precipitated from this oil with 45 ml diethyl ether and washed 3 times with 45 ml diethyl ether. The crude peptide was purified by preparative HPLC on a 20 mm×250 mm column packed with 7µ C-18 silica. The crude peptide was dissolved in 5 ml 50% acetic acid in water and diluted to 20 ml with H2O and injected on the column which then was eluted with a gradient of 40-60% (CH3CN in water with 0.1% TFA) 10 ml/min during 50 min at 40° C. The peptide containing fractions were collected. The purified peptide was lyophilized after dilution of the eluate with water.

Radioligand Binding to Plasma Membranes Expressing the Human GLP-1 Receptor

The binding assay was performed with purified plasma membranes containing the human GLP-1 receptor. The plasma membranes containing the receptors were purified from stably expressing BHK tk-ts 13 cells. The membranes were diluted in Assay Buffer (50 mM HEPES, 5 mM EGTA, 5 mM $MgCl_2$, 0.005% Tween 20, pH=7.4) to a final concentration of 0.2 mg/ml of protein and distributed to 96-well microtiter plates precoated with 0.3% PEI. Membranes in the presence of 0.05 nM [$^{125}$I]GLP-1, unlabelled ligands in increasing concentrations and different HSA concentrations (0.005%, 0.05%, and 2%) were incubated 2 hr at 30° C. After incubation, unbound ligands were separated from bound ligands by filtration through a vacuum-manifold followed by 2×100 μl washing with ice cold assay buffer. The filters were dried overnight at RT, punched out and quantified in a γ-counter.

Example 1

16-(5-tetrazolyl)hexadecanoic acid

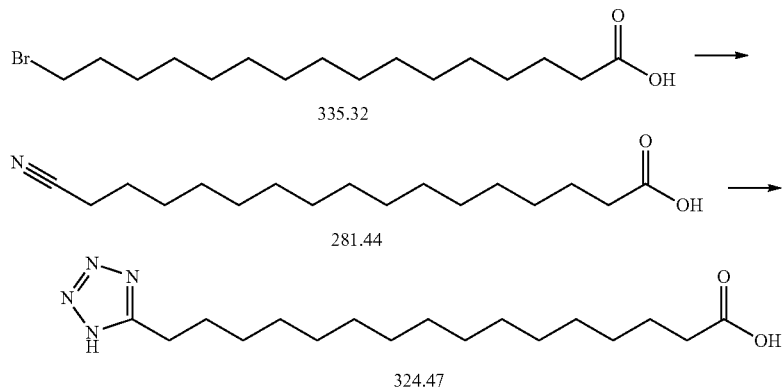

A mixture of 16-bromohexadecanoic acid (16.61 g, 49.5 mmol), DMSO (150 ml), NaCN (12.5 g, 255 mmol), and NaI (1.92 g, 12.8 mmol) was stirred at 120° C. for 20 h. The mixture was allowed to cool to room temperature, and was then poured into a stirred mixture of water (1.7 l) and concentrated HCl (30 ml). Rinsing with water (100 ml). The resulting suspension was stirred at room temperature overnight. The product was filtered and washed with water (2×100 ml), and the solid was recrystallized twice from MeCN (90 ml and 50 ml). 10.1 g (72%) of 16-cyanohexadecanoic acid was obtained.

$^1$H NMR (DMSO) δ 1.20-1.39 (m, 22H), 1.50 (m, 4H), 2.18 (t, J=7 Hz, 2H), 2.48 (t, J=7 Hz, 2H), 11.95 (s, 1H).

This product was mixed with DMF (150 ml), AcOH (10.0 ml, 174.8 mmol), $NEt_3$ (25 ml, 180 mmol), and $NaN_3$ (11.83 g, 182 mmol), and the mixture was stirred at 120° C. for 80 h, while following the conversion by $^1$H NMR. The mixture was concentrated under reduced pressure, and to the residue water (250 ml) and concentrated HCl (25 ml) were added. The acidic mixture was stirred at room temperature for 2 d, filtered, and the solid recrystallized from MeCN (approx 300 ml). 7.60 g (65%) of the title compound was obtained.

$^1$H NMR (DMSO) δ 1.24 (m, 22H), 1.48 (m, 2H), 1.68 (m, 2H), 2.18 (t, J=7 Hz, 2H), 2.84 (t, J=7 Hz, 2H), 11.95 (s, 1H).

Example 2

4-(N-(16-(5-tetrazolyl)hexadecanoyl)sulfamoyl)butyric acid

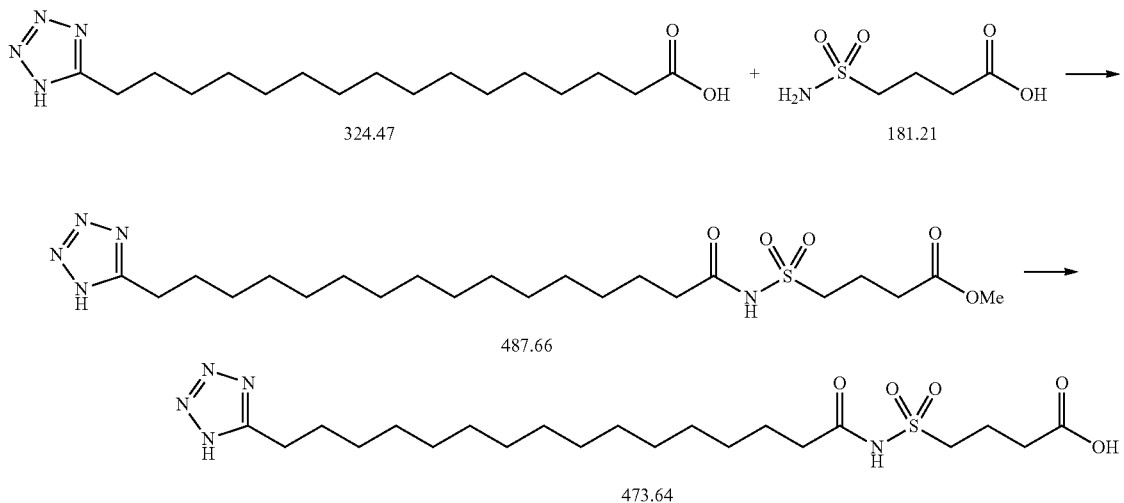

To a suspension of 16-(5-tetrazolyl)hexadecanoic acid (3.25 g, 10.0 mmol) in DCM (40 ml) was added oxalyl chloride (1.2 ml, 14.0 mmol). The mixture was stirred at room temperature for 42 h, concentrated, coevaporated once with PhMe, and to the residue were added a solution of methyl 4-sulfamoyl butyrate (1.66 g, 9.16 mmol) in DCM (35 ml) and then DMAP (3.67 g, 30.0 mmol). The heterogenous mixture was stirred at room temperature for 6.5 h and then concentrated. To the residue was added a mixture of water (50 ml) and 1N HCl (50 ml), and the resulting mixture was stirred at room temperature for 5 d. The product was filtered, washed with water (100 ml), and recrystallized from MeCN (25 ml), to yield 1.84 g (41%) of the N-acylsulfonamide methyl ester. To this ester (1.06 g, 2.17 mmol) in MeOH (15 ml) was added a solution of NaOH (0.38 g, 9.5 mmol, 4.4 eq) in water (1.5 ml). After stirring at room temperature for 1.5 h the mixture was poured into a mixture of water (80 ml) and 1N HCl (20 ml). The mixture was stirred for 3 h, filtered, and the product was dried under reduced pressure. 1.09 g (100%) of the title compound was obtained.

1H NMR (DMSO) δ 1.24 (m, 20H), 1.49 (m, 4H), 1.69 (m, 2H), 1.85 (m, 2H), 2.27 (t, J=7 Hz, 2H), 2.39 (t, J=7 Hz, 2H), 2.86 (t, J=7 Hz, 2H), 3.38 (m, 2H), 11.59 (s, 1H).

Example 3

16-(4'-(5-tetrazolyl)biphenyl-4-yloxy)hexadecanoic acid

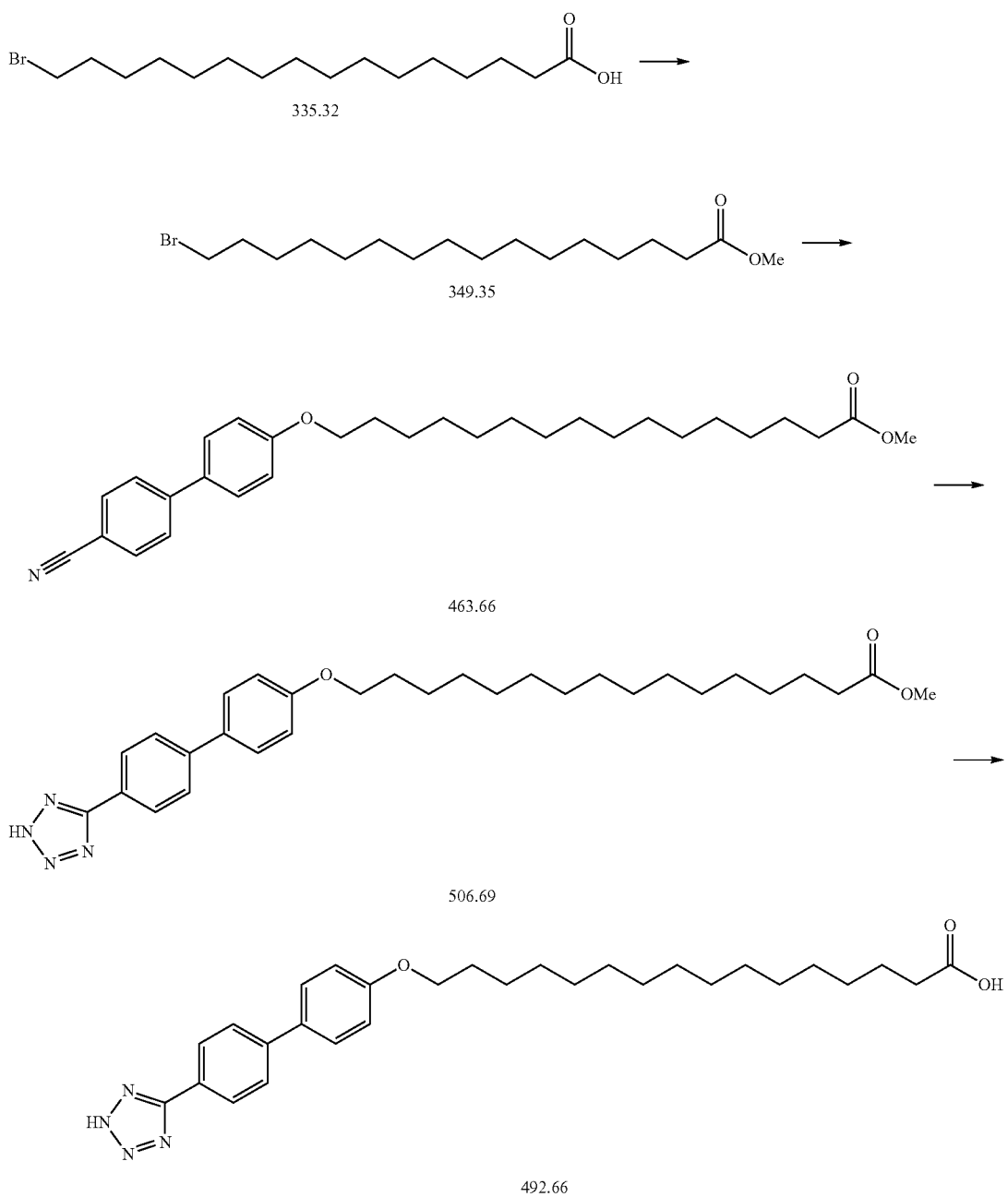

16-Bromohexadecanoic acid methyl ester

A mixture of 16-bromohexadecanoic acid (15.5 g, 46.2 mmol), MeOH (100 ml), PhMe (30 ml), trimethylorthoformate (30 ml), and polystyrene-bound benzenesulfonic acid (3.6 g) was stirred at 55° C. After 69 h the mixture was filtered through celite and the filtrate was concentrated to yield 16.85 g of an oil (100% yield).

(4'-Cyanobiphenyl-4-yloxy)hexadecanoic acid methyl ester

A mixture of 16-bromohexadecanoic acid methyl ester (4.86 g, 13.9 mmol), MeCN (20 ml), 4-cyano-4'-hydroxybiphenyl (3.16 g, 16.2 mmol), and $K_2CO_3$ (2.45 g, 17.7 mmol) was stirred at 82° C. After 17 h satd aqueous $NaHCO_3$ (150 ml) was added, and the product was filtered, washed with water, and recrystallized from boiling MeCN (approx 80 ml). Filtration and drying under reduced pressure yielded 5.40 g (84%) of (4'-cyanobiphenyl-4-yloxy)hexadecanoic acid methyl ester colorless needles.

16-(4'-(5-Tetrazolyl)biphenyl-4-yloxy)hexadecanoic acid methyl ester

A mixture of (4'-cyanobiphenyl-4-yloxy)hexadecanoic acid methyl ester (2.75 g, 5.93 mmol), DMF (7.0 ml), $NEt_3$ (4.0 ml, 28.9 mmol), AcOH (1.75 ml, 29.1 mmol), and $NaN_3$ (2.50 g, 38.5 mmol) was stirred at 140° C. After 17 h water (50 ml) and 1N HCl (50 ml) were added, followed by acidification with conc. HCl (approx 2 ml). The product was filtered and recrystallized from MeCN/PhMe (approx 60+60 ml). Filtration and drying under reduced pressure yielded 2.87 g (96%) of 16-(4'-(5-tetrazolyl)biphenyl-4-yloxy)hexadecanoic acid methyl ester.

16-(4'-(5-Tetrazolyl)biphenyl-4-yloxy)hexadecanoic acid

A mixture of 16-(4'-(5-tetrazolyl)biphenyl-4-yloxy)hexadecanoic acid methyl ester (2.87 g, 5.66 mmol), MeOH (30 ml), and a solution of NaOH (1.51 g, 37.8 mmol) in water (2.0 ml) was stirred at 70° C. After 4 d water (100 ml) and 1N HCl (50 ml) were added, and the product was filtered, washed with water, coevaporated with MeCN/PhMe, and dried under reduced pressure. 2.68 g (96%) of 16-(4'-(5-tetrazolyl)biphenyl-4-yloxy)hexadecanoic acid was obtained.

$^1$H NMR (DMSO) δ 1.20-1.50 (m, 24H), 1.72 (m, 2H), 2.18 (t, J=7 Hz, 2H), 4.02 (t, J=6 Hz, 2H), 7.04 (d, J=8 Hz, 2H), 7.71 (d, J=8 Hz, 2H), 7.87 (d, J=8 Hz, 2H), 8.09 (d, J=8 Hz, 2H), 11.95 (br s, 1H).

Example 4

4-(4-(5-Tetrazolyl)-[1,1',4',1"]-terphenyl-4"-yloxy)butyric acid

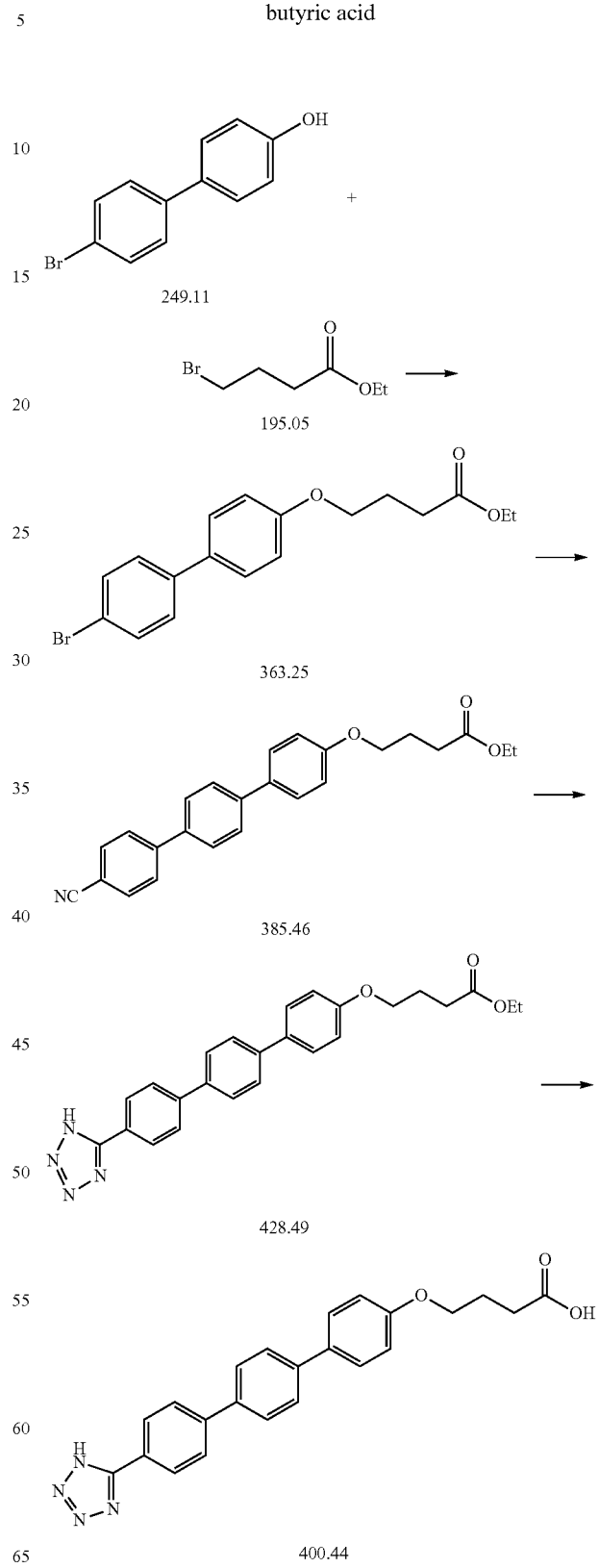

4-(4'-Bromobiphenyl-4-yloxy)butyric acid ethyl ester

A mixture of 4-(4-bromophenyl)phenol (3.74 g, 15.0 mmol), MeCN (20 ml), ethyl 4-bromobutyrate (4.42 g, 22.7 mmol), and $K_2CO_3$ (3.12 g, 22.6 mmol) was stirred at 80° C. After 16 h water (100 ml) and 1N HCl (40 ml) were added, and the product was extracted (3×AcOEt), the combined extracts were washed with brine (2×), dried ($MgSO_4$), and concentrated. The residue was recrystallized from EtOH (40 ml) to yield 4.35 g (80%) of 4-(4'-bromobiphenyl-4-yloxy) butyric acid ethyl ester as colorless plates.

4-(4-Cyano-[1,1',4',1"]-terphenyl-4"-yloxy)butyric acid ethyl ester

To 4-(4'-bromobiphenyl-4-yloxy)butyric acid ethyl ester (2.03 g, 5.59 mmol) in toluene (30 ml) and EtOH (20 ml) were added triphenylphosphine (0.17 g, 0.65 mmol), 4-cyanophenylboronic acid (1.23 g, 8.37 mmol), $Pd(OAc)_2$ (65 mg, 0.29 mmol), and a solution of $Na_2CO_3$ (2.33 g, 22.0 mmol) in water (10 ml). The mixture is stirred at 70° C. (oil-bath temperature). After 66 h water (100 ml) and 1N HCl (50 ml) were added and the product was extracted (3×DCM). The combined extracts were washed with water, then with satd. aqueous $NaHCO_3$, dried and concentrated to yield 2.33 g of a gray solid, which is washed with hot EtOH and dried under reduced pressure to yield 0.81 g (38%) of 4-(4-cyano-[1,1', 4',1"]-terphenyl-4"-yloxy)butyric acid ethyl ester. From the ethanol washings more product (0.48 g, 22%) precipitated.

4-(4-(5-Tetrazolyl)-[1,1',4',1"]-terphenyl-4"-yloxy) butyric acid ethyl ester A mixture of 4-(4-cyano-[1,1',4',1"]-terphenyl-4"-yloxy) butyric acid ethyl ester (1.29 g, 3.35 mmol), DMF (4.0 ml), $NEt_3$ (2.3 ml, 16.6 mmol), AcOH (1.0 ml, 16.7 mmol), and $NaN_3$ (1.32 g, 20.3 mmol) was stirred at 140° C. After 20 h water (50 ml) and 1N HCl (50 ml) were added and the product is isolated by filtration, washed with hot MeCN and dried under reduced pressure to yield 1.16 g (81%) of 4-(4-(5-tetrazolyl)-[1,1',4',1"]-terphenyl-4"-yloxy)butyric acid ethyl ester as a gray solid.

4-(4-(5-Tetrazolyl)-[1,1',4',1"]-terphenyl-4"-yloxy) butyric acid

A heterogenous mixture of 4-(4-(5-tetrazolyl)-[1,1',4',1"]-terphenyl-4"-yloxy)butyric acid ethyl ester (1.16 g, 2.71 mmol), EtOH (10 ml), NaOH (0.75 g, 18.8 mmol), and water (1.5 ml) was stirred at 80° C. After 18 h water (50 ml) and 1N HCl (50 ml) were added. After stirring for 0.5 h the product was filtered, washed with water, and the solid was coevaporated with MeCN and PhMe to yield 0.79 g (73%) of 4-(4-(5-tetrazolyl)[1,1',4',1"]-terphenyl-4"-yloxy)butyric acid as a light-brown powder.

1H NMR (DMSO) δ 1.98 (quint, J=7 Hz, 2H), 2.41 (t, J=7 Hz, 2H), 4.03 (t, J=7 Hz, 2H), 7.04 (d, J=8 Hz, 2H), 7.69 (d, J=8 Hz, 2H), 7.77 (d, J=8 Hz, 2H), 7.85 (d, J=8 Hz, 2H), 7.98 (d, J=8 Hz, 2H), 8.14 (d, J=8 Hz, 2H), 12.19 (br s, 1H).

Example 5

NNC 0113-0000-0090

N-ε-26-(16-[5-tetrazolyl]hexadecanoyl)Arg$^{34}$GLP-1-(7-37) (Derivative of SEQ ID NO: 7)

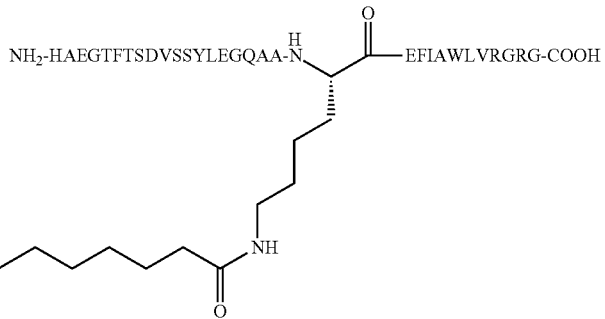

This compound was prepared by acylation with 16-[5-tetrazolyl]hexadecanoic acid (Example 1) of unprotected Arg$^{34}$GLP-1-(7-37) peptide in solution. The succinimidyl ester of 16-[5-tetrazolyl]hexadecanoic acid was prepared by mixing the acid (29 mg) with THF (0.9 ml), DIPEA (17 microliter), and TSTU (30 mg), and stirring the resulting mixture at room temperature for 1 h. Arg$^{34}$GLP-1-(7-37) (0.33 g, 30% pure) was dissolved in water (5 ml) and DIPEA (50 microliter), and the solution of the succinimidyl ester (0.3 ml) was added. After stirring at room temperature for 20 min the excess succinimidyl ester was quenched by addition of an excess glycine, and the product was purified by preparative HPLC. 38 mg of the title compound were obtained.

HPLC: (method B6): RT=9.36 min (100%)
LCMS: m/z=1231 ($MH_3^{3+}$). Calculated for ($MH_3^{3+}$): 1231

Example 6

0113-0000-0098

Gly$^8$,Arg$^{26,34}$GLP-1(7-37)Lys(16-(5-tetrazolyl)hexadecanoyl) (Derivative of SEQ ID NO: 8)

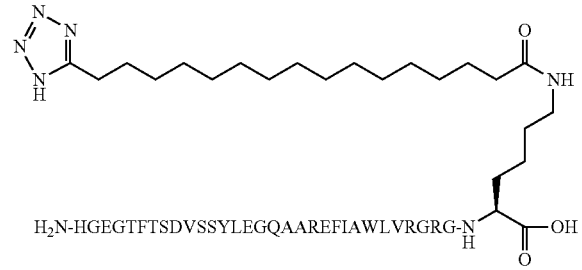

Gly⁸,Arg²⁶,³⁴GLP-1-(7-37) was prepared on a 433A peptide synthesizer using standard Fmoc-methodology and using Fmoc-Lys(Boc)-trityl polystyrene (0.88 g, loading: 0.79 mmol/g) as starting resin. After purification by preparative HPLC 25 mg of Gly⁸,Arg²⁶,³⁴GLP-1(7-37) peptide was obtained.

The title compound was prepared by acylation of Gly⁸,Arg²⁶,³⁴GLP-1(7-37) peptide (25 mg) with 16-(5-tetrazolyl)hexadecanoic acid (23 mg) as described for Example 5. 14.6 mg of the title compound were obtained.

HPLC: (method B6): RT=9.02 min (99%)
LCMS: m/z=1279 (MH$_3^{3+}$). Calculated for (MH$_3^{3+}$): 1279

Example 7

0113-0000-0099

Gly⁸,Arg²⁶,³⁴GLP-1(7-37)Lys{-4-[N-(16-{5-tetrazolyl}hexadecanoyl)sulfamoyl]butyryl}peptide (Derivative of SEQ ID NO: 8)

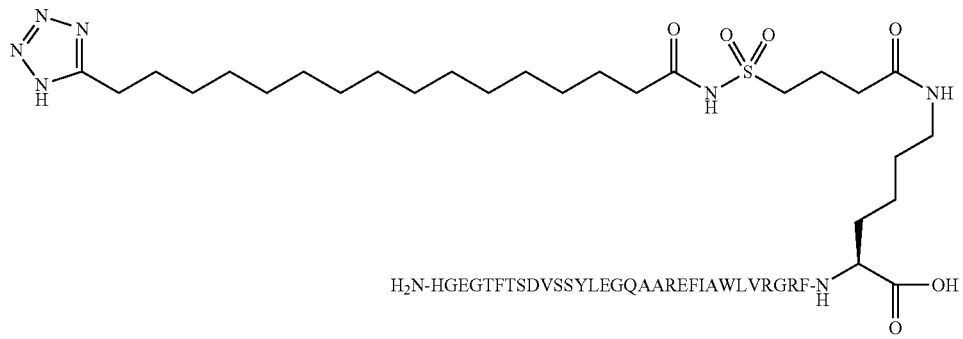

The title compound was prepared as Example 6 from {4-[N-(16-{5-tetrazolyl}hexadecanoyl)sulfamoyl]butyric acid (21 mg; Example 2) and Gly⁸,Arg²⁶,³⁴GLP-1(7-37) (25 mg). 1.5 mg of the title compound was obtained.

HPLC: (method B6): RT=9.05 min (95%)
LCMS: m/z=1328 (MH$_3^{3+}$). Calculated for (MH$_3^{3+}$): 1328

Example 8

0113-0000-0100

N-ε-26-{-4-[N-(16-{5-tetrazolyl}hexadecanoyl)sulfamoyl]butyryl}Arg³⁴GLP-1(7-37) (Derivative of SEQ ID NO: 7)

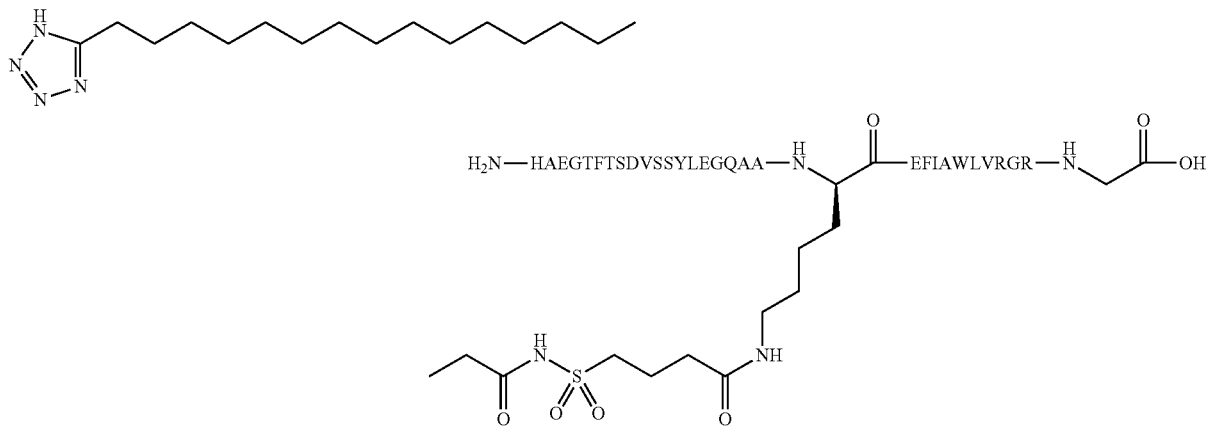

This compound was prepared as Example 5 from {-4-[N-(16-{5-tetrazolyl}hexadecanoyl)sulfamoyl]butyric acid (21 mg; Example 2) and Arg³⁴GLP-1(7-37) peptide (0.3 g, 30% pure). 10.1 mg of the title compound was obtained.

HPLC: (method B6): RT=9.35 min (94%)
LCMS: m/z=1281 (MH$_3^{3+}$). Calculated for (MH$_3^{3+}$): 1281

Example 9

NNC 0113-0075

N-ε-37-(2-(2-(2-(16-(tetrazol-5-yl)(hexadecanoy-lamino)ethoxy)ethoxy)acetyl))

Aib⁸,²²,³⁵Lys³⁷GLP-1(7-37) (Derivative of SEQ ID NO: 6)

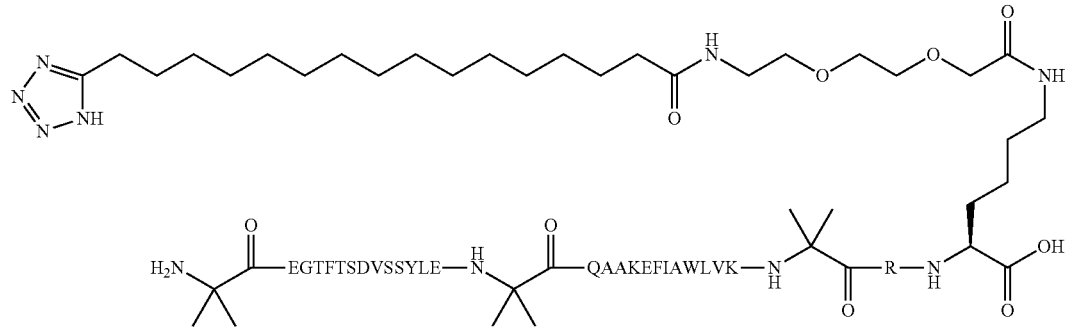

Prepared as described in the 'Typical Procedure'.

HPLC: (method B6): RT=31.8 min (98%), (method A1): RT=41.5 min

LCMS: m/z=988.7 $(MH_4)^{4+}$, 1317.8 $(MH_3)^{3+}$. Calculated $(MH)^+$: 3949.6

Example 10

Human growth hormone (100 mg, hGH) was dissolved in H₂O (6 ml), DIEA (7.5 µl), and NMP (6 ml) and cooled to 0° C. 16-(Tetrazol-5-yl)hexadecanoyl-ONSu (3.5 mg, 2 eq), dissolved in NMP (100 µl), was added. The reaction mixture was stirred for 1 h and purified by ion exchange chromatography.

Purification of monoacylated hGH in position 140 or 145.

The crude reaction mixture was diluted five times in 50 mM Tris pH 8.5 and applied to a Mono Q column. For purification of 6 ml crude reaction mixture a 10 ml 10/10 Mono Q column from Amersham Pharmcia was used. A 1000 CV gradient was used to separate the native, monoacylated in position 30/45/70, monoacylated in position 140/145, diacylated and triacylated hGH. Shortly after elution of the triacylated hGH, a steep gradient was used to elute dimeric hGH. As eluting buffer 50 mM Tris, 2 M NaCl, pH 8.5 was used. The purification was performed at 4° C.

After elution, fractions containing monoacylated hGH (peak 2) was pooled and subsequently ultrafiltrated using a Amicon with a YM10 filter. The washing buffer was 50 mM Ammoniumcarbonate pH 8.0. After ultrafiltration, the acylated protein was lyophilized.

Chromatograms depicting A280 nm and A254 nm both exhibited five distinct peaks which were characterised by peptide mapping:

Peak 1 contains native hGH
Peak 2 contains monoacylated hGH in position 38 or 45 or 70.
Peak 3 contains monoacylated hGH in position 140 or 145
Peak 4 contains diacylated hGH
Peak 5 contains triacylated hGH

Example 11

NNC 0113-0000-0134

Gly⁸,Glu²²,²³,³⁰Arg¹⁸,²⁶,³⁴ GLP-1(7-37)Lys(16-(1H-tetrazol-5-yl)hexadecanoic acid [2-(2-{[2-(2-carbam-oylmethoxyethoxy)ethylcarbamoyl]methoxy}ethoxy)ethyl]amide)-NH₂ (Derivative of SEQ ID NO: 9)

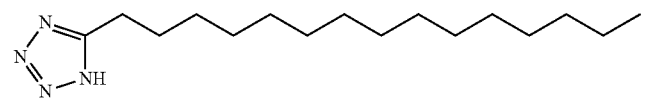

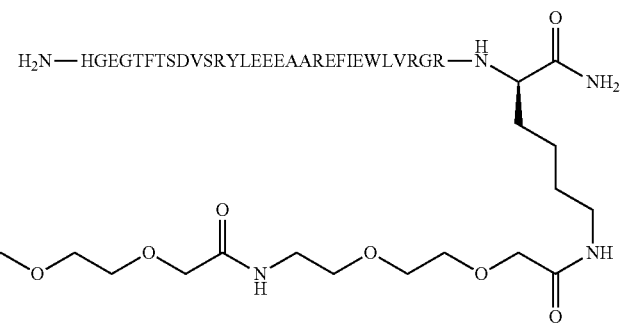

Prepared as described in the 'Typical Procedure'.
HPLC: (method B6): RT=30.283 min (96%)
LCMS: m/z=1441.8 $(MH_3)^{3+}$. Calculated $(MH_3)^{3+}$: 1439.6

Example 12

NNC 0113-0000-0140

Gly$^8$Arg$^{26,34}$GLP-1(7-37)Lys(4-(4-(4-(4-(5-tetrazolyl)phenyl)phenyl)phenoxy)butyryl)

(Derivative of SEQ ID NO: 8)

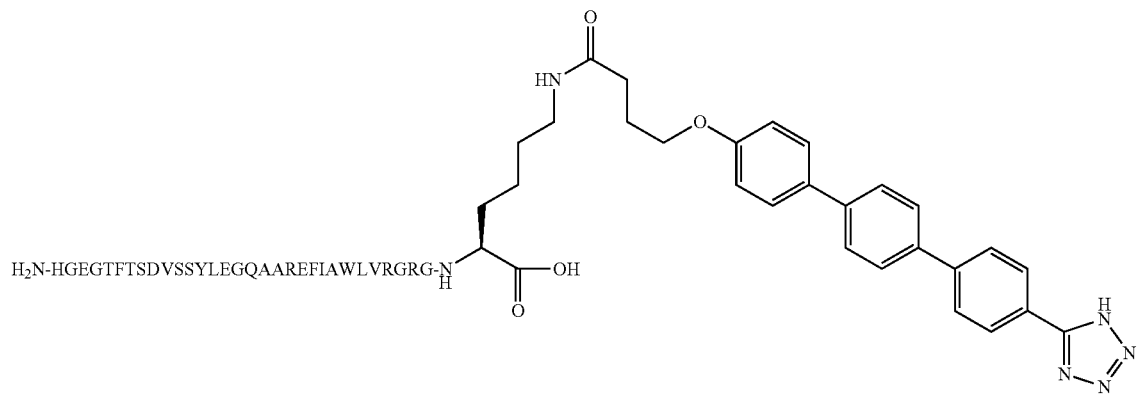

Prepared as described in the 'Typical Procedure'.
HPLC: (method B4): RT=10.89 min (100%)
LCMS: m/z=1304 $(MH_3)^{3+}$. Calculated $(MH_3)^{3+}$: 1304

N-$^{\epsilon 38}$-(2-(2-[2-(16-(4-(5-tetrazoyl)phenoxy)hexadecanoyl)ethoxy)ethoxy)acetyl)

[Gly8,Arg26,34,Lys38]GLP-1(7-37) peptide
(Derivative of SEQ ID NO: 8)

0113-0000-0160

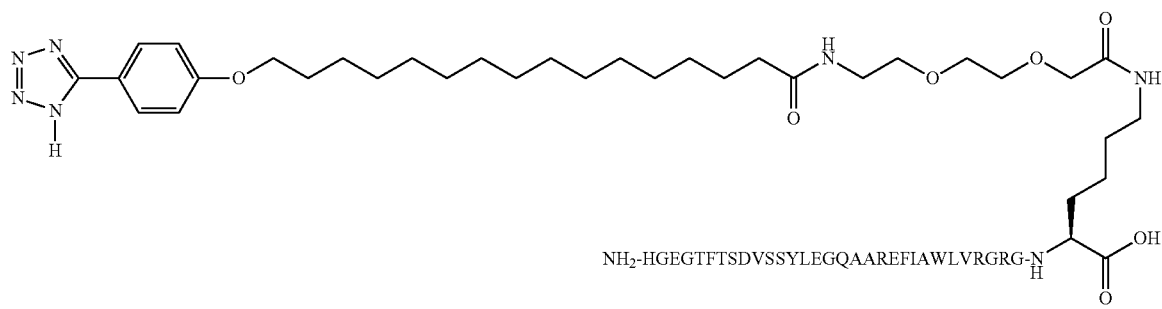

[Gly8,Arg26,34,Lys38] GLP-1-(7-37) (SEQ ID NO: 8) peptide was prepared on an Advanced Chemtech APEX 348 peptide synthesizer using standard Fmoc methodology and using 2-chlorotrityl chloride resin (0.400 g, loading: 1.4 mmol/g) as starting resin. Lys38 was protected as Fmoc-Lys (ivDde)-OH.

IvDde was removed with 3% hydrazine and 3% piperidine in NMP for 60 min. The title compound was prepared by acylation with N-Fmoc (2-(2-aminoethoxy)ethoxy)acetic acid (0.56 mmol), followed by Fmoc-group removal and acylation with 0.62 mmol of 16-(4-(5-tetrazolyl)phenoxy)hexadecanoic acid. After cleavage from the support the peptide was purified by preparative HPLC (gradient elution 0-5 min=30% MeCN, 5-40 min=30-65% MeCN; Xterra prep. Ms C18).

RT=26.1 min

Maldi: m/z=4071; Calculated: 4069.6

Example 13

N-epsilon37-(2-(2-(2-(16-(4-(5-Tetrazolyl)phenoxy)hexadecanoyl)ethoxy)ethoxy)acetyl)[Aib8,22,35,Lys37]GLP-1 (7-37)

0113-0000-0161 (Derivative of SEQ ID NO: 6)

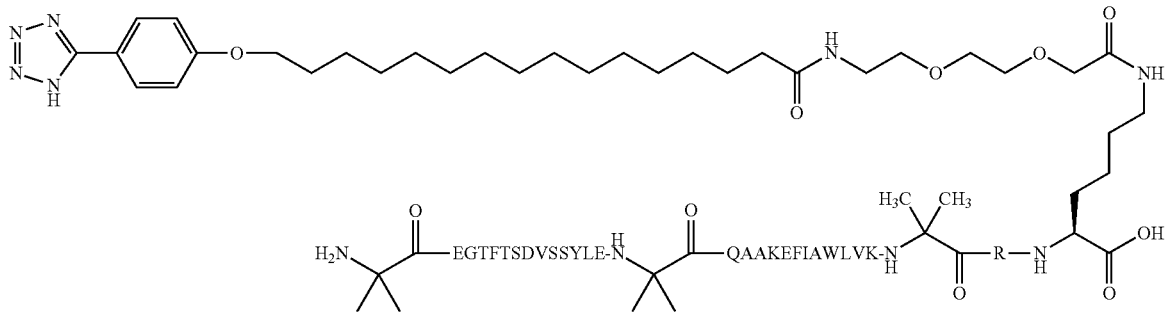

[Aib 8,22,35,Lys37] GLP-1(7-37) peptide was prepared on an Advanced ChemTech APEX 348 peptide synthesizer using standard Fmoc methodology and using 2-chlorotrityl chloride resin (0.400 g, loading: 1.4 mmol/g) as starting resin. Lys37 was protected as Fmoc-Lys(ivDde)-OH.

IvDde was removed with 3% hydrazine and 3% piperidin in NMP for 60 min. After this deprotection, the resin-bound peptide was acylated with N-Fmoc (2-(2-aminoethoxy)ethoxy)acetic acid (0.59 mmol), followed by Fmoc-group removal and acylation with 0.62 mmol of 16-(4-(5-tetrazolyl)phenoxy)hexadecanoic acid. The peptide was cleaved from the support (90% TFA, 5% Tis, 2% thioanisol, 3% water, 2 h), precipitated with Et$_2$O, lyophilized, and purified by preparative HPLC (gradient elution 0-5 min=30% MeCN, 5-40 min=30-65% MeCN; Xterra prep. Ms C18).

RT=26.85 min

Maldi: m/z=4042. Calculated: 4040.7

Example 14

N$^{\epsilon 38}$-(2-(2-(2-(16-(Tetrazol-5-yl)hexadecanoyl)ethoxy)ethoxy)acetyl)

[Aib8,Arg26,34,Lys38]GLP-1(7-37) peptide
0113-0000-0208 (Derivative of SEQ ID NO: 16)

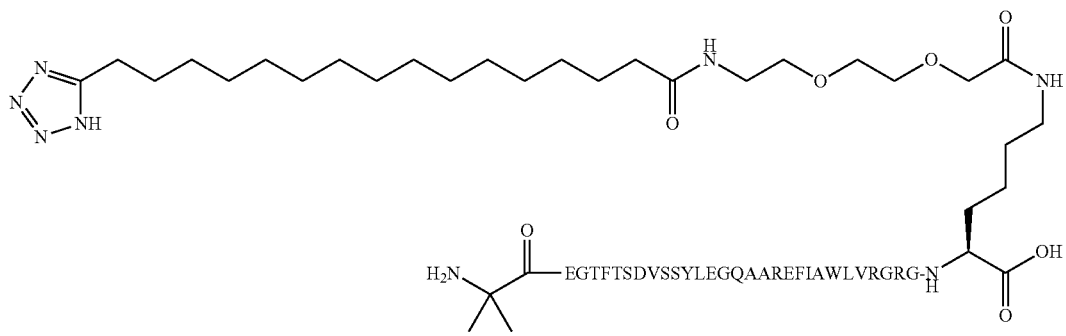

[Aib8,Arg26,34,Lys38]GLP-1(7-37) (SEQ ID NO: 16) peptide was prepared on the Advanced ChemTech APEX 348 peptide synthesizer using standard Fmoc methodology and 2-chlorotrityl chloride resin (0.150 g, loading: 1.4 mmol/g) as starting resin. Lys38 was protected as Fmoc-Lys(ivDde)-OH.

IvDde was removed with 3% hydrazine and 3% piperidin in NMP for 60 min. After this deprotection, the resin-bound peptide was acylated with N-Fmoc (2-(2-aminoethoxy)ethoxy)acetic acid (0.35 mmol), followed by Fmoc-group removal and acylation with 0.32 mmol of 16-(5-tetrazolyl)hexadecanoic acid. The peptide was cleaved from the support (90% TFA, 5% Tis, 2% thioanisol, 3% water, 2 h), precipitated with Et$_2$O, lyophilized, and purified by preparative RP-HPLC (gradient elution 0-5 min: 80% A, 20% B; 5-45 min to 40% A, 60% B; A: water+0.1% TFA; B: MeCN+0.07% TFA).

LCMS: 4005. Calculated: 4005.6

Example 15
Nε38-(4-(N-(16-(Tetrazol-5-yl)hexadecanoyl)sulfamoyl)butyryl) [Aib8,Arg26,34, Lys38]GLP-1(7-37) peptide 0113-0000-210 (Derivative of SEQ ID NO: 15)

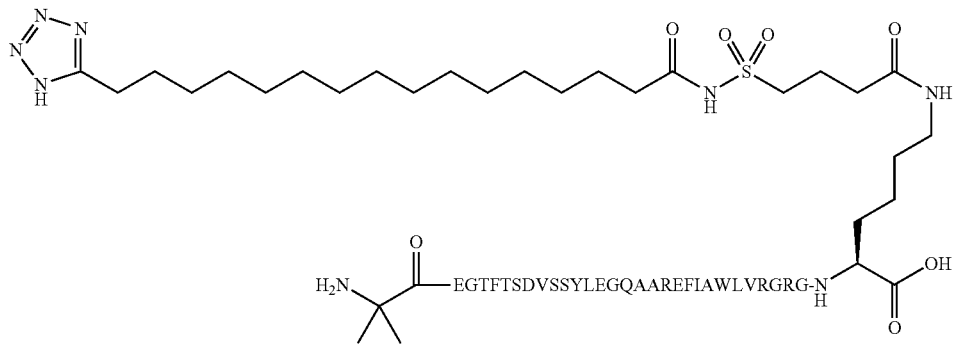

The title compound was prepared as example 6. 8 mg of the title compound was obtained.
RT: 32 min.
Maldi: m/z=4007. Calculated: 4009

Example 16

N-epsilon32-(4-[N-(16-{5-Tetrazolyl}hexadecanoyl)sulfamoyl]butyryl)-[Lys32]Exendin[1-39]peptide 0113-0000-0211 (Derivative of SEQ ID NO: 17)

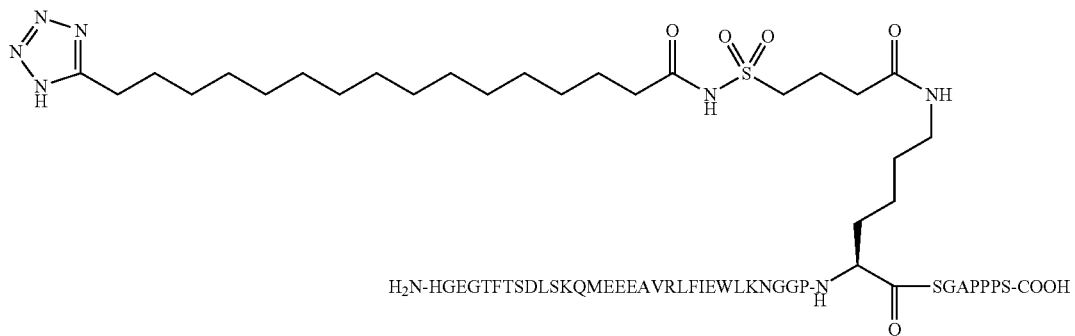

[Lys32]Exendin[1-39] (SEQ ID NO: 17) peptide was prepared on the Advanced ChemTech APEX 348 peptide synthesizer using standard Fmoc methodology and 2-chlorotrityl chloride resin (0.150 g, loading: 1.4 mmol/g) as starting resin. Lys38 was protected as Fmoc-Lys(ivDde)-OH.

IvDde protection was removed with 3% hydrazine and 3% piperidin in NMP for 60 min. After this deprotection, the resin-bound peptide was acylated with N-Fmoc (2-(2-aminoethoxy)ethoxy)acetic acid (0.35 mmol), followed by Fmoc-group removal and acylation with 0.32 mmol of 4-(16-(5-tetrazolyl)hexadecanoyl)sulfamoylbutyric acid. The peptide was cleaved from the support (90% TFA, 5% Tis, 2% thioanisol, 3% water, 2 h), precipitated with Et₂O, lyophilized, and purified by preparative RP-HPLC (gradient elution 0-5 min: 80% A, 20% B; 5-45 min to 40% A, 60% B; A: water+ 0.1% TFA; B: MeCN+0.07% TFA).

KJM eksempler

Example 17

0113-0000-0150, PrnC

N-epsilon37-(16-(4'-(Tetrazol-5-yl)biphenyl)-4-yloxy)hexadecanoyl) [3-(4-imidazolyl)propionyl7, Aib22,35,Arg26,34,Lys37]GLP-1 (7-37) peptide (Derivative of SEQ ID NO: 10)

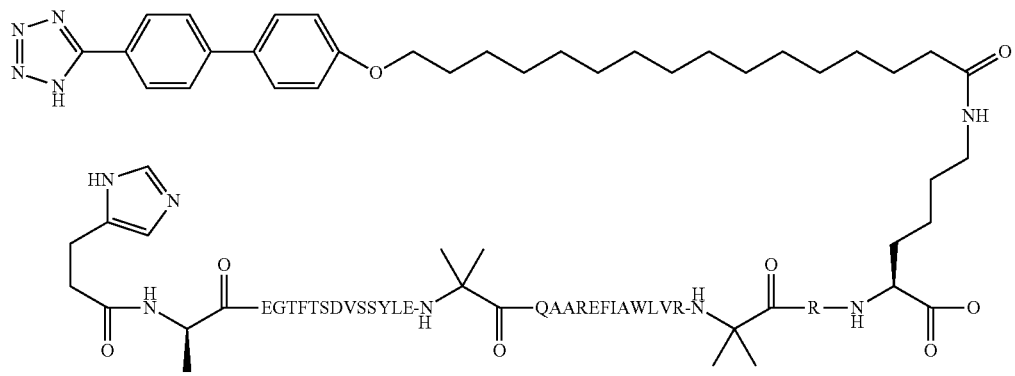

[3-(4-Imidazolyl)Propionyl7,Aib22,35,Arg26,34,Lys37] GLP-1 (7-37) peptide was prepared on a 433A peptide synthesizer using standard Fmoc-methodology and using Fmoc-Lys(Boc)-trityl polystyrene (0.51 g, loading: 0.50 mmol/g) as starting resin. After purification by preparative HPLC 159 mg of [3-(4-imidazolyl)propionyl7,Aib22,35,Arg26,34,Lys37] GLP-1 (7-37) peptide was obtained.

The title compound was prepared by acylation of [3-(4-imidazolyl)propionyl7,Aib22,35,Arg26,34,Lys37]GLP-1 (7-37) peptide (18 mg) with 16-(4'-(tetrazol-5-yl)biphenyl)-4-yloxy)hexadecanoic acid (10 mg) as described for Example 5. 4.74 mg of the title compound was obtained.

HPLC: (method B6): RT=38.4 min (97%)
LCMS: m/z=1333.7 ($MH_3^{3+}$). Calculated for ($MH_3^{3+}$): 1334.2

Example 18

0113-0000-0151, PrnC

N-epsilon37-(16-(Tetrazol-5-yl)hexadecanoyl) [3-(4-imidazolyl)propionyl7,Aib22,35,Arg26,34,Lys37] GLP-1 (7-37) (Derivative of SEQ ID NO: 10)

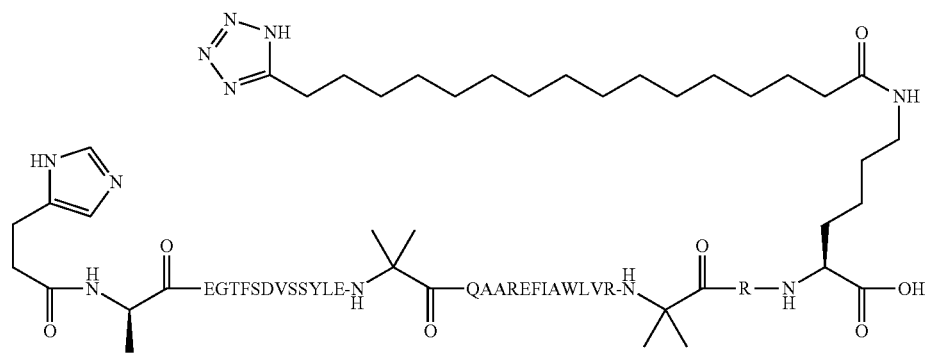

[3-(4-Imidazolyl)propionyl7,Aib22,35,Arg26,34,Lys37] GLP-1 (7-37) peptide was prepared as described in Example 17.

The title compound was prepared by acylation of [3-(4-imidazolyl)propionyl7,Aib22,35,Arg26,34,Lys37]GLP-1 (7-37) peptide (18 mg) with 16-(tetrazol-5-yl)hexadecanoic acid (8.5 mg) as described for Example 5. 7.32 mg of the title compound was obtained.

HPLC: (method B6): RT=33.0 min (100%)
LCMS: m/z=1277.9 ($MH_3^{3+}$). Calculated for ($MH_3^{3+}$): 1277.8

Example 19

0113-0000-0152, PrnC

N-epsilon37-(16-(4-(Tetrazol-5-yl)phenoxy)hexadecanoyl) [3-(4-imidazolyl)propionyl7,Aib22,35, Arg26,34,Lys37]GLP-1 (7-37) (Derivative of SEQ ID NO: 10)

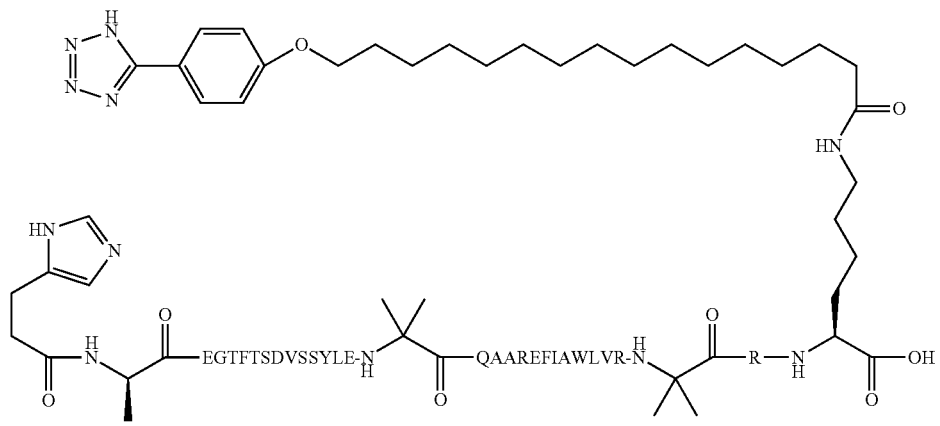

[3-(4-Imidazolyl)propionyl7,Aib22,35,Arg26,34,Lys37] GLP-1 (7-37) peptide was prepared as described in example 17.

The title compound was prepared by acylation of [3-(4-imidazolyl)propionyl7,Aib22,35,Arg26,34,Lys37]GLP-1 (7-37) peptide (18 mg) with 16-(4-(tetrazol-5-yl)phenoxy) hexadecanoic acid (8.0 mg) as described for Example 5. 2.59 mg of the title compound was obtained.

HPLC: (method B6): RT=35.9 min (100%)
LCMS: m/z=1309.2 ($MH_3^{3+}$). Calculated for ($MH_3^{3+}$): 1308.5

Example 20

0113-0000-0153, PrnC

N-epsilon37-(4-(4-(Tetrazol-5-yl)[1,1',4',1"]terphenyl-4"yloxy)butyroyl) [3-(4-imidazolyl)propionyl7, Aib22,35,Arg26,34,Lys37]GLP-1 (7-37) (Derivative of SEQ ID NO: 10)

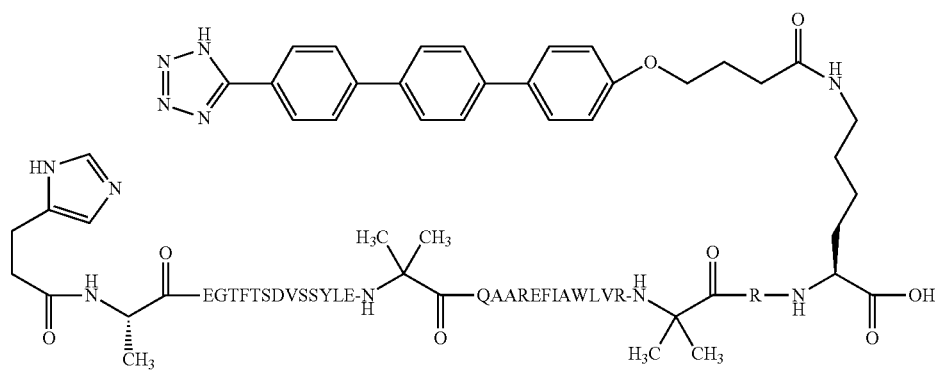

[3-(4-Imidazolyl)propionyl7,Aib22,35,Arg26,34,Lys37] GLP-1 (7-37) peptide was prepared as described in Example 17.

The title compound was prepared by acylation of [3-(4-imidazolyl)propionyl7,Aib22,35,Arg26,34,Lys37] GLP-1 (7-37) peptide (18 mg) with (4-(4-(tetrazol-5-yl)[1,1',4",1"] terphenyl-4"yloxy)butyric acid (8.0 mg) as described for Example 5.

0.83 mg of the title compound was obtained.
HPLC: (method B6): RT=31.9 min (100%)
LCMS: m/z=1303.3 ($MH_3^{3+}$). Calculated for ($MH_3^{3+}$): 1303.1

Example 21

0113-0000-0154, PrnC

N-epsilon37-(2-(2-(2-(16-(Tetrazol-5-yl)hexadecanoyl)amino)ethoxy)ethoxy)acetyl[Aib8,22,35, Arg26,34,Lys37] GLP-1 (7-37)

(Derivative of SEQ ID NO: 11)

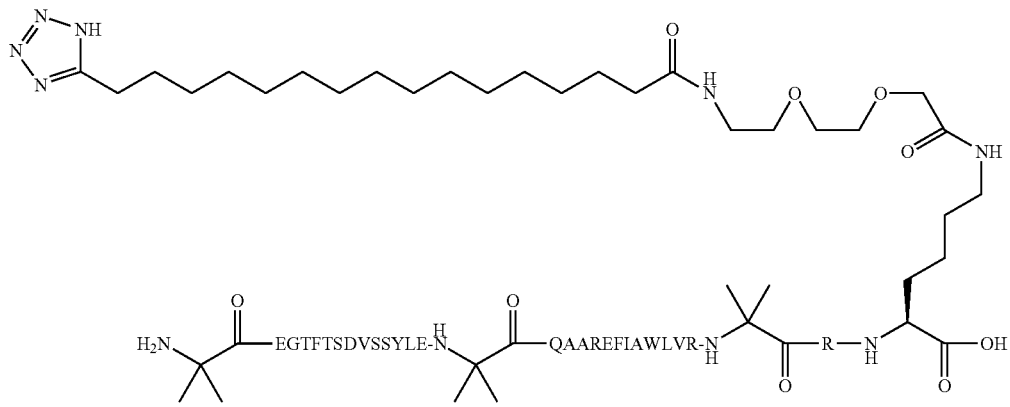

The attachment of the linker and sidechain to the specific lysine residue was done on a DDE-Lys(FMOC)-2-Cl-Trityl resin by Procedure for removal of the Fmoc-protection, followed by the Procedure for attachment of sidechains to Lysine residues and then the Procedure for removal of Dde-protection. This was followed by synthesis of the peptide to the N-terminus followed by cleavage of the peptide from the resin and purification.

HPLC: (method B6): RT=32.0 min (100%)
LCMS: m/z=1336.2 (MH$_3^{3+}$). Calculated for (MH$_3^{3+}$): 1335.9

Example 22

0113-0000-0155, PrnC

N-epsilon37-(2-(2-(2-(16-(Tetrazol-5-yl)(hexadecanoylamino)ethoxy)ethoxy)acetyl))

[3-(4-imidazolyl)propionyl7,Aib22,35,Arg26,34, Lys37] GLP-1 (7-37) peptide (Derivative of SEQ ID NO: 10)

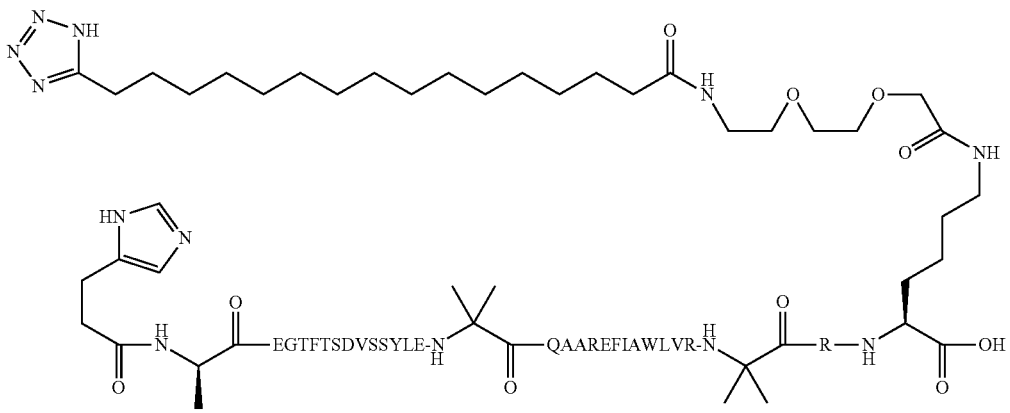

This compound was prepared as described in example 21.
HPLC: (method B6): RT=32.8 min (99%)
LCMS: m/z=1326.3 (MH$_3^{3+}$). Calculated for (MH$_3^{3+}$): 1326.2

Example 23

0113-0000-0156, PrnC

N-epsilon37-(2-(2-(2-(16-(Tetrazol-5yl)hexade-canoyl)amino)ethoxy)ethoxy)acetyl))[3-(4-imida-zolyl)propionyl7,Aib8,22,35,Arg26,34,Lys37] GLP-1 (7-37) peptide (Derivative of SEQ ID NO: 11)

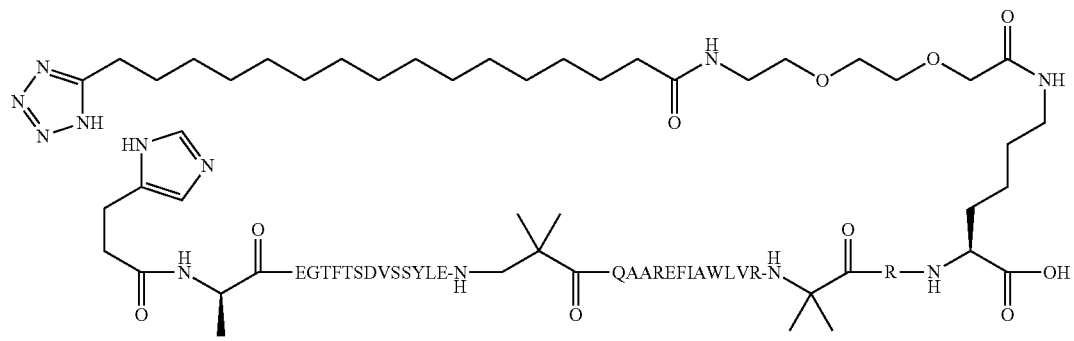

This compound was prepared as described in example 21.
HPLC: (method B6): RT=33.0 min (100%)
LCMS: m/z=1330.9 ($MH_3^{3+}$). Calculated for ($MH_3^{3+}$): 1330.9

Example 24

0113-0000-0202, PrnC

N-epsilon20-(2-(2-(2-(2-(2-(2-(2-(2-(2-(16-(Tetra-zol-5-yl)hexadecanoylamino)ethoxy)ethoxy)acety-lamino)ethoxy)ethoxy)acetylamino)ethoxy)ethoxy) acetyl[Lys20] Exendin-4 (1-39)amide (Derivative of SEQ ID NO: 15)

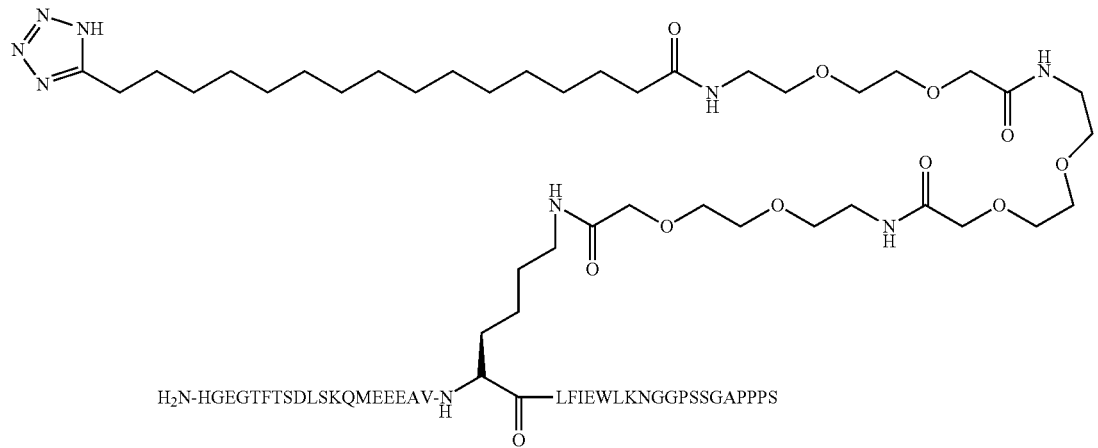

The attachment of sidechains and linkers to specific lysine residues on the crude resin bound protected peptide was carried out in a specific position by incorporation of Fmoc-Lys (Mtt)-OH during automated synthesis followed by selective deprotection with a batchwise treatment of the protected peptide resin with 1% TFA and 1% TIS in DCM until the yellow coloring had disappeared (after 1 h). This was followed by extensive wash with DMF, followed by attachment of the spacer and sidechain as described in example 21 and cleavage of the peptide from the resin and purification.

HPLC: (method B6): RT=31.1 min (100%)
LCMS: m/z=1634.3 ($MH_3^{3+}$). Calculated for ($MH_3^{3+}$): 1634.5

Example from JTK, TSHJ

NNC 0100-0000-0508 Example 25 (General procedure A, Acylation using human DesB30 insulin)

$N^{\epsilon B29}$-(16-2H-Tetrazol-5-yl-hexadecanoyl) gamma-Glu-des(B30) human insulin Step 1: Synthesis of 2-(16-2H-Tetrazol-5-yl-hexadecanoylamino)pentanedioic acid 1-tert-butyl ester

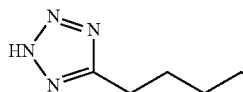 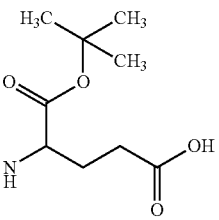

16-(2H-Tetrazol-5-yl)hexadecanoic acid (433 mg, 1.34 mmol) was heated in toluene (5 mL) and 2,2-dimethoxypropane (2 mL, 16 mmol) to reflux for to minutes. The solvent was removed in vacuo. Ethyl acetate (10 mL) was added, followed by N-(3-dimethylaminopropyl)-N'-ethylcarbodiimide hydrochloride (359 mg, 1.87 mmol) and 1 hydroxybenzotriazol (281 mg, 2 mmol). The reaction was stirred at room temperature for 30 min, and a mixture of L-glutamic acid alpha tert-butyl-gamma benzyl diester hydrochloride (661 mg, 2 mmol), diisopropylamin (0.34 mL, 2 mmol), and ethyl acetate (4 mL) was added. The mixture was stirred at room temperature overnight. The reaction was distributed between ethyl acetate (50 mL) and water (50 mL). The organic phase was dried ($Na_2SO_4$) and the solvent removed in vacuo. The crude 2-(16-2H-tetrazol-5-yl-hexadecanoylamino)pentanedioic acid 5-benzyl ester 1-tert-butyl ester was purified on C-18 RP-HPLC 5 cm×20 cm, flow 20 ml/min using a acetonitrile/water 60-90% gradient containing 0.1% TFA. Fractions containing 2-(16-2H-tetrazol-5-yl-hexadecanoylamino)pentanedioic acid 5-benzyl ester 1-tert-butyl ester were collected and the solvent removed in vacuo. The residue was redissolved in ethyl acetate (10 mL), palladium on activated charcoal (200 mg) was added, and the mixture was stirred under a hydrogen atmosphere (1 atm) for 3 hours. The mixture was filtered and the solvent removed in vacuo to yield 2-(16-2H-tetrazol-5-yl-hexadecanoylamino)pentanedioic acid 1-tert-butyl ester (100 mg).

HPLC-MS: m/z=511; $R_t$=4.17 min.

Step 2: Synthesis of 2-(16-2H-Tetrazol-5-yl-hexadecanoylamino)pentanedioic acid 1-tert-butyl ester 5-(2,5-dioxopyrrolidin-1-yl) ester

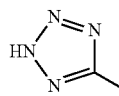 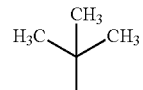 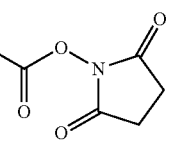

2-(16-2H-Tetrazol-5-yl-hexadecanoylamino)-pentanedioic acid 1-tert-butyl ester (100 mg, 0.19 mmol) was dissolved in THF (10 mL). The mixture was cooled with an ice bath. Diisopropylethylamine (0.041 mL, 0.24 mmol) and O—(N-succinimidyl)-N,N,N',N''-tetramethyluronium tetrafluoroborate (71 mg, 0.24 mmol) was added. The mixture was stirred under nitrogen at 0° C. After 30 minutes the ice cooling was removed and the mixture was stirred for an additional 3 hours. The solvent was removed in vacuo followed by coevaporation of the residue with toluene. The crude product was dissolved in ethyl acetate (30 mL), washed with water (2×20 mL), and the combined aqueous phases extracted once with ethyl acetate (30 mL). The combined organic phases were dried ($Na_2SO_4$), the solvent removed in vacuo to yield the title compound (83 mg), which was used in subsequent step without further purification.

HPLC-MS: m/z=607; $R_t$=4.73 min.

Step 3: Synthesis of $N^{\epsilon B29}$-(16-2H-Tetrazol-5-yl-hexadecanoyl) gamma-Glu-des(B30) human insulin

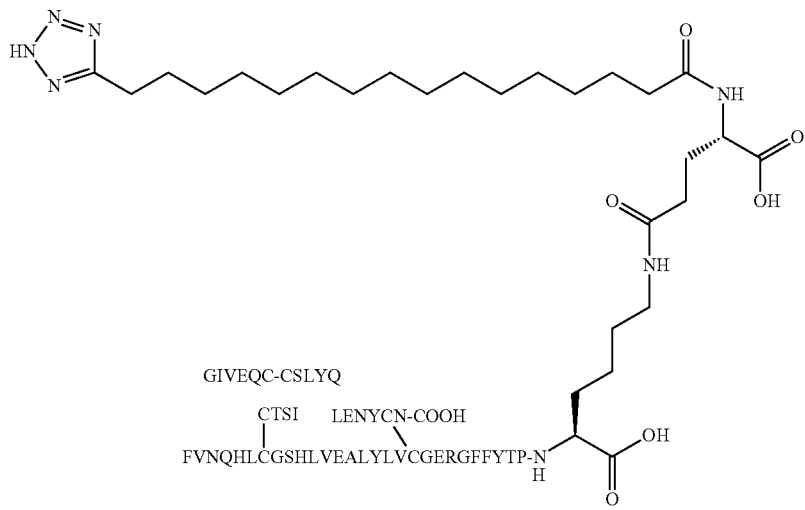

A1B1BocBoc des(B30) insulin (Kurtzhals P; Havelund S; Jonassen I; Kiehr B; Larsen U D; Ribel U; Markussen J Biochemical Journal, 1995, 312, 725-731) (0.2 g, 0.034 mmol) was dissolved in DMSO (3 mL). Triethylamine (0.047 mL, 0.34 mmol) and a solution of 2-(16-2H-tetrazol-5-yl-hexadecanoylamino)pentanedioic acid 1-tert-butyl ester 5-(2,5-dioxo-pyrrolidin-1-yl) ester (58 mg, 0.096 mmol) in DMSO (1 mL) were added, and the mixture was shaken at room temperature for 1 hour. The mixture was cooled with an icebath (the DMSO froze), water (10 mL) was added and the frozen mixture was allowed to melt. The pH was adjusted to 5.2 with 1N HCl. The product was allowed to precipitate for 1 hour at 5° C. The precipitate was isolated by centrifugation and treated with TFA (10 mL) for 30 min. This solution was poured into ice-cooled diethylether (40 mL), and the crude product was isolated by centrifugation and purified on C-18 RP-HPLC 5 cm×20 cm, flow 20 ml/min using an acetonitrile/water 25-45% gradient containing 0.1% TFA. Fractions containing the product were combined and lyophilized. To the lyophilized material was added water (7.2 mL) and the pH adjusted to 8.98 with 1 N and 0.1 N NaOH. The pH was adjusted back to 5.2-5.5 with 0.1 N HCl. The precipitate was isolated by centrifugation and lyophilized to give the title compound.

HPLC-MS: m/z=1536 (m/4), 1229 (m/5), 1024 (m/6); $R_t$=3.47 min.

Example 26

$N^{B29\epsilon}$-4-[4"-(1H-Tetrazol-5-yl)-[1,1';4',1"]terphenyl-4-yloxy]-butyroyl des(B30) insulin

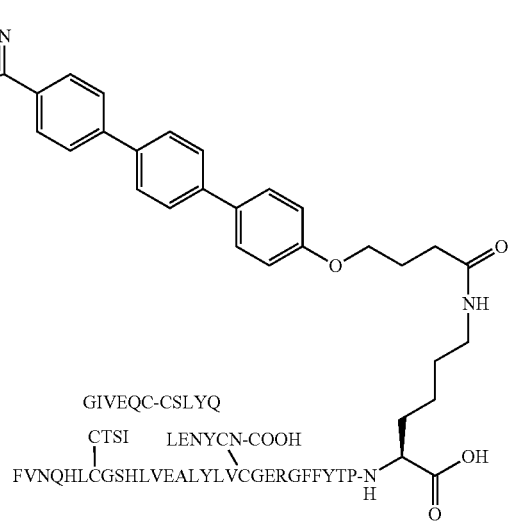

4-(4-(5-Tetrazolyl)-[1,1',4',1"]-terphenyl-4"-yloxy)butyric acid (166 mg, 0.42 mmol) was suspended in DMF (2 ml) and treated with TSTU (150 mg, 0.50 mmol) and DIEA (85 µL, 0.50 mmol). The mixture was stirred overnight. The solvent was removed in vacuo and the residue was partitioned between ethyl acetate and 0.1 M HCl. The organic phase/suspension was filtered and the solid was washed with ether and dried in vacuo to provide activated 4-(4-(5-tetrazolyl)[1,1',4',1"1]-terphenyl-4"-yloxy)butyric acid, 164 mg. Des(B30) human insulin (100 mg, 0.018 mmol) was dissolved in 100 mM $Na_2CO_3$ (1.3 ml, pH 10.2) at room temperature. Activated 4-(4-(5-tetrazolyl)-[1,1',4',1"]-terphenyl-4"-yloxy)butyric acid (10 mg, 0.022 mmol) was dissolved in DMSO (1.3 ml) and added to the insulin solution. After 30 min, 0.2 M methylamine (0.1 ml) was added. pH was adjusted to 5.5 with 1 M HCl, and the isoelectric precipitate was collected by centrifugation and dried in vacuo. The coupling yield was 75% (RP-HPLC, C4 column; buffer A: 10% MeCN in 0.1% TFA-water, buffer B: 80% MeCN in 0.1% TFA-water; gradient 20% to 90% B in 16 minutes). $N^{B29\epsilon}$-4-[4"-(1H-Tetrazol-5-yl)[1,1';4',1"]terphenyl-4-yloxy]butyroyl des(B30) insulin was purified by RP-HPLC on C4-column, buffer A: 20% EtOH+0.1% TFA, buffer B: 80% EtOH+0.1% TFA; gradient 15-60% B, followed by HPLC on C4-column, buffer A: 10 mM Tris+15 mM ammonium sulphate in 20% EtOH, pH 7.3, buffer B: 80% EtOH, gradient 15-60% B. The collected fractions were desalted on Sep-Pak with 70% acetonitrile+0.1% TFA, neutralized by addition of ammonia and freeze-dried. The unoptimized yield was 8 mg (7%). The purity as evaluated by HPLC was >98%. LCMS 6088, $C_{276}H_{394}N_{68}O_{77}S_6$ requires 6089.

Example 27

$N^{B29\epsilon}$-16-[4'-(1H-tetrazol-5-yl)-biphenyl-4-yloxy]-hexadecanoyl des(B30) insulin 0100-0000-0536

16-(4'-(5-Tetrazolyl)biphenyl-4-yloxy)hexadecanoic acid (309 mg, 0.63 mmol) was suspended in DMF (4 ml) and treated with TSTU (227 mg, 0.75 mmol) and DIEA (127 µL, 0.75 mmol). The mixture was stirred overnight. The solvent was removed in vacuo and the residue was partitioned between ethyl acetate and 0.1 M HCl. The organic phase/suspension was filtered and the solid was washed with ether and dried in vacuo to provide activated 16-(4'-(5-tetrazolyl)biphenyl-4-yloxy)hexadecanoic acid, 290 mg. Des(B30) human insulin (100 mg, 0.018 mmol) was dissolved in 100 mM $Na_2CO_3$ (1.3 ml, pH 10.2) at room temperature. Activated 16-(4'-(5-tetrazolyl)biphenyl-4-yloxy)hexadecanoic acid (12 mg, 0.022 mmol) was dissolved in DMSO (1.3 ml) and added to the insulin solution. After 30 min, 0.2 M methylamine (0.1 ml) was added. pH was adjusted to 5.5 with 1 M HCl, and the isoelectric precipitate was collected by centrifugation and dried in vacuo. The coupling yield was 37% (RP-HPLC, C4 column; buffer A: 10% MeCN in 0.1% TFA-water, buffer B: 80% MeCN in 0.1% TFA-water; gradient 20% to 90% B in 16 minutes). $N^{B29\epsilon}$-16-[4'-(1H-Tetrazol-5-yl)biphenyl-4-yloxy]hexadecanoyl des(B30) insulin was purified by RP-HPLC on C4-column, buffer A: 20% EtOH+0.1% TFA, buffer B: 80% EtOH+0.1% TFA; gradient 15-60% B, followed by HPLC on C4-column, buffer A: 10 mM Tris+15 mM ammonium sulphate in 20% EtOH, pH 7.3, buffer B: 80% EtOH, gradient 15-60% B. The collected fractions were desalted on Sep-Pak with 70% acetonitrile+0.1% TFA, neutralized by addition of ammonia and freeze-dried. The unoptimized yield was 5 mg (7%). The purity as evaluated by HPLC was >98%. LCMS 6180, $C_{282}H_{414}N_{68}O_{77}S_6$ requires 6181.

HPLC-method 84:
A: acetonitril
B: water
D: 1.0% TFA in water
Gradient: 5-->95% A, 15 min, 1.0 ml/min
Symmetry 300, C18, 5 µm, 3.9×150 mm column
Column oven temperature=42° C.; detection at 214 nm.

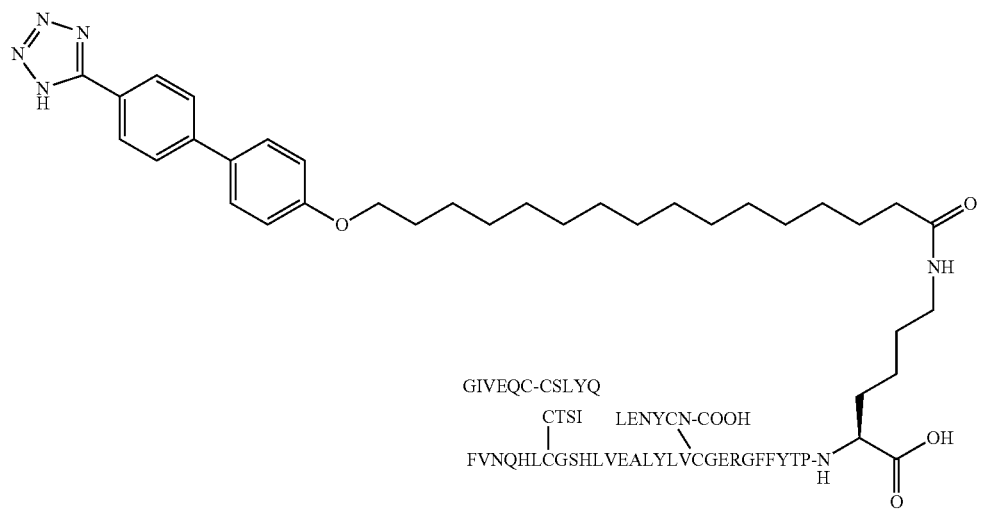

Example 28

0113-0000-0139; HSt $N^{\epsilon37}$-16-(4-(4-(5-Tetrazolyl)phenyl)phenyloxy)hexadecanoyl)-[Gly8,Arg26,34]GLP-1(7-37) peptide
(Derivative of SEQ ID NO: 8)

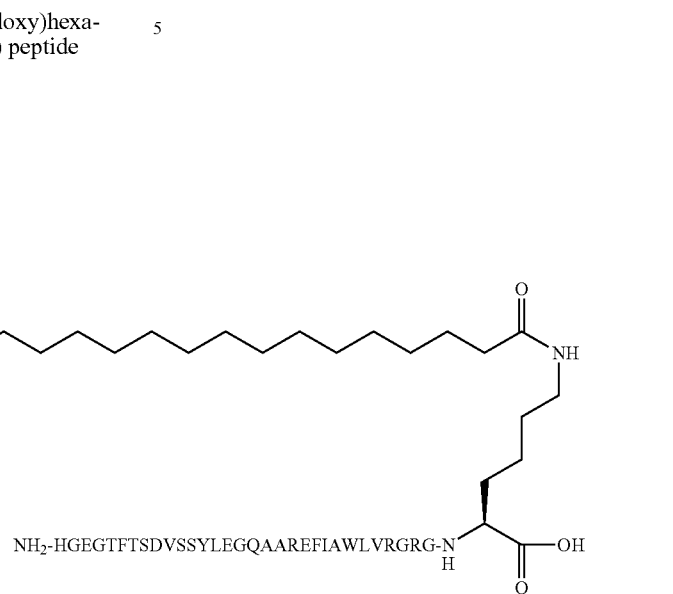

The title compound was prepared as example 6 from 16-(4-(4-(5-tetrazolyl)phenyl)phenyloxy)hexadecanoic acid and [Gly8,Arg26,34]GLP-1-(7-37) peptide (25 mg). 6.1 mg of the title product was obtained.

HPLC (method B4): RT=13.07 min (94%)
LCMS: m/z=1335 ($MH_3^{3+}$). Calculated for ($MH_3^{3+}$): 1334

Example 29

0113-0000-0140; HSt $N^{\epsilon37}$-(4-(4-(4-(4-(5-Tetrazolyl)phenyl)phenyl)phenoxy)butyryl)[Gly8,Arg26,34]GLP-1-(7-37) peptide
(Derivative of SEQ ID NO: 8)

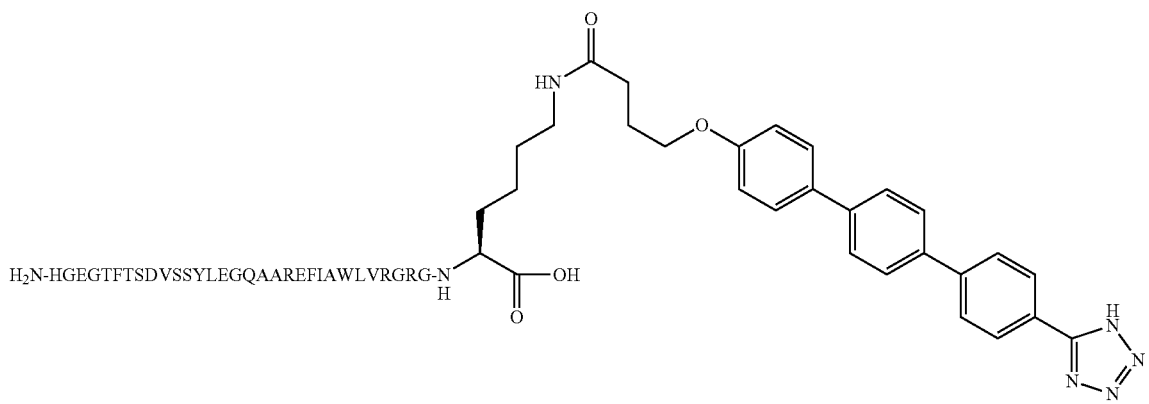

The title compound was prepared as example 6 from 4-(4-(4-(4-(5-tetrazolyl)phenyl)phenyl)phenoxy)butyric acid and [Gly8,Arg26,34]GLP-1-(7-37) peptide (30 mg). 3.8 mg of the title product was obtained.

HPLC (method B4): RT=10.84 min (86%)
LCMS: m/z=1303 ($MH_3^{3+}$). Calculated for ($MH_3^{3+}$): 1303

Example 30

17,17-Bis(5-tetrazolyl)heptadecanoic acid

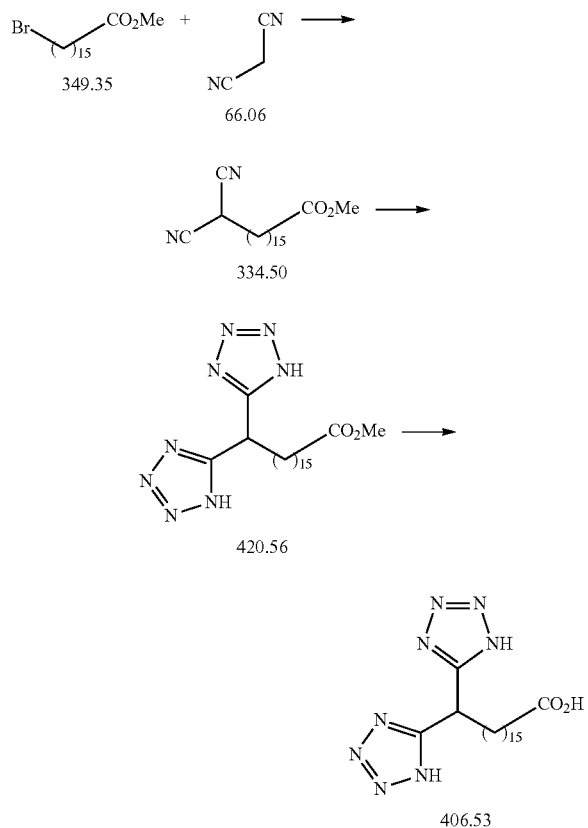

17,17-Dicyanoheptadecanoic acid methyl ester

To 16-bromohexadecanoic acid methyl ester (1.40 g, 4.0 mmol) in MeCN (20 ml) were added malonodinitrile (1.01 g, 15.3 mmol) and K$_2$CO$_3$ (0.92 g, 6.64 mmol). The mixture was stirred at 80° C. for 18.5 h. Water (50 ml) and 1N HCl (50 ml) were added, and the product was extracted with AcOEt. The combined extracts were washed with brine, dried over MgSO$_4$, and concentrated under reduced pressure. 1.87 g (100%) of an oil was obtained which crystallized completely after some hours.

$^1$H NMR (DMSO-d$_6$): δ 1.24 (m, 22H), 1.36-1.55 (m, 4H), 1.96 (m, 2H), 2.28 (t, J=7 Hz, 2H), 3.57 (s, 3H), 4.80 (t, J=7 Hz, 1H).

17,17-Bis(5-tetrazolyl)heptadecanoic acid methyl ester

To 17,17-dicyanoheptadecanoic acid methyl ester (2.25 g, 6.73 mmol) were added DMF (12 ml), AcOH (4.1 ml, 68.3 mmol), NEt$_3$ (9.0 ml, 64.9 mmol), and NaN$_3$ (5.25 g, 80.8 mmol). The resulting mixture was stirred at 140° C. for 19 h. Water (90 ml) and 1N HCl (60 ml) were added, and the mixture was acidified by addition of concentrated hydrochloric acid. The solid was filtered off, washed with water, and recrystallized from hot methanol, to yield 1.70 g (60%) of the title compound as a solid.

$^1$H NMR (DMSO-d$_6$): δ 1.21 (br s, 24H), 1.51 (m, 2H), 2.19 (m, 2H), 2.28 (t, J=7 Hz, 2H), 3.57 (s, 3H), 4.94 (t, J=7 Hz, 1H).

17,17-Bis(5-tetrazolyl)heptadecanoic acid 17,17-Bis(5-tetrazolyl)heptadecanoic acid methyl ester (1.70 g, 4.04 mmol) was dissolved in MeOH (40 ml), and a solution of NaOH (1.17 g, 29 mmol) in water (3 ml) was added. After stirring at room temperature for 19 h no more starting ester could be detected by $^1$H NMR, and the mixture was diluted with a mixture of water (130 ml) and 1N HCl (50 ml). The product was isolated by filtration, washed with water, and recrystallized from boiling MeCN (40 ml), to yield 0.53 g (32%) of the title compound as a solid. From the mother liquor more product (0.39 g) could be obtained. Total yield: 0.92 g, 56%.

$^1$H NMR (DMSO-d$_6$): δ 1.21 (m, 24H), 1.48 (m, 2H), 2.18 (m, 4H), 4.94 (t, J=7 Hz, 1H).

Example 31

0113-0000-0166; HSt

N$^{ε37}$-(17,17-Bis(5-tetrazolyl)heptadecanoyl)[Gly8, Arg26,34]GLP-1-(7-37) peptide (Derivative of SEQ ID NO: 8)

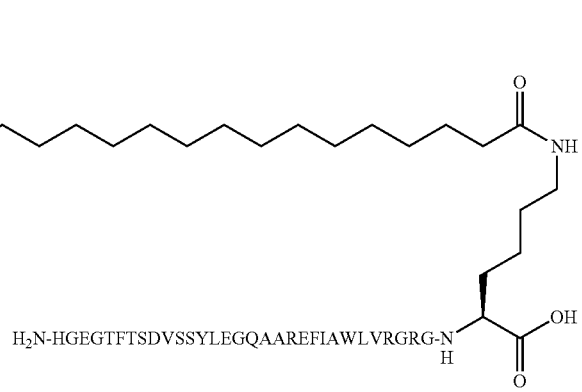

The title compound was prepared as example 6 from 17,17-bis(5-tetrazolyl)heptadecanoic acid and [Gly8,Arg26,34] GLP-1-(7-37) peptide (45 mg). 12.5 mg of the title product was obtained.

HPLC (method B4): RT=11.37 min (91%)

LCMS: m/z=1306 ($MH_3^{3+}$), 1959 ($MH_2^{2+}$). Calculated for ($MH_3^{3+}$): 1306

Example 32

4-(4'-{5-[4-(5-Tetrazolyl)phenyl]-[1,2,4]oxadiazol-3-yl}biphenyl-4-yloxy)butyric acid

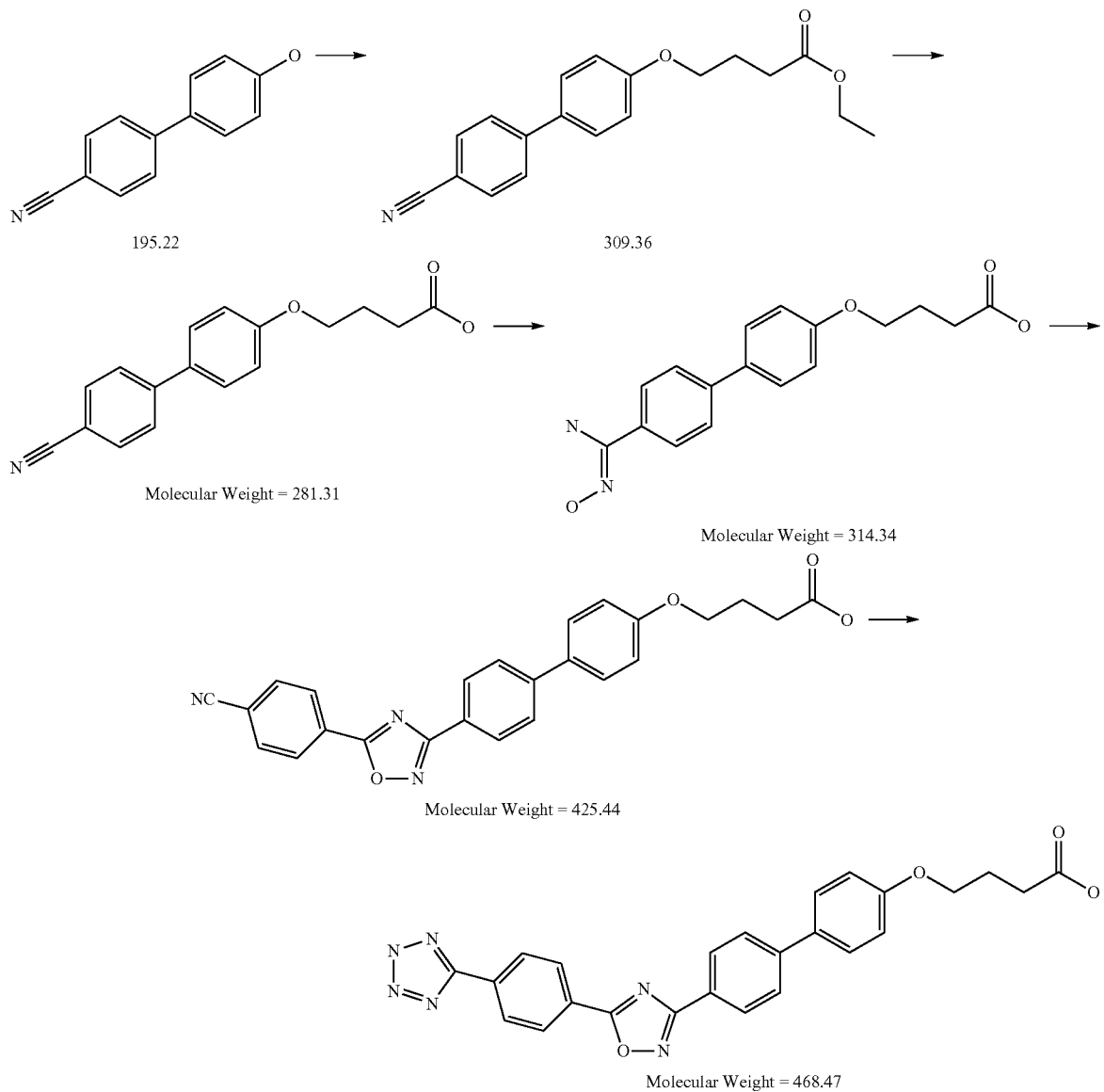

A mixture of 4'-cyano-4-hydroxybiphenyl (4.0 g, 20.5 mmol), MeCN (30 ml), ethyl 4-bromobutyrate (3.75 ml, 5.11 g, 26.2 mmol), and $K_2CO_3$ (3.86 g, 27.9 mmol) was stirred at 85° C. After 20 h water (150 ml) was added, and the product was extracted with AcOEt. The combined extracts were washed with brine, dried over $MgSO_4$, and concentrated, to yield 6.91 g (100%) of 4-(4'-cyanobiphenyl-4-yloxy)butyric acid ethyl ester as an oil.

To a solution of 4-(4'-cyanobiphenyl-4-yloxy)butyric acid ethyl ester (3.78 g, 12.7 mmol) in THF (50 ml) was added a solution of NaOH (1.0 g, 25 mmol) in water (1.5 ml). The mixture was stirred at room temperature for 1.5 h and then at 67° C. for 3 h. More NaOH (1 g) in water (1 ml) was added, and stirring at room temperature was continued for 15 h. MeOH (10 ml) was added, and after stirring at room temperature for 1.5 h the mixture was diluted with water (150 ml) and acidified with concentrated, aqueous HCl (6.6 ml). The product was isolated by filtration and washed with water (approx 20 ml). The solid was suspended in MeCN (50 ml), heated to reflux (no dissolution) and allowed to cool to room temperature. Filtration and drying under reduced pressure yielded 2.70 g (76%) of 4-(4'-cyanobiphenyl-4-yloxy)butyric acid as a colorless solid.

A mixture of 4-(4'-cyanobiphenyl-4-yloxy)butyric acid (2.70 g, 9.60 mmol), EtOH (10 ml), THF (15 ml), K$_2$CO$_3$ (3.35 g, 24.2 mmol), and hydroxylamine hydrochloride (1.50 g, 21.6 mmol) was stirred at room temperature for 3.5 d, and then at 80° C. for 24 h. Water (100 ml) and 1N HCl (50 ml) were added, and the product was isolated by filtration and washed with water. The solid was suspended in MeCN (70 ml), heated to reflux, kept at room temp overnight, filtrated off, and dried under reduced pressure to yield 3.23 g (100%) of 4-(4'-(N-hydroxycarbamimidoyl)biphenyl-4-yloxy)butyric acid.

A solution of 4-cyanobenzoyl chloride (2.29 g, 13.8 mmol) in dioxane (10 ml) was added to a suspension of 4-(4'-(N-hydroxycarbamimidoyl)biphenyl-4-yloxy)butyric acid (3.23 g, 9.6 mmol) in dioxane (50 ml) and pyridine (2.5 ml, 31.6 mmol). The mixture was stirred at room temperature for 4 h, and then heated to 100° C. for 22 h. The mixture was concentrated to ½ of its original volume, diluted with water (100 ml), and acidified by addition of concentrated hydrochloric acid (3 ml). The product was isolated by filtration and washed with water (50 ml). The solid was suspended in MeCN (70 ml), heated to reflux, allowed to cool, filtered off, and dried under reduced pressure to yield 3.17 g (54%) of 4-(4'-{5-[4-cyanophenyl]-[1,2,4]oxadiazol-3-yl}biphenyl-4-yloxy)butyric acid as a solid.

A mixture of 4-(4'-{5-[4-cyanophenyl]-[1,2,4]oxadiazol-3-yl}biphenyl-4-yloxy)butyric acid (3.17 g, 7.45 mmol), DMF (15 ml), AcOH (2.25 ml, 37.5 mmol), NEt$_3$ (5.0 ml, 36 mmol), and NaN$_3$ (2.89 g, 44.5 mmol) was stirred at 140° C. After 24 h water (150 ml) and concentrated hydrochloric acid (6 ml) were added. The product was isolated by filtration, washed with water, resuspended in MeCN (100 ml), heated to reflux (it did not dissolve completely), homogenized, and allowed to cool to room temperature. Filtration yielded 2.50 g (72%) of 4-(4'-{5-[4-(5-tetrazolyl)phenyl]-[1,2,4]oxadiazol-3-yl}biphenyl-4-yloxy)butyric acid as a solid.

$^1$H NMR (DMSO-d$_6$): δ 1.98 (m, 2H), 2.41 (t, J=7 Hz, 2H), 4.06 (t, J=7 Hz, 2H), 7.07 (d, J=8 Hz, 2H), 7.72 (d, J=8 Hz, 2H), 7.88 (d, J=8 Hz, 2H), 8.16 (d, J=8 Hz, 2H), 8.32 (d, J=8 Hz, 2H), 8.41 (d, J=8 Hz, 2H).

Example 33

0113-0000-0169; HSt

N$^{ε37}$-(4-(4'-{5-[4-(5-Tetrazolyl)phenyl]-[1,2,4]oxadiazol-3-yl}biphenyl-4-yloxy)butyryl)[Gly8,Arg26,34]GLP-1-(7-37) peptide (Derivative of SEQ ID NO: 8)

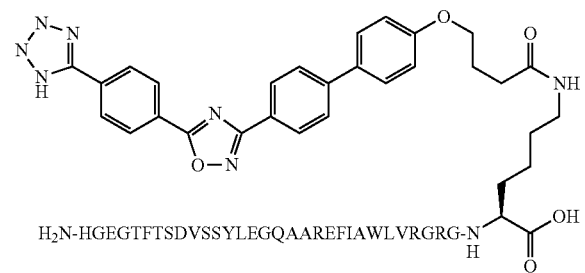

The title compound was prepared as example 6 from 4-(4'-{5-[4-(5-tetrazolyl)phenyl]-[1,2,4]oxadiazol-3-yl}biphenyl-4-yloxy)butyric acid and [Gly8,Arg26,34]GLP-1-(7-37) peptide (60 mg). 1.8 mg of the title product was obtained.

HPLC (method B4): RT=11.26 min (99%)
LCMS: m/z=1326 (MH$_3^{3+}$). Calculated for (MH$_3^{3+}$): 1326

Example 34

16-(4,5-Bis(5-tetrazolyl)imidazol-1-yl)hexadecanoic acid

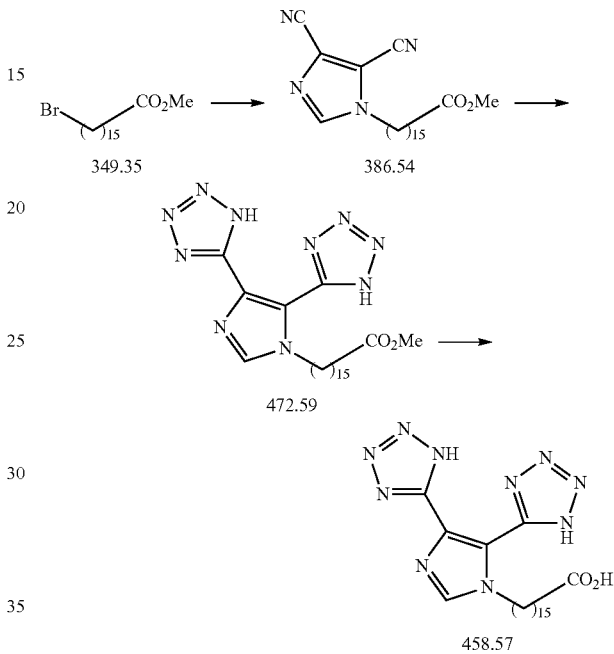

A mixture of 16-bromohexadecanoic acid methyl ester (3.50 g, 10.02 mmol), 4,5-dicyanoimidazole (1.52 g, 12.87 mmol), MeCN (30 ml), and K$_2$CO$_3$ (1.95 g, 14.1 mmol) was stirred at 80° C. for 66 h.

Water (100 ml) and 1N HCl (40 ml) were added, and the product was extracted twice with AcOEt. The combined extracts were washed with brine, dried over MgSO$_4$, and concentrated under reduced pressure. Recrystallization from MeOH (10 ml) yielded 3.41 g (88%) of 16-(4,5-dicyanoimidazol-1-yl)hexadecanoic acid methyl ester as a colorless solid.

A mixture of 16-(4,5-dicyanoimidazol-1-yl)hexadecanoic acid methyl ester (3.86 g, 10 mmol), DMF (8 ml), AcOH (6.2 ml, 103 mmol), NEt$_3$ (13.8 ml, 100 mmol), and NaN$_3$ (7.98 g, 123 mmol) was stirred at 140° C. More DMF (9 ml) was added after 20 h. After 44 h water (100 ml) was added, followed by acidification with concentrated hydrochloric acid (approx 12 ml). The product was filtered off, washed with water, resuspended in MeCN (100 ml), heated to reflux (no complete dissolution), and allowed to cool. Filtration and drying under reduced pressure yielded 4.57 g (97%) of 16-(4,5-bis(5-tetrazolyl)imidazol-1-yl)hexadecanoic acid as a brown solid. This solid (4.57 g, 9.67 mmol) was mixed with MeOH (50 ml) and a solution of NaOH (4.01 g, 100 mmol) in water (10 ml). The resulting clear solution was stirred at 60° C. for 22 h, and poured into a stirred mixture of water (400 ml) and concentrated hydrochloric acid (12M, 20 ml). The solid was filtered off, washed with water, resuspended in MeCN (150 ml), heated to reflux, and allowed to stand at room temperature overnight. Filtration and drying under reduced pressure yielded 3.71 g (84%) of the title acid as a brown solid.

$^1$H NMR (DMSO-d$_6$): δ 1.20 (m, 22H), 1.48 (m, 2H), 1.65 (m, 2H), 2.19 (t, J=7 Hz, 2H), 4.24 (t, J=7 Hz, 2H), 8.38 (s, 1H).

Example 35

0113-0000-0174; HSt

N$^{ε37}$-(16-(4,5-Bis(5-Tetrazolyl)imidazol-1-yl)hexadecanoyl)Gly8,Arg26,34GLP-1-(7-37) peptide (Derivative of SEQ ID NO: 8)

To a suspension of 2-chlorotrityl chloride resin (2 g; crosslinked polystyrene) in dichloromethane were added a solution of (2-(2-(9H-fluoren-9-ylmethoxycarbonylamino) ethoxy)ethoxy)acetic acid (0.55 g, 1.43 mmol) in dichloromethane (15 ml) and then a solution of DIPEA (0.65 ml) in dichloromethane (7 ml). After stirring at room temperature for 20 min methanol (2 ml) was added, and stirring was continued for 10 min. The resin was filtered, washed twice with dichloromethane and once with DMF. The resin was treated with a 20%-solution of piperidine in DMF (2×10 min), and washed extensively with DMF and dichloromethane. A solution of 16-(5-tetrazolyl)hexadecanoic acid (1.0 g, 3.08 mmol), 3-hydroxy-3,4-dihydro-1,2,3-benzotriazin-4-one (0.49 g, 3.0 mmol), and EDC (0.58 g, 3.03 mmol) in dichloromethane (25 ml) was added to the resin, and the

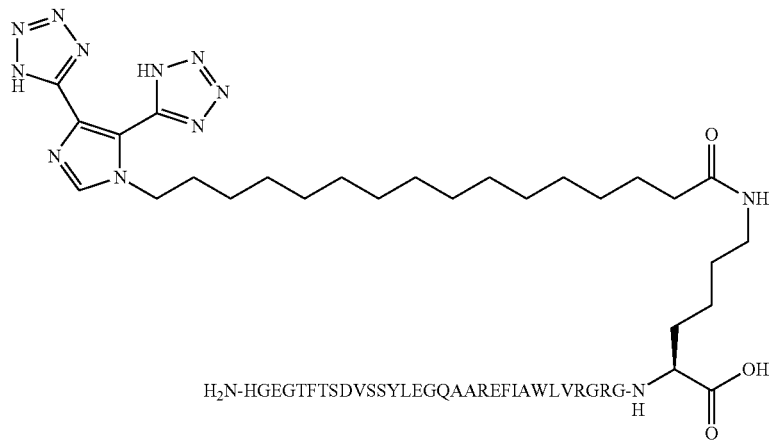

The title compound was prepared as example 6 from 16-(4,5-bis(5-tetrazolyl)imidazol-1-yl)hexadecanoic acid and [Gly8,Arg26,34]GLP-1-(7-37) peptide (60 mg). 8 mg of the title product was obtained.

HPLC (method B4): RT=11.61 min (98%)
LCMS: m/z=1323 (MH$_3^{3+}$). Calculated for (MH$_3^{3+}$): 1323

Example xxx (2-(2-(16-(5-Tetrazolyl)hexadecanoylamino)ethoxy) ethoxy)acetic acid mixture was shaken for 60 h. The resin was then extensively washed with DMF, dichloromethane and methanol, and suspended in a mixture of trifluoroacetic acid and dichloromethane (25:75; vol). After 0.5 h the resin was filtered, rinsed with dichloromethane, the combined filtrates were concentrated and the residue recrystallized from MeCN to yield 0.26 g of the title compound.

$^1$H NMR (DMSO-d$_6$): δ 1.23 (m, 22H), 1.46 (m, 2H), 1.67 (m, 2H), 2.04 (t, J=7 Hz, 2H), 2.85 (t, J=7 Hz, 2H), 3.18 (m, 2H), 3.38 (m, 2H), 3.51 (m, 2H), 3.58 (m, 2H), 4.01 (s, 2H).

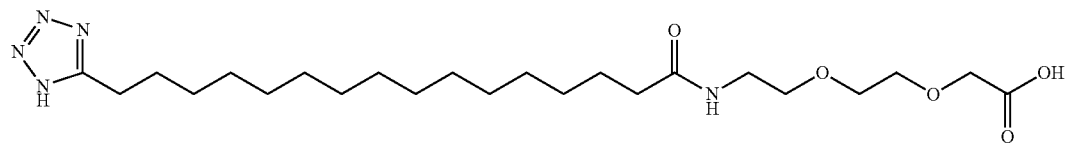 [SMILES: O=C(O)COCCOCCNC(=O)CCCCCCCCCCCCCCCc1nnn[nH]1]

Example 36

0113-0000-0197; HSt

N^ε37-((2-(2-(16-(5-Tetrazolyl)hexadecanoylamino)ethoxy)ethoxy)acetyl)

[Gly8,Arg26,34]GLP-1-(7-37) peptide (Derivative of SEQ ID NO: 8)

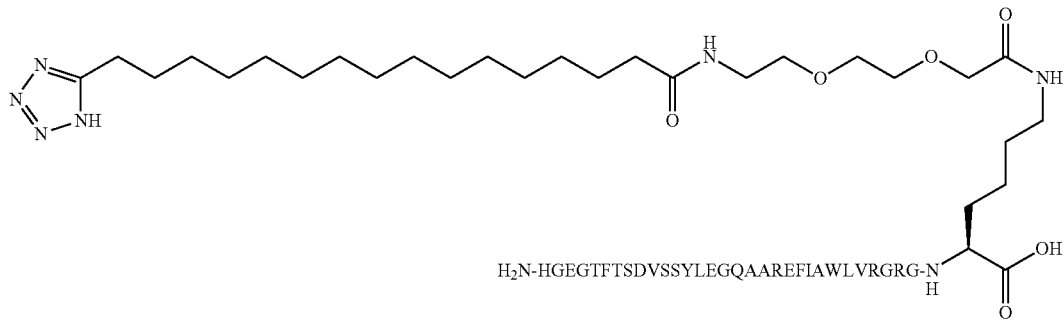

The title compound was prepared as example 6 from (2-(2-16-(5-tetrazolyl)hexadecanoylamino)ethoxy)ethoxy)acetic acid and [Gly8,Arg26,34]GLP-1-(7-37) peptide (85 mg). 28 mg of the title product was obtained.

HPLC (method B4): RT=11.35 min (95%)
LCMS: m/z=1327 $(MH_3^{3+})$. Calculated for $(MH_3^{3+})$: 1327

Example 37

0113-0000-0184; HSt

N^ε26-(4-{16-(Tetrazol-5-yl)hexadecanoylsulfamoyl}butyryl)[(3-(4-imidazolyl)propionyl7,Arg34]GLP-1-(7-37) peptide (Derivative of SEQ ID NO: 13)

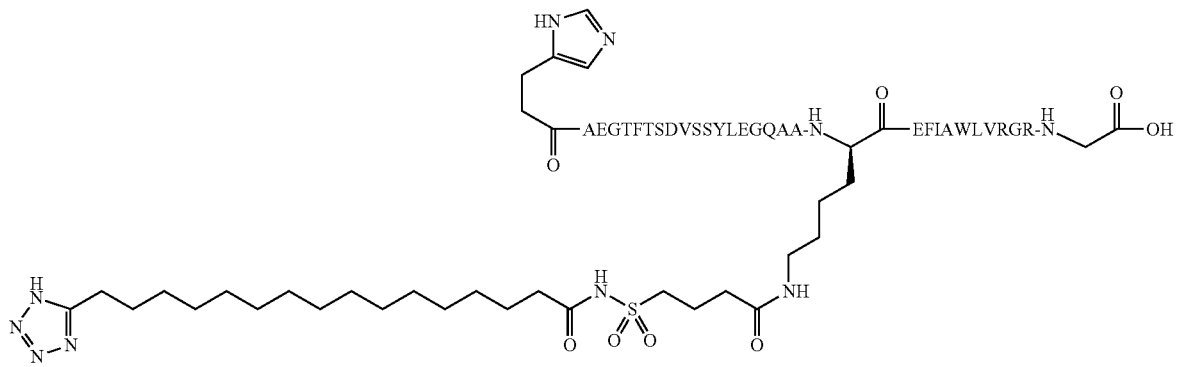

This compound was prepared as example 5 from 4-(16-(5-tetrazolyl)hexadecanoylaminosulfonyl)butyric acid and [(3-(4-imidazolyl)propionyl7,Arg34]GLP-1-(7-37) peptide (50 mg). 13.3 mg of the title compound was obtained.

HPLC (method B4): RT=11.61 min (98%)
LCMS: m/z=1276 $(MH_3^{3+})$. Calculated for $(MH_3^{3+})$: 1276

Example 38

0113-0000-0196; HSt

N$^{\epsilon 34}$-(16-{Tetrazol-5-yl}hexadecanoyl)-[Gly8, Arg26] GLP-1 (7-34) peptideamide (Derivative of SEQ ID NO: 14)

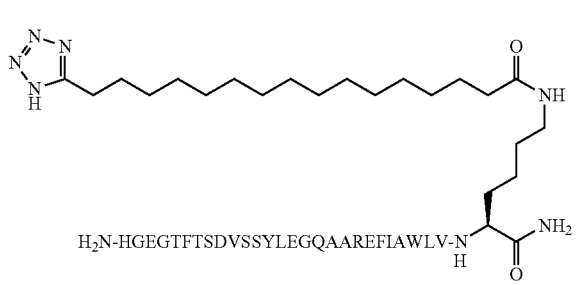

The title compound was prepared as example 6 from 16-(5-tetrazolyl)hexadecanoic acid and [Gly8, Arg26] GLP-1 (7-34) peptideamide (50 mg). 17 mg of the title product was obtained.

HPLC (method B4): RT=12.53 min (100%)

LCMS: m/z=1136 (MH$_3^{3+}$). Calculated for (MH$_3^{3+}$): 1136

Example 39

(2-(2-(4-(16-(5-Tetrazolyl)hexadecanoylaminosulfonyl)butyrylamino)ethoxy)ethoxy)acetic acid

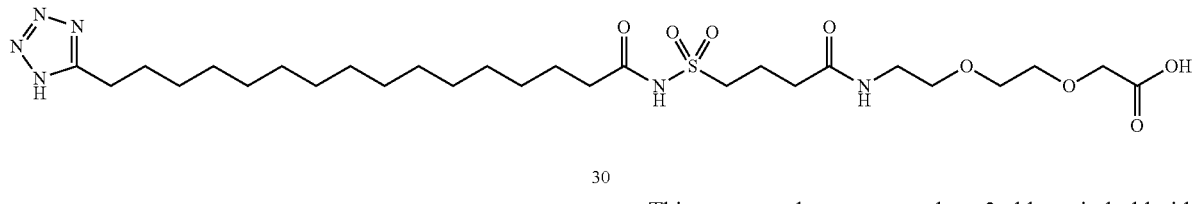

This compound was prepared on 2-chlorotrityl chloride resin as described for the synthesis of (2-(2-(16-(5-tetrazolyl)hexadecanoylamino)ethoxy)ethoxy)acetic acid.

$^1$H NMR (DMSO-d$_6$): δ 1.23 (m, 22H), 1.49 (m, 2H), 1.68 (m, 2H), 1.85 (m, 2H), 2.23 (m, 4H), 2.85 (t, J=7 Hz, 2H), 3.19 (m, 2H), 3.35 (m, 4H), 3.52 (m, 2H), 3.59 (m, 2H), 4.01 (s, 2H), 7.91 (br t, J=6 Hz, 1H), 11.55 (br s, 1H).

Example 40

0113-0000-0205; HSt

N$^{\epsilon 26}$-({2-[2-(4-(16-(Tetrazol-5-yl)hexadecanoylsulfamoyl)butyrylamino)ethoxy]ethoxy}acetyl)-[Arg34] GLP-1 (7-37) peptide (Derivative of SEQ ID NO: 7)

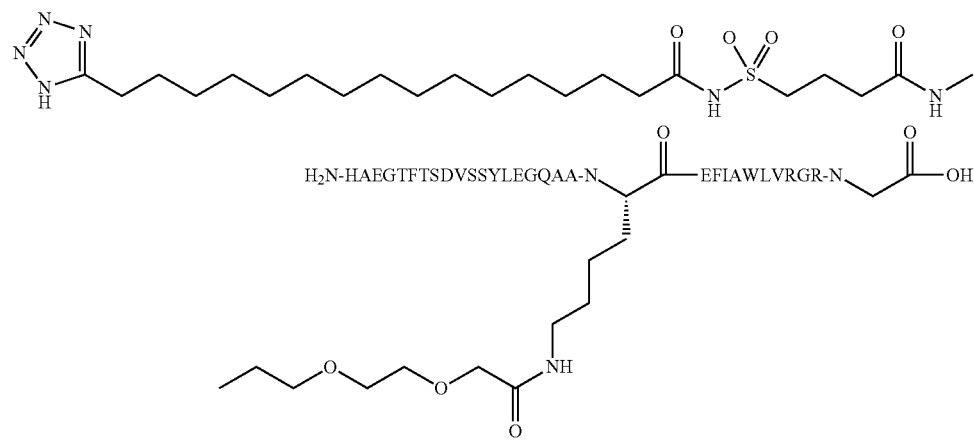

The title compound was prepared as example 6 from (2-(2-(4-(16-(5-tetrazolyl)hexadecanoylaminosulfonyl)butyrylannino)ethoxy)ethoxy)acetic acid and [Arg34]GLP-1-(7-37) peptide (350 mg). 35 mg of the title product was obtained.
HPLC (method B4): RT=11.63 min (99%)
LCMS: m/z=1329 ($MH_3^{3+}$). Calculated for ($MH_3^{3+}$): 1329

Example 41

0113-0000-0206; HSt $N^{\epsilon 34}$-({2-[2-(4-(16-(Tetrazol-5-yl)hexadecanoylsulfamoyl)butyrylamino)ethoxy]ethoxy}acetyl)-[Arg26] GLP-1 (7-34) peptideamide (Derivative of SEQ ID NO: 14)

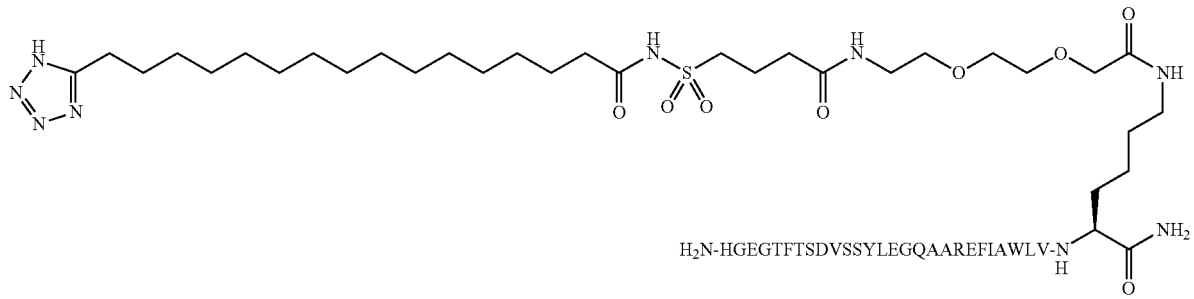

The title compound was prepared as example 6 from (2-(2-(4-(16-(5-tetrazolyl)hexadecanoylaminosulfonyl)butyrylamino)ethoxy)ethoxy)acetic acid and [Arg26]GLP-1-(7-34) peptide (40 mg). 6.5 mg of the title product was obtained.
HPLC (method B4): RT=12.44 min (100%)
LCMS: m/z=1234 ($MH_3^{3+}$). Calculated for ($MH_3^{3+}$): 1234

Example 42

0113-0000-0207; HSt $N^{\epsilon 26}$-({2-[2-(4-(16-(Tetrazol-5-yl)hexadecanoylsulfamoyl)butyrylamino)ethoxy]ethoxy}acetyl)-[(3-(4-imidazolyl)propionyl)7,Arg34]GLP-1 (7-37) peptide (Derivative of SEQ ID NO: 13)

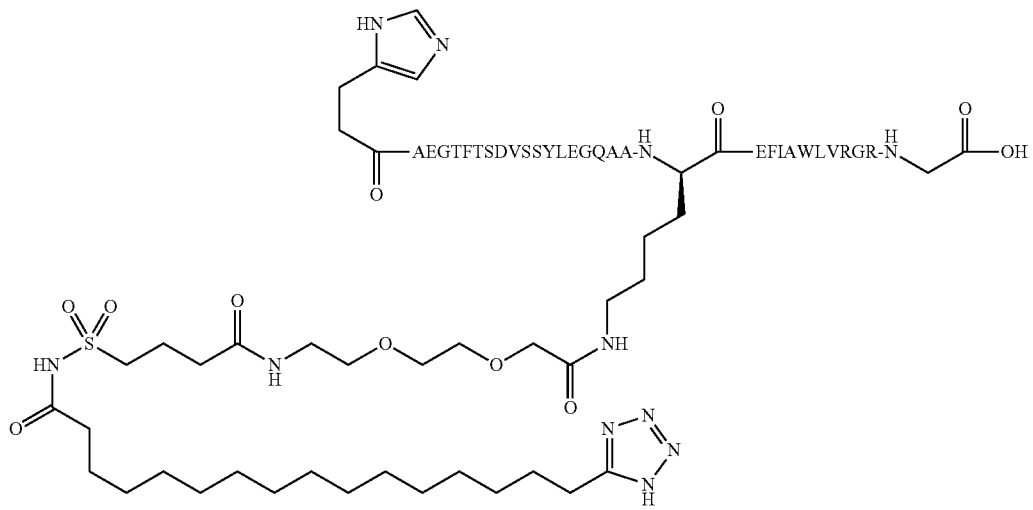

The title compound was prepared as example 6 from (2-(2-(4-16-(5-tetrazolyl)hexadecanoylaminosulfonyl)butyrylamino)ethoxy)ethoxy)acetic acid and [(3-(4-imidazolyl)propionyl)7,Arg34]GLP-1-(7-37) peptide (27 mg). 9.5 mg of the title product was obtained.

HPLC (method B4): RT=11.85 min (96%)
LCMS: m/z=1324 ($MH_3^{3+}$). Calculated for ($MH_3^{3+}$): 1324

Example 43

0113-0000-0214; HSt $N^{\epsilon 26}$-(4-(16-(Tetrazol-5-yl)hexadecanoylsulfamoyl)butyryl)-[Aib8,Arg34]GLP-1-(7-37) peptide (Derivative of SEQ ID NO: 18)

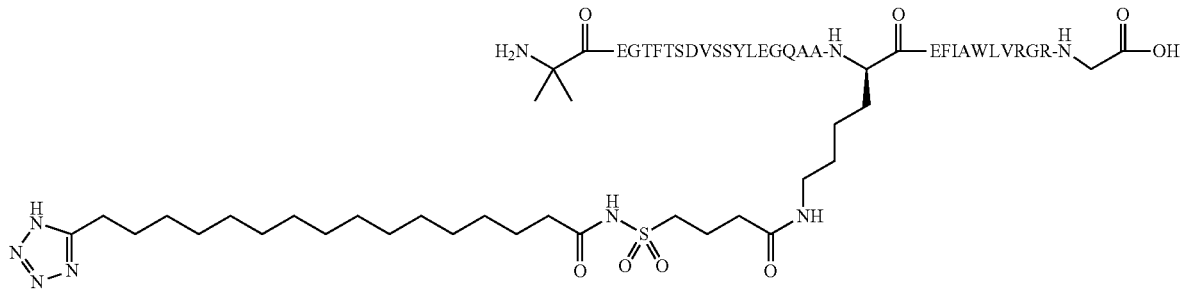

The title compound was prepared as example 6 from (4-(16-(5-tetrazolyl)hexadecanoylaminosulfonyl)butyric acid and [Aib8,Arg34]GLP-1-(7-37) peptide (50 mg). 18.4 mg of the title product was obtained.

HPLC (method B4): RT=11.87 min (95%)
LCMS: m/z=1285 ($MH_3^{3+}$). Calculated for ($MH_3^{3+}$): 1285

Example 44

0113-0000-0223; HSt $N^{\alpha 7}(Me)N^{\epsilon 26}$-(4-(16-(Tetrazol-5-yl)hexadecanoylsulfamoyl)butyryl)-[Arg34]GLP-1-(7-37) peptide (Derivative of SEQ ID NO: 7)

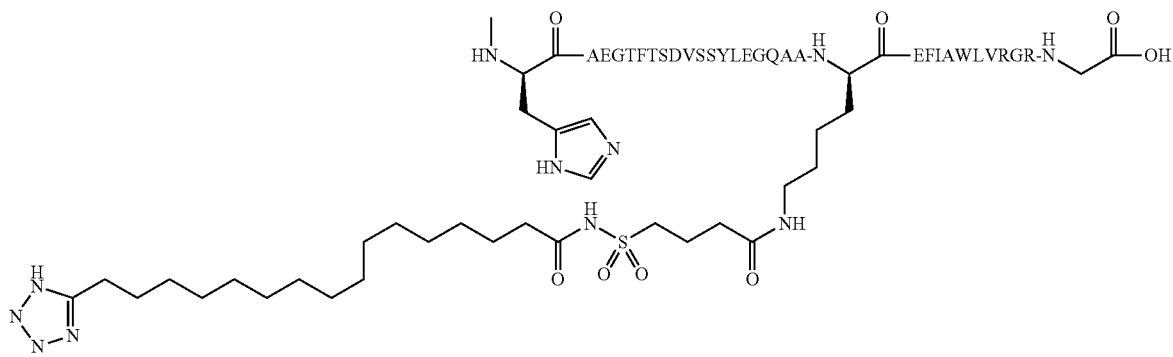

The title compound was prepared as example 6 from (4-(16-(5-tetrazolyl)hexadecanoylaminosulfonyl)butyric acid and $N^{\alpha 7}(Me)$[Arg34]GLP-1-(7-37) peptide (35 mg). 2.5 mg of the title product was obtained.

HPLC (method B4): RT=11.76 min (96%)
LCMS: m/z=1286 ($MH_3^{3+}$). Calculated for ($MH_3^{3+}$): 1285

Example 45

0113-0000-0224; HSt $N^{\epsilon 26}$-(4 (16-(Tetrazol-5-yl)hexadecanoylsulfamoyl) butyryl)-[Gly8,Arg34]GLP-1-(7-37) peptide (Derivative of SEQ ID NO: 19)

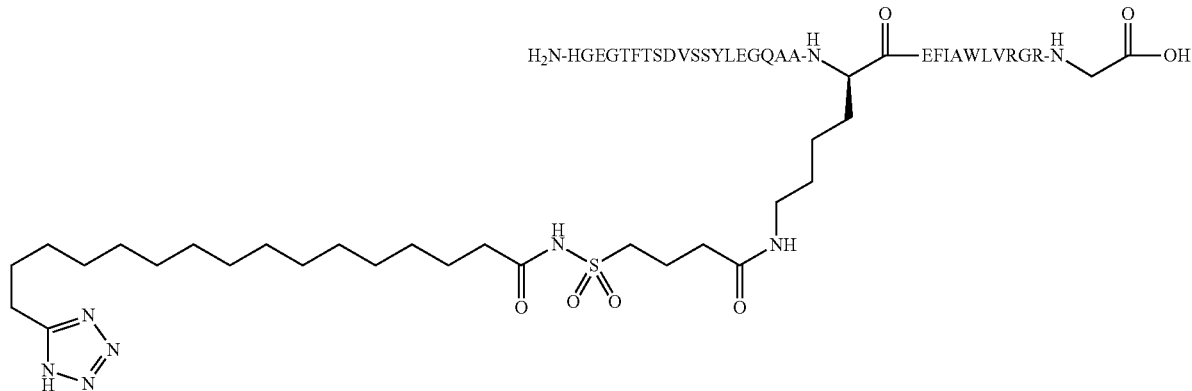

The title compound was prepared as example 6 from (4-(16-(5-tetrazolyl)hexadecanoylaminosulfonyl)butyric acid and [Gly8,Arg34]GLP-1-(7-37) peptide (15 mg). 3.2 mg of the title product was obtained.

HPLC (method B4): RT=11.74 min (95%)

LCMS: m/z=1276 $(MH_3^{3+})$. Calculated for $(MH_3^{3+})$: 1276

Example 46

0113-0000-0244; HSt $N^{\epsilon 14}$-(4 (16-(Tetrazol-5-yl)hexadecanoylsulfamoyl) butyryl)[Lys14;Arg26,34]GLP-1-(7-37) peptide (Derivative of SEQ ID NO: 20)

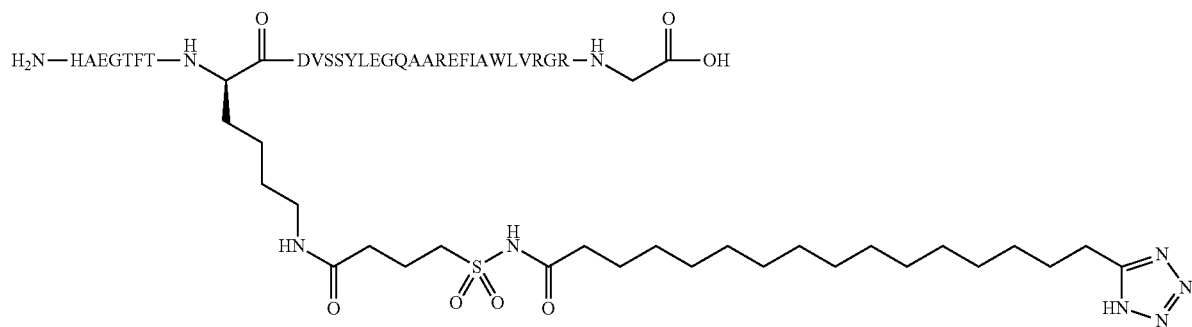

The title compound was prepared as example 6 from 4-(16-(5-tetrazolyl)hexadecanoylaminosulfonyl)butyric acid and [Lys14;Arg26,34]GLP-1-(7-37) peptide (65 mg). 19 mg of the title product was obtained.

HPLC (method B4): RT=11.54 min (98%)

LCMS: m/z=1304 $(MH_3^{3+})$. Calculated for $(MH_3^{3+})$: 1304

Compounds which are planned to be synthesised along the procedures described above are:

Example 47

0113-0000-0277; HSt $N^{\epsilon 18}$-(4-(16-(Tetrazol-5-yl)hexadecanoylsulfamoyl)butyryl)[Lys18;Arg26,34]GLP-1-(7-37) peptide (Derivative of SEQ ID NO: 21)

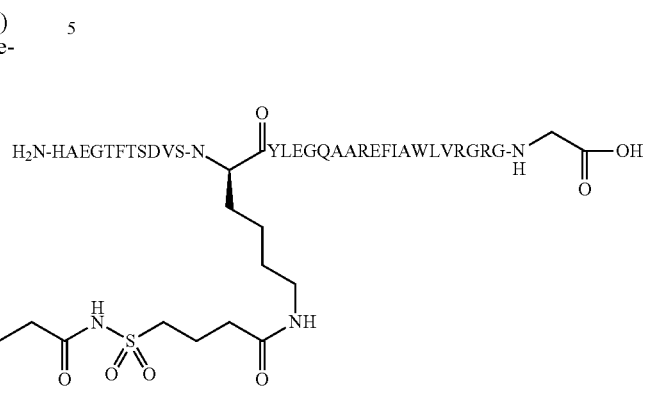

The title compound was prepared as example 6 from 4-(16-(5-tetrazolyl)hexadecanoylaminosulfonyl)butyric acid and [Lys18;Arg26,34]GLP-1-(7-37) peptide (80 mg). 14.5 mg of the title product was obtained.

HPLC (method B4): RT=9.11 min (100%)
LCMS: m/z=1304 (MH$_3^{3+}$). Calculated for (MH$_3^{3+}$): 1304

Example 48

$N^{\epsilon 18}$-(4-(16-(Tetrazol-5-yl)hexadecanoylsulfamoyl)butyryl)[Gly8;Lys18;Arg26,34]GLP-1-(7-37) peptide (Derivative of SEQ ID NO: 22)

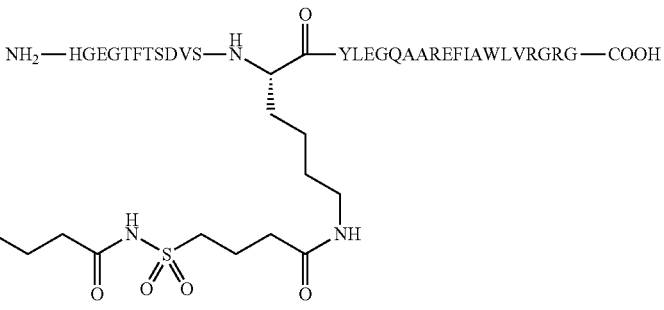

Example 49

$N^{\epsilon 18}$-(4-(16-(Tetrazol-5-yl)hexadecanoylsulfamoyl)butyryl)[Aib8,Lys18;Arg26,34]GLP-1-(7-37) peptide (Derivative of SEQ ID NO: 23)

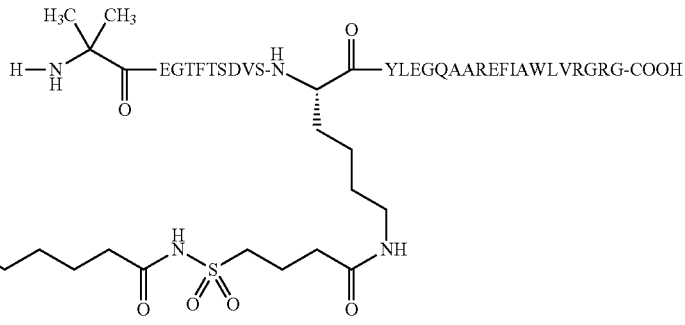

Example 50
$N^{\epsilon 18}$-(4-(16-(Tetrazol-5-yl)hexadecanoylsulfamoyl) butyryl)[3-(4-imidazolyl)propionyl7;Lys18;Arg26, 34]GLP-1-(7-37) peptide (Derivative of SEQ ID NO: 24)
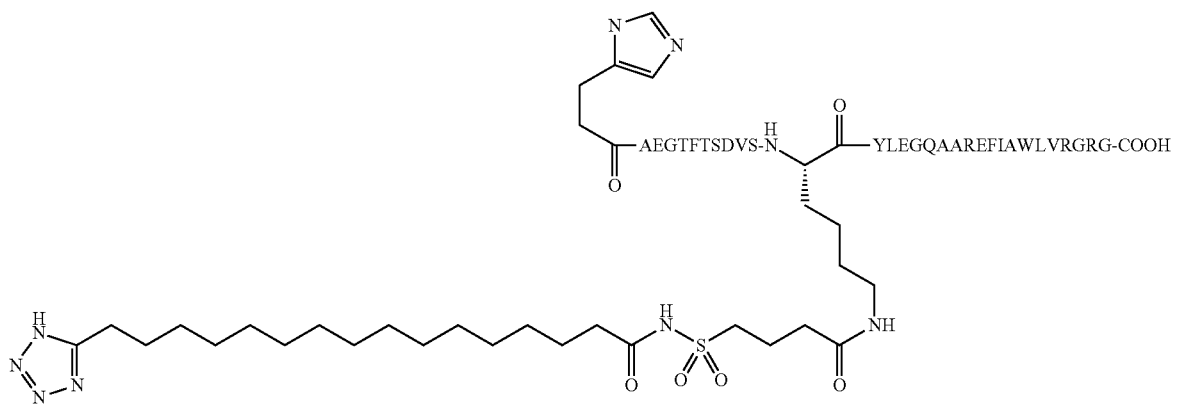
Example 51
$N^{\epsilon 18}$-(4-(16-(Tetrazol-5-yl)hexadecanoylsulfamoyl) butyryl)[Lys18;Arg26]GLP-1-(7-33) peptideamide (Derivative of SEQ ID NO: 25)
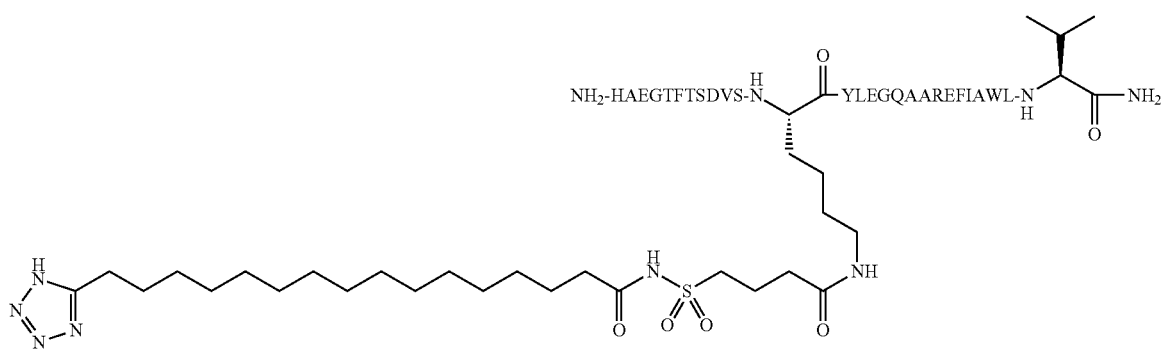

Example 52
0113-0000-xxxx; HSt
N$^{\epsilon 26}$-((2-(2-(2-(2-(2-(4-(16-(Tetrazol-5-yl)hexade-canoylsulfamoyl)butyryl)ethoxy)ethoxy)acety-lamino)ethoxy)ethoxy)acetyl)-[Arg34]GLP-1-(7-37) peptide (Derivative of SEQ ID NO: 7)
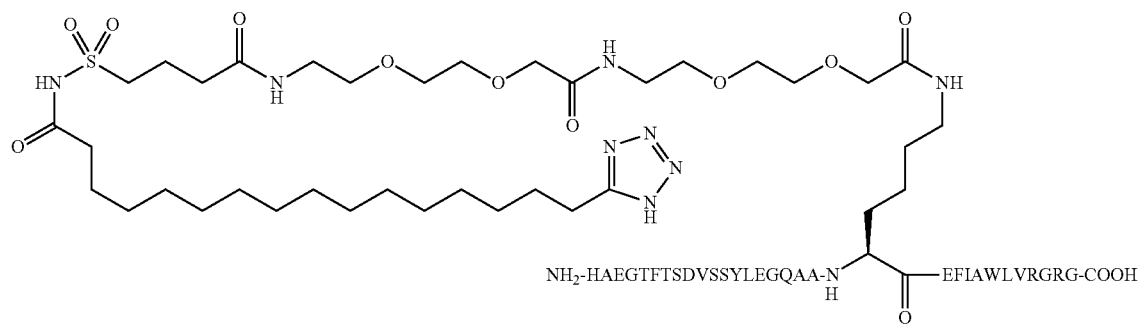
Example 53
0113-0000-xxxx; HSt
N$^{\epsilon 26}$-((2-(2-(2-(2-(2-(4-(16-(Tetrazol-5-yl)hexade-canoylsulfamoyl)butyryl)ethoxy)ethoxy)acety-lamino)ethoxy)ethoxy)acetyl)[Gly8,Arg 34]GLP-1-(7-37) peptide (Derivative of SEQ ID NO: 19)
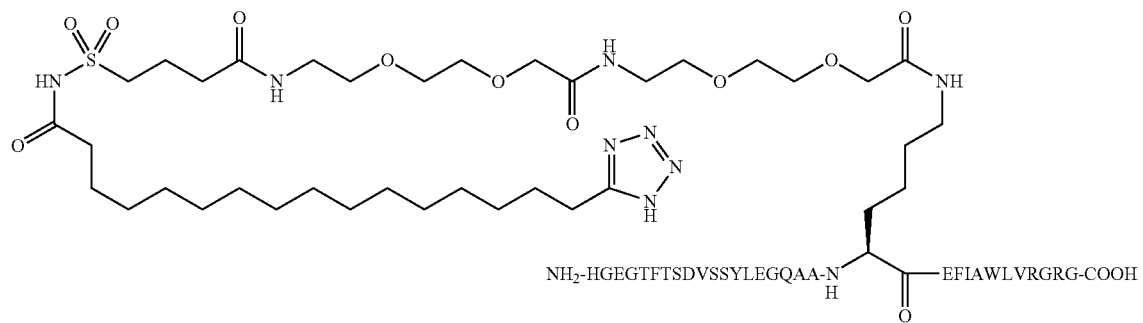

Example 54

0113-0000-xxxx; HSt $N^{\epsilon 26}$-((2-(2-(2-(2-(2-(4-(16-(Tetrazol-5-yl)hexadecanoylsulfamoyl)butyryl)ethoxy)ethoxy)acetylamino)ethoxy)ethoxy)acetyl)-[Aib8,Arg34]GLP-1-(7-37) peptide (Derivative of SEQ ID NO: 18)

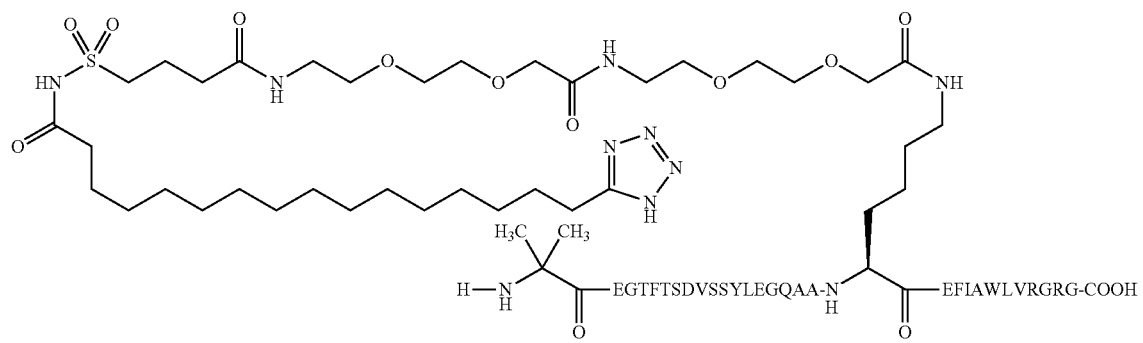

Example 55

$N^{\epsilon 26}$-(4-(16-(4-(4-(5-Tetrazolyl)phenyl)phenyloxy)hexadecanoylamino)-(4S)-4-carboxybutyryl)-[Arg34]GLP-1-(7-37) peptide (Derivative of SEQ ID NO: 7)

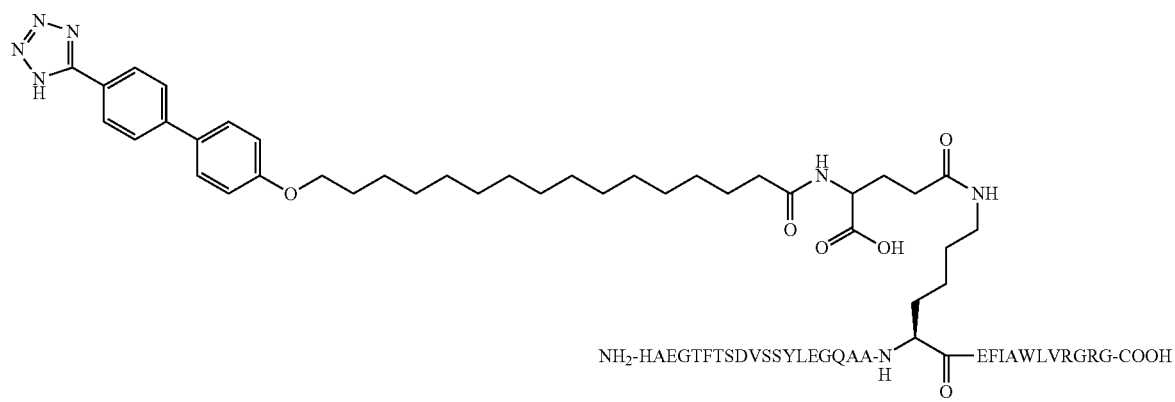

The title compound was prepared as example 6 from 4-(16-(4-(4-(5-tetrazolyl)phenyl)phenyloxy)hexadecanoylamino)-(4S)-4-tert-butoxycarbonylbutyric acid and [Arg34]GLP-1-(7-37) peptide (75 mg). 6.9 mg of the title product was obtained.

HPLC (method B4): RT=10.57 min (100%)
LCMS: m/z=1330 $(MH_3^{3+})$. Calculated for $(MH_3^{3+})$: 1330

Example 56
SEQ ID NO: 19
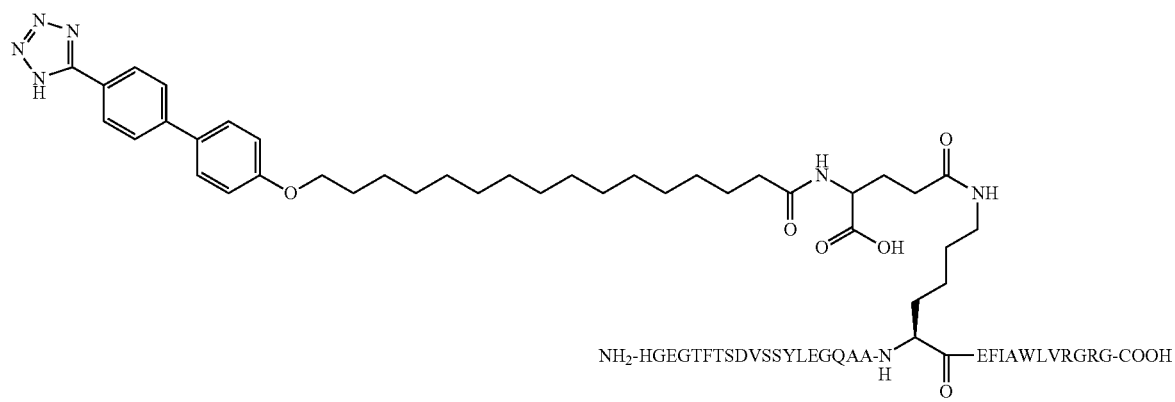
Example 57
SEQ ID NO: 18
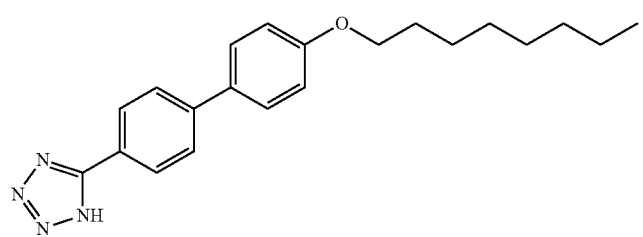
30
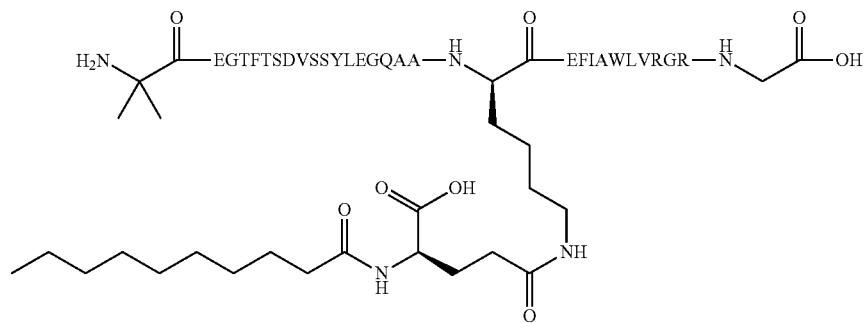

Example 58

N^ε26-(4-{16-[4-(1H-tetrazol-5-yl)phenoxy]hexadecanoylamino}-(4S)-4-carboxybutyryl)-[Arg34] GLP-1-(7-37)-peptide (Derivative of SEQ ID NO: 7)

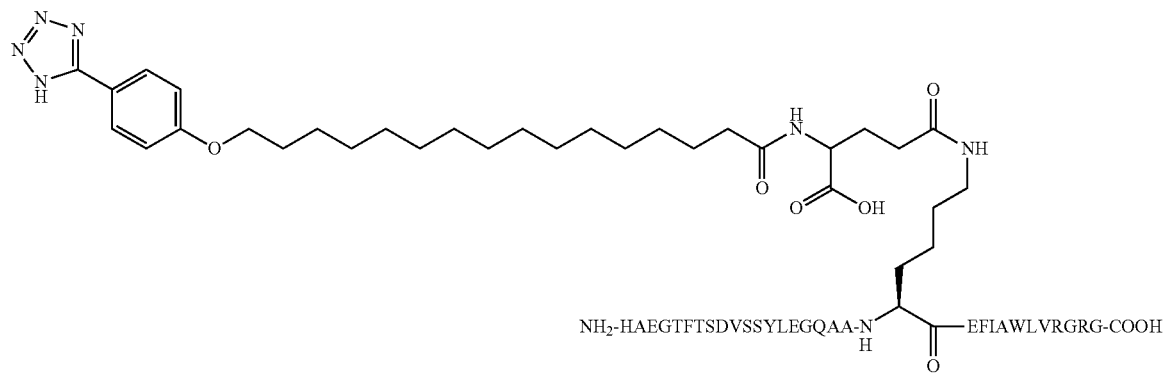

The title compound was prepared as example 6 from (4-{16-[4-(1H-tetrazol-5-yl)phenoxy]hexadecanoylamino}-(4S)-4-tert-butoxycarbonylbutyric acid and [Arg34]GLP-1-(7-37) peptide. 1.6 mg of the title product was obtained.

HPLC (method B4): RT=9.96 min (100%)
LCMS: m/z=1305 (MH$_3^{3+}$). Calculated for (MH$_3^{3+}$): 1305

Example 59

SEQ ID NO: 19

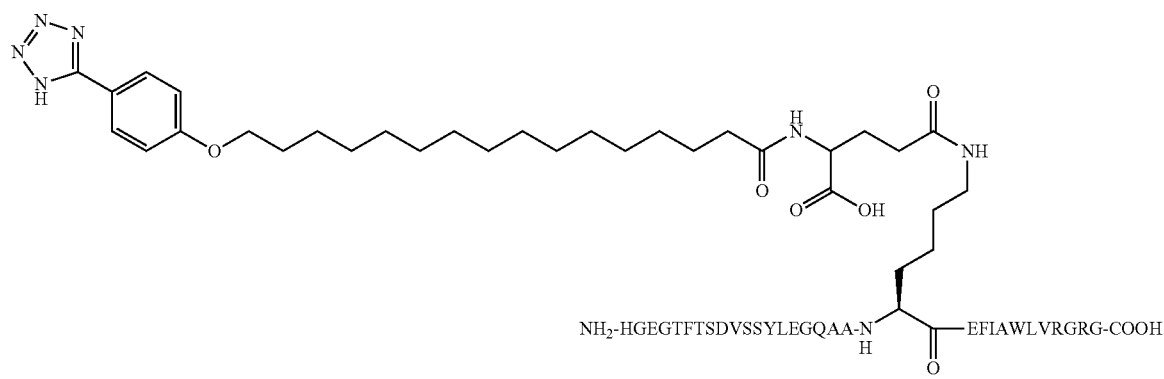

Example 60

SEQ ID NO: 18

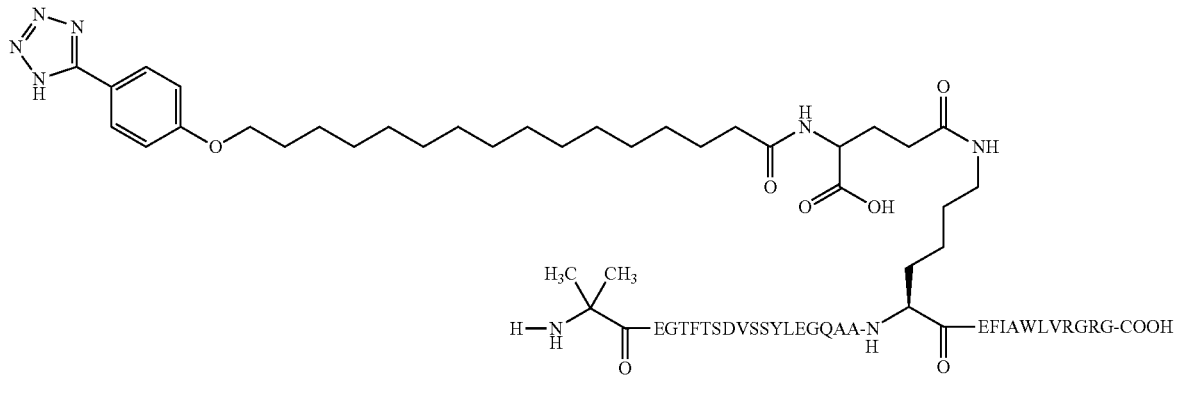

Example 61

N^ε26-{4-[17,17-Bis-(1-H-tetrazol-5-yl)heptade-canoylamino]-(4S)-4-carboxybutyryl}-[Arg34]GLP-1-(7-37)-peptide (Derivative of SEQ ID NO: 7)

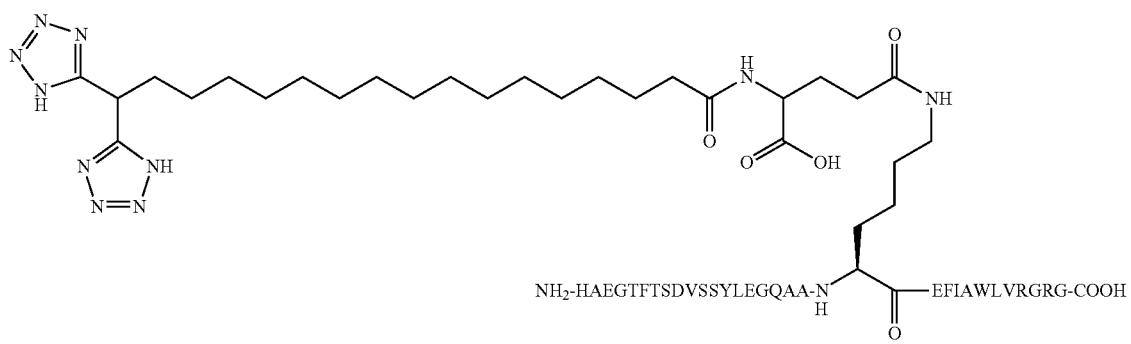

The title compound was prepared as example 6 from {4-[17,17-bis-(1-H-tetrazol-5-yl)heptadecanoylamino]-(4S)-4-tert-butoxycarbonylbutyric acid and [Arg34]GLP-1-(7-37) peptide (150 mg). 7.8 mg of the title product was obtained.
HPLC (method B4): RT=10.25 min (92%)
LCMS: m/z=1301 ($MH_3^{3+}$). Calculated for ($MH_3^{3+}$): 1301

Example 62

SEQ ID NO: 19

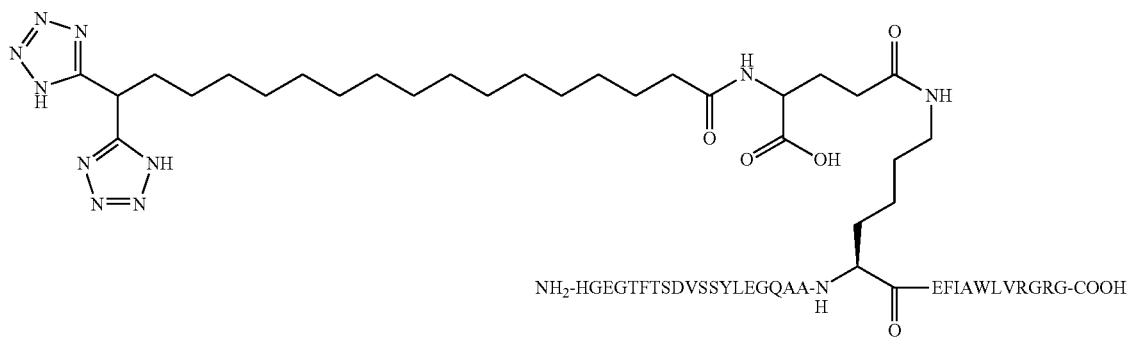

Example 63

SEQ ID NO: 18

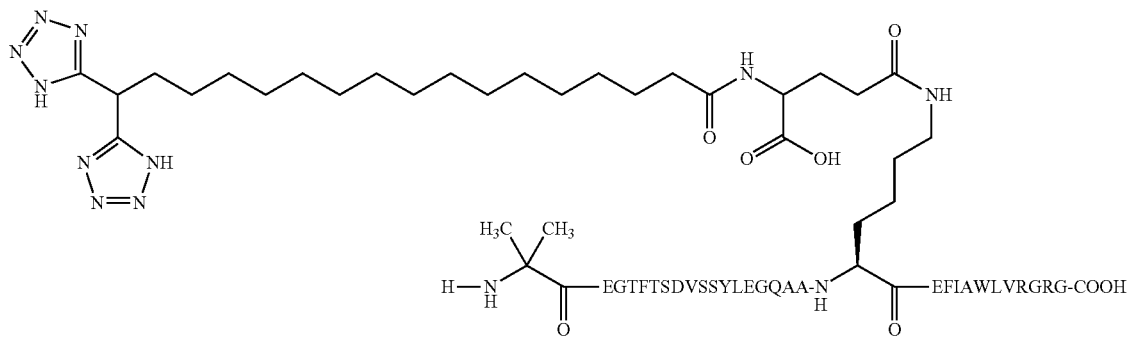

Example 64

N^ε26-(4-{16-[4,5-Bis(1H-tetrazol-5-yl)imidazol-1-yl]hexadecanoylamino}-(4S)-4-carboxybutyryl)-[Arg34] GLP-1 (7-37) (Derivative of SEQ ID NO: 7)

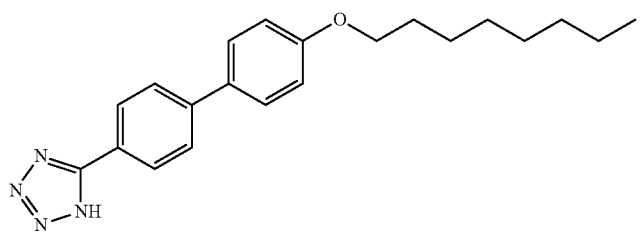

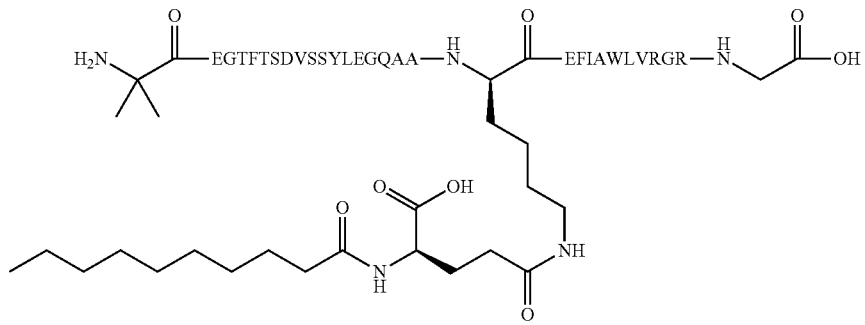

The title compound was prepared as example 6 from (4-{16-[4,5-bis(1H-tetrazol-5-yl)imidazol-1-yl]hexadecanoylamino}-(4S)-4-tert-butoxycarbonylbutyric acid and [Arg34]GLP-1-(7-37) peptide (100 mg). 7.2 mg of the title product was obtained.

HPLC (method B4): RT=13.91 min (97%)

LCMS: m/z=1319 (MH$_3^{3+}$). Calculated for (MH$_3^{3+}$): 1319

Example 65
SEQ ID NO: 19
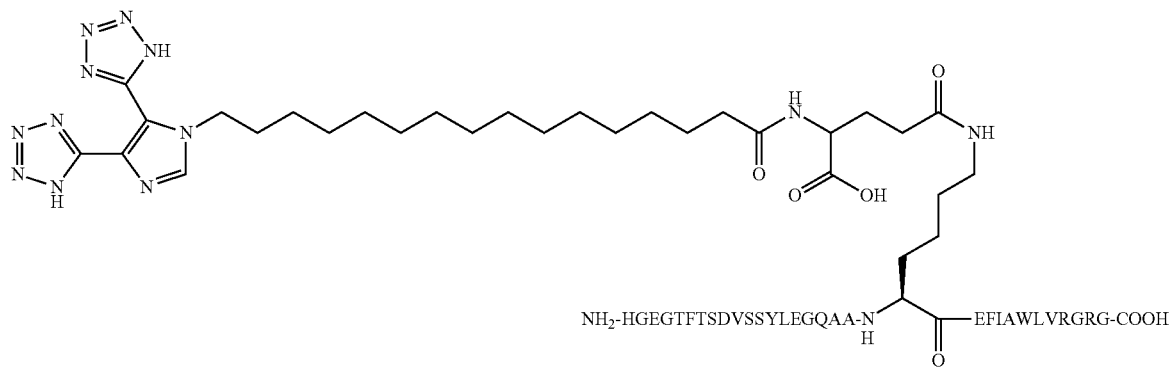
Example 66
SEQ ID NO: 18
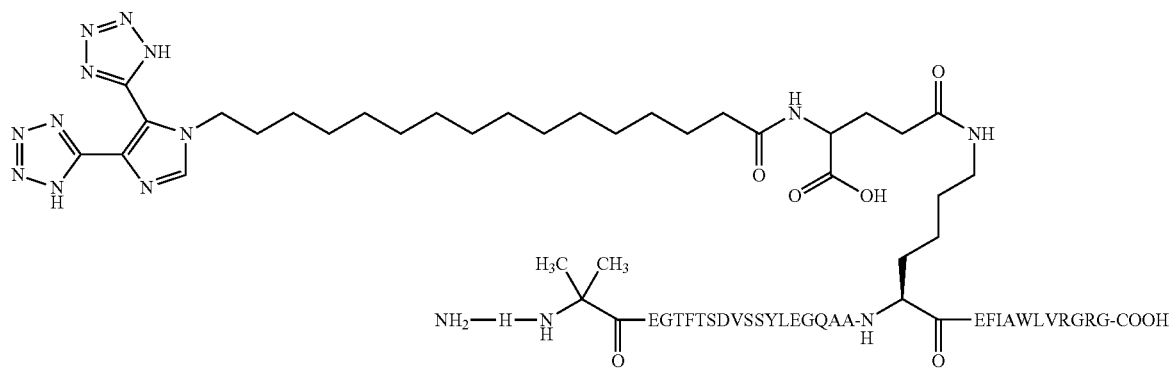
Example 67
SEQ ID NO: 7
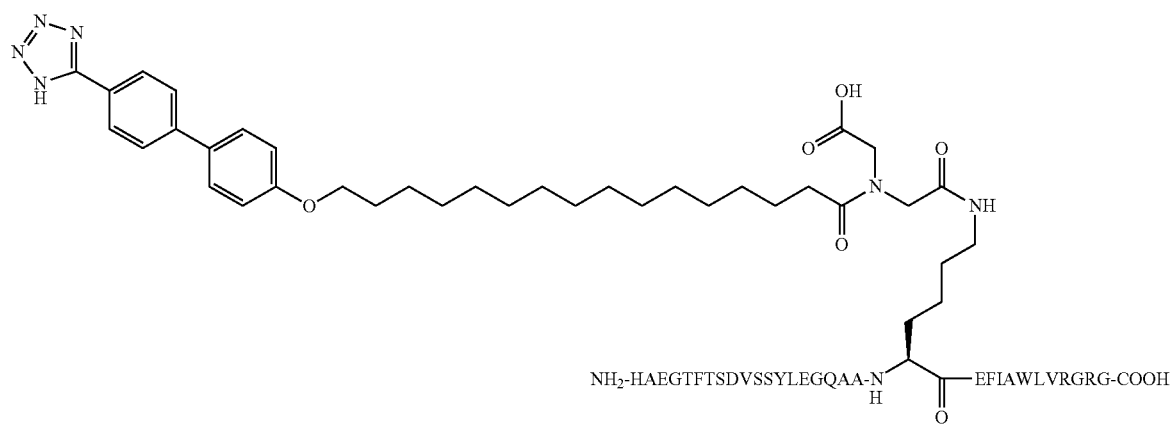

Example 68
SEQ ID NO: 7
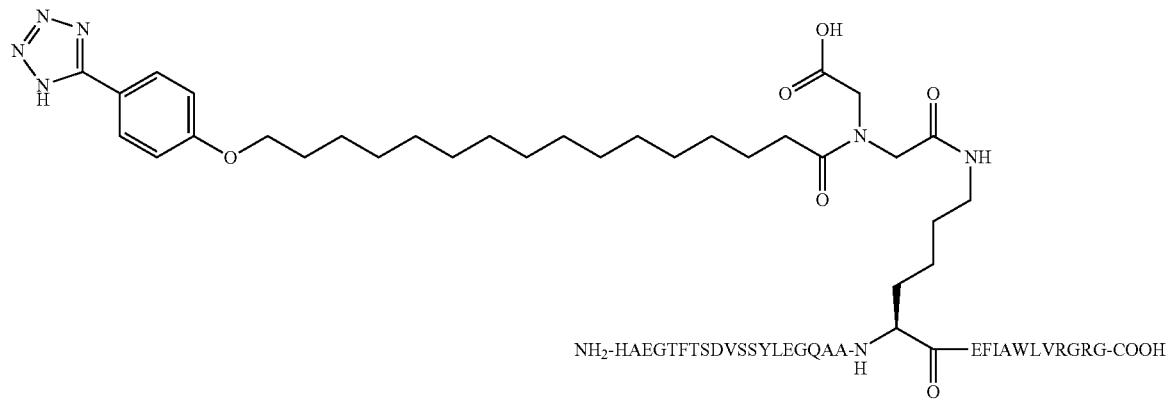
Example 69
SEQ ID NO: 7
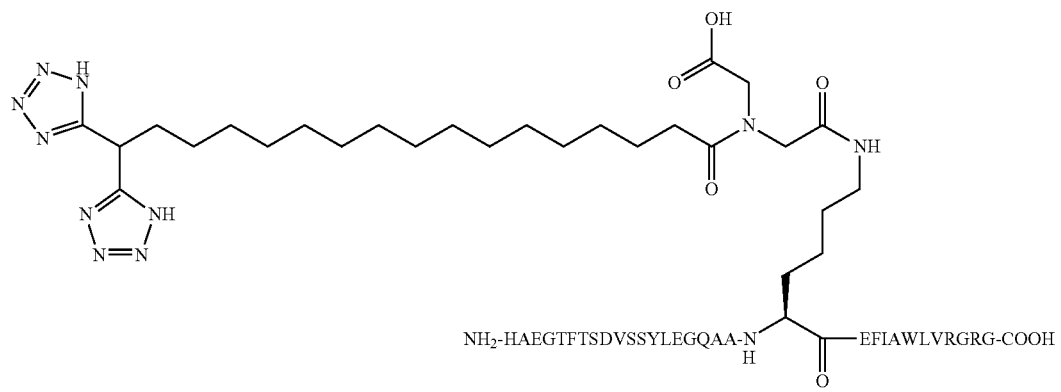
Example 70
SEQ ID NO: 7
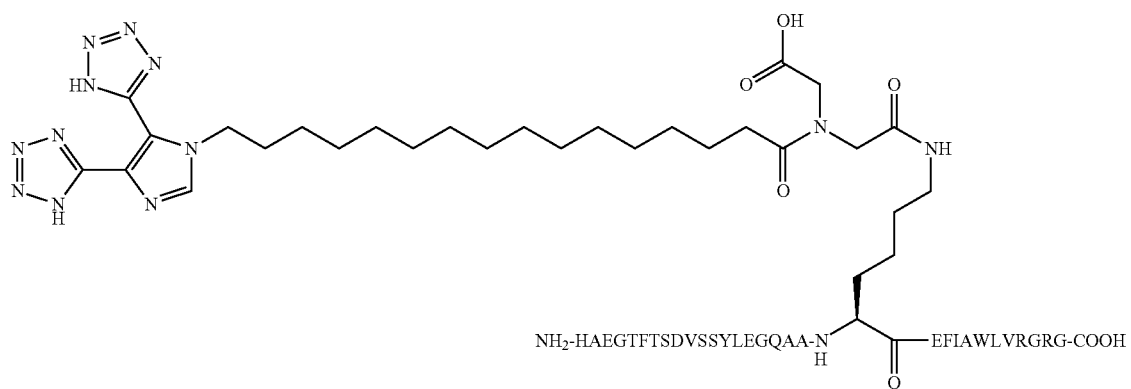

157

Example 71

SEQ ID NO: 7

NH₂-HAEGTFTSDVSSYLEGQAA-N(H)-EFIAWLVRGRG-COOH

Example 72

SEQ ID NO: 19

NH₂-HGEGTFTSDVSSYLEGQAA-N(H)-EFIAWLVRGRG-COOH

Example 73

0113-0000-xxxx; HSt $N^{\epsilon26}$-(4-(19-(Tetrazol-5-yl)nonadecanoylsulfamoyl) butyryl)[Arg34]GLP-1-(7-37) peptide (Derivative of SEQ ID NO: 7)

NH₂-HAEGTFTSDVSSYLEGQAA-N(H)-EFIAWLVRGRG-COOH

158

Example 74

SEQ ID NO: 19

NH₂-HGEGTFTSDVSSYLEGQAA-N(H)-EFIAWLVRGRG-COOH

Example 75

SEQ ID NO: 18

H-N(H)-EGTFTSDVSSYLEGQAA-N(H)-EFIAWLVRGRG-COOH

Example 76

$N^{\epsilon26}$-(6-{16-[1H-Tetrazol-5-yl]hexadecanoyl}sulfamoylhexanoyl)[Arg34]GLP-1-(7-37) (Derivative of SEQ ID NO: 7)

NH₂-HAEGTFTSDVSSYLEGQAA-N(H)-EFIAWLVRGRG-COOH

The title compound was prepared as example 6 from (6-{16-[1H-tetrazol-5-yl]hexadecanoyl}sulfamoylhexanoic acid and [Arg34]GLP-1-(7-37) peptide. 67.5 mg of the title product was obtained.

HPLC (method B4): RT=11.08 min (98%)

159
LCMS: m/z=1290 (MH$_3^{3+}$). Calculated for (MH$_3^{3+}$): 1290
Example 77
SEQ ID NO: 19
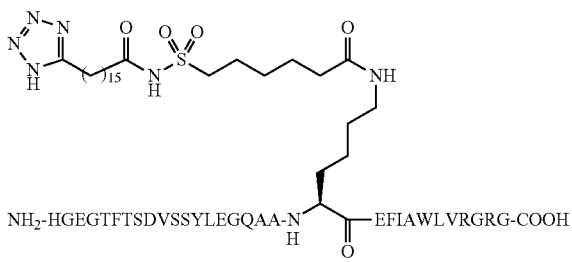
Example 78
SEQ ID NO: 18
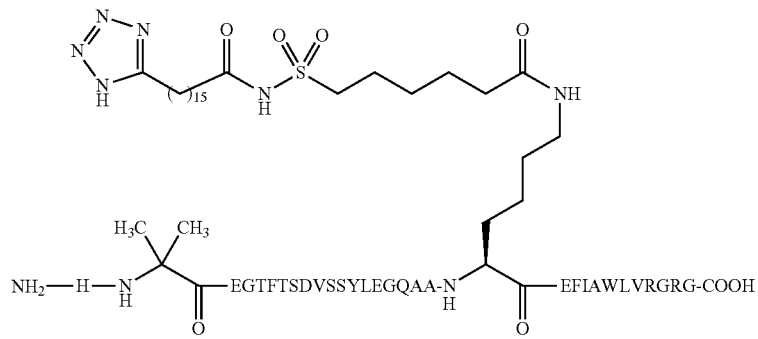
Example 79
SEQ ID NO: 7
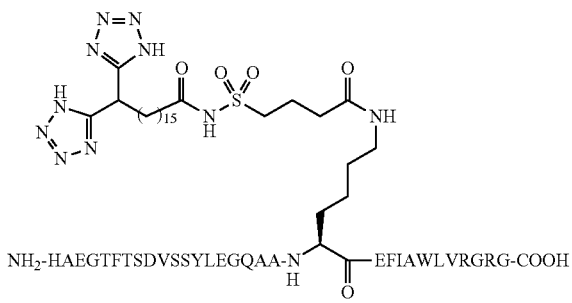
160
Example 80
SEQ ID NO: 19
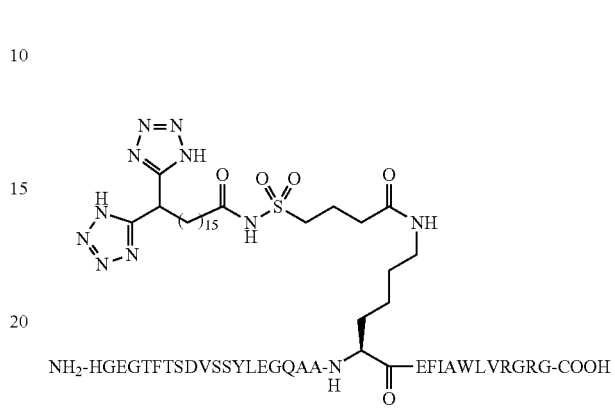
Example 81
SEQ ID NO: 7
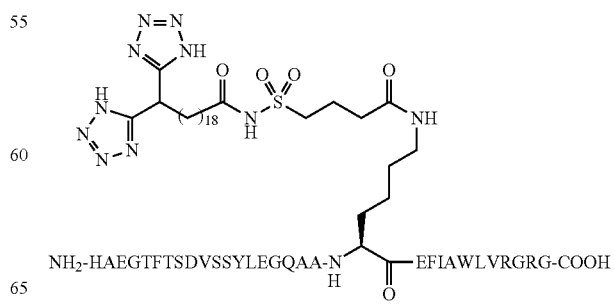

Example 82
SEQ ID NO: 7
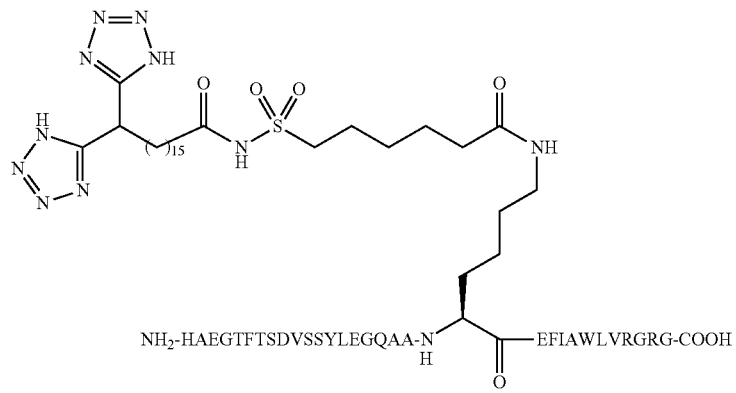
Example 83
SEQ ID NO: 19
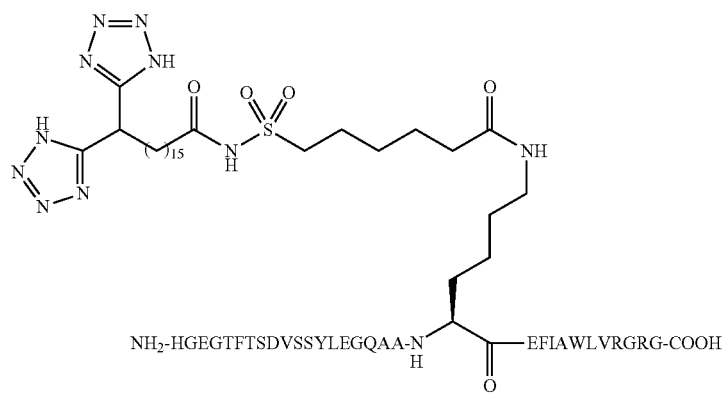
Example 84
SEQ ID NO: 7
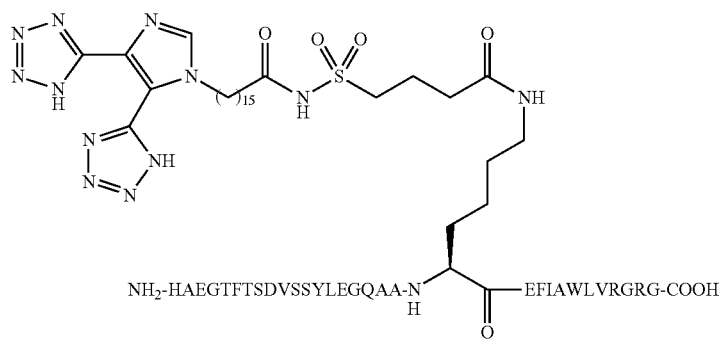

Example 85
SEQ ID NO: 19
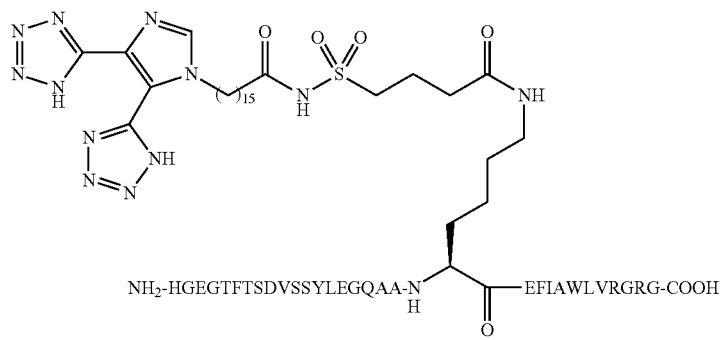
Example 86
SEQ ID NO: 7
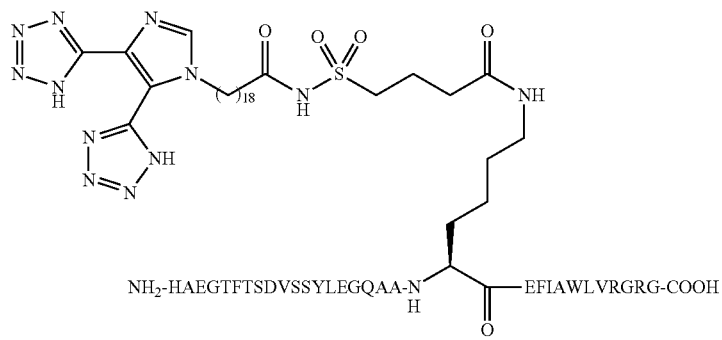
Example 87
SEQ ID NO: 7
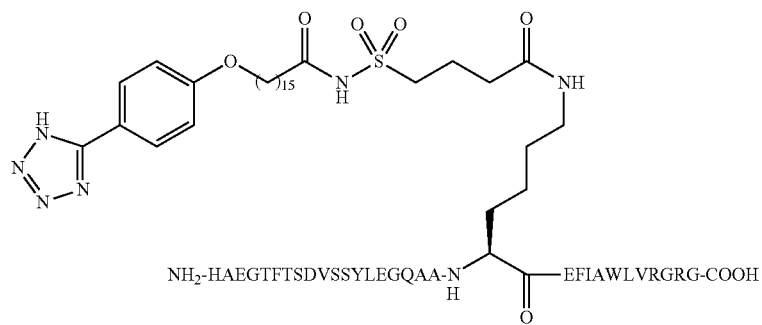

Example 88
SEQ ID NO: 7
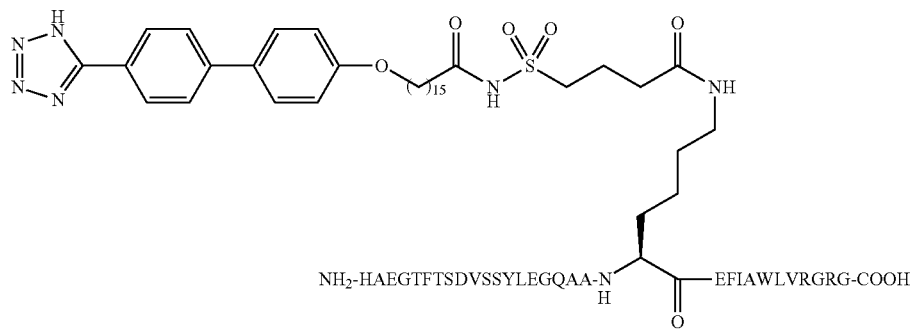
Example 89
SEQ ID NO: 7
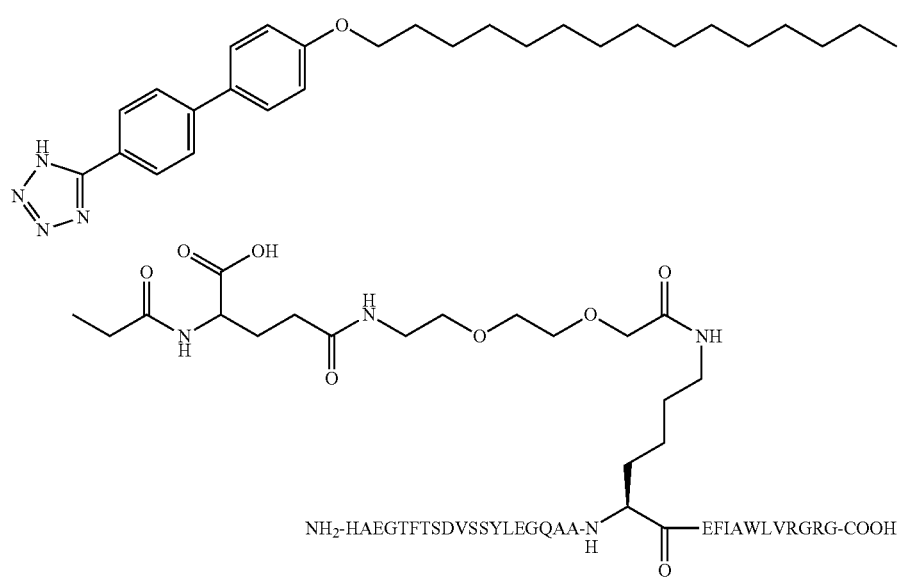
Example 90
SEQ ID NO: 7
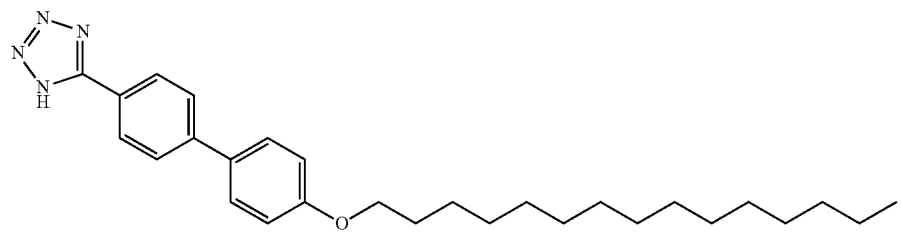

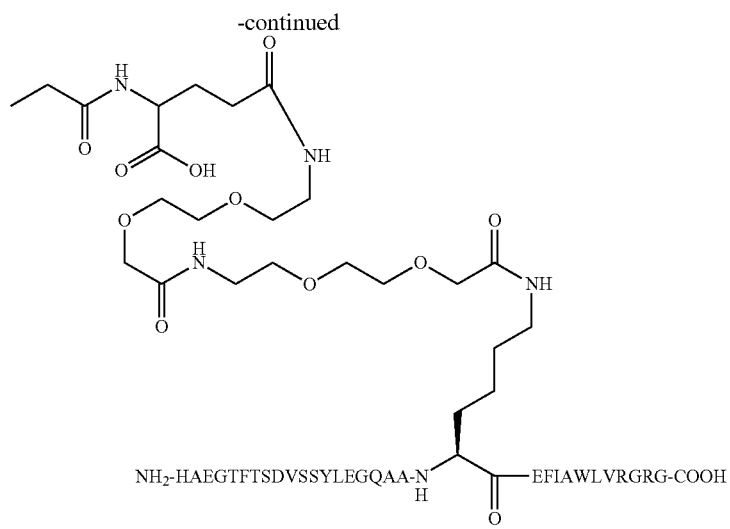
Example 91
SEQ ID NO: 18
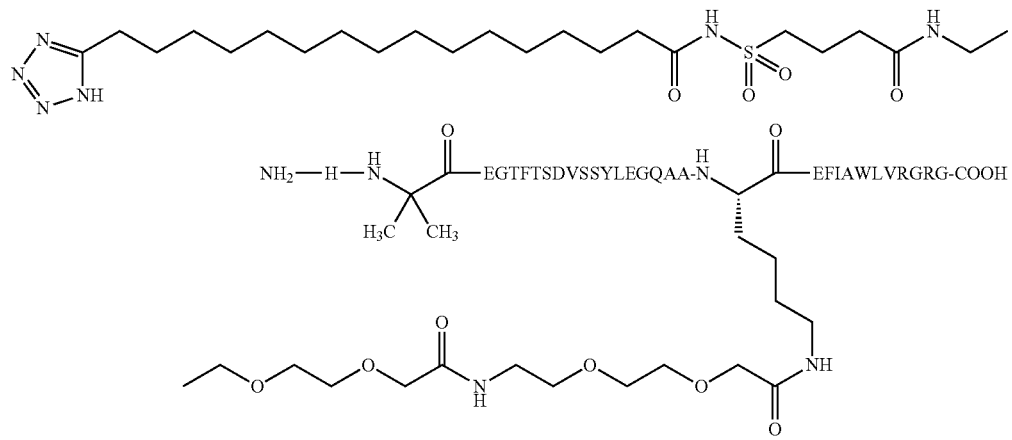
Example 92
SEQ ID NO: 18
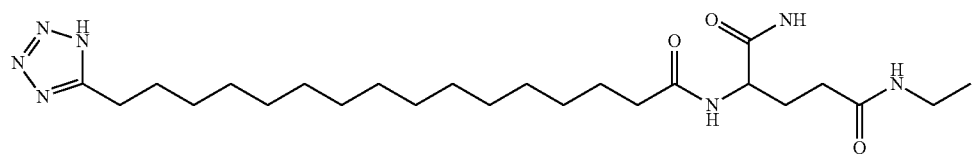

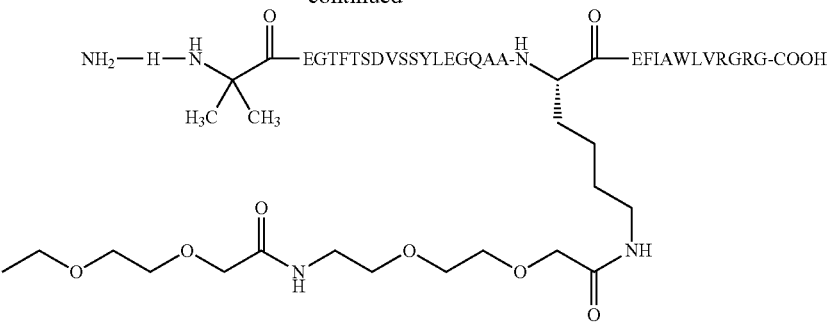
Example 93
SEQ ID NO: 18
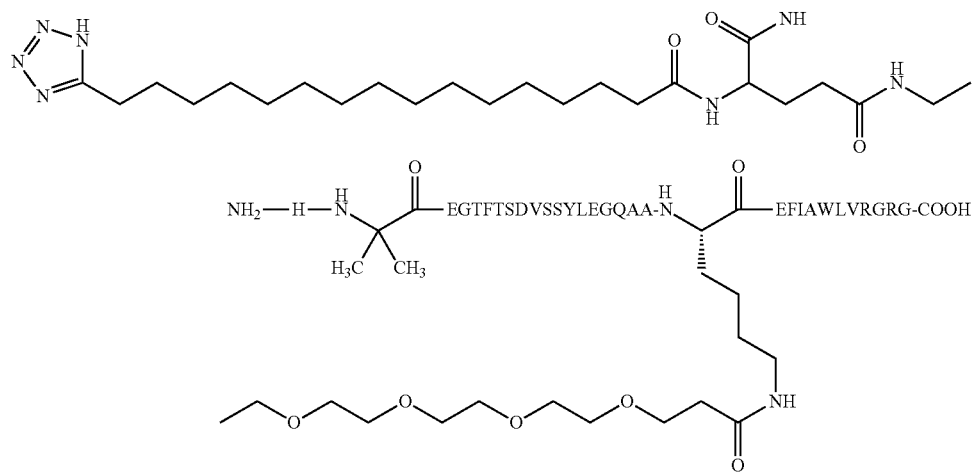
Example 94
SEQ ID NO: 18
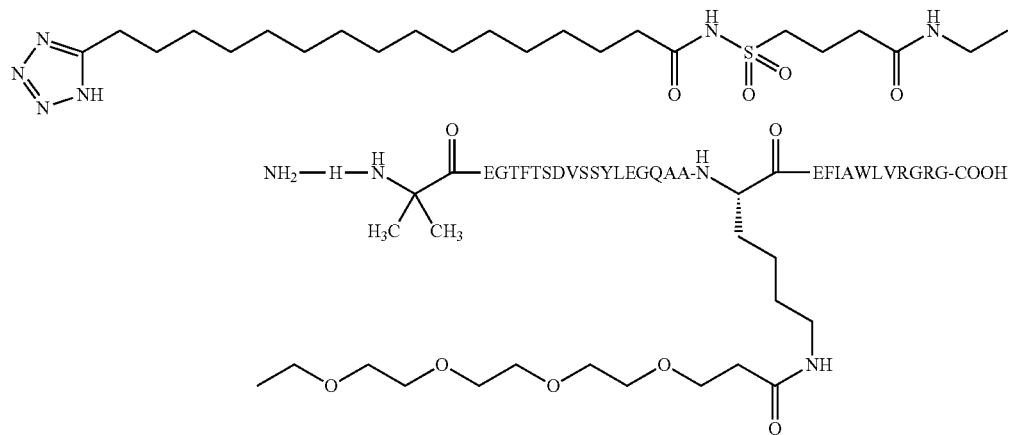

Example 95

N$^{\epsilon 18}$-(6-{16-[1H-Tetrazol-5-yl]hexadecanoylsulfamoyl}hexanoyl)[Arg26,34, Lys18] GLP-1-(7-37)-peptide (Derivative of SEQ ID NO: 21)

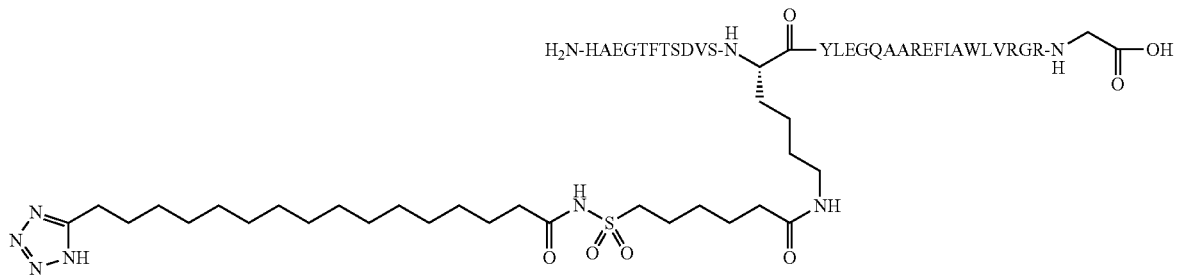

The title compound was prepared as example 6 from 18-(6-{16-[1H-tetrazol-5-yl]hexadecanoylsulfamoyl}hexanoic acid and [Arg26,34, Lys18]GLP-1-(7-37)-peptide. 26.3 mg of the title product was obtained.

HPLC (method B4): RT=10.83 min (98.3%)
LCMS: m/z=1313 (MH$_3^{3+}$). Calculated for (MH$_3^{3+}$): 1313

According to the procedures above the following compounds were prepared:

N$^{\epsilon 26}$-[4(S)-4-(16-{4-[4-(1-H-tetrazol-5-yl)phenyl]phenoxy}hexadecanoylamino)-4-carboxybutyryl][Aib8, Arg34] GLP-1(7-37) (Derivative of SEQ ID NO: 18)

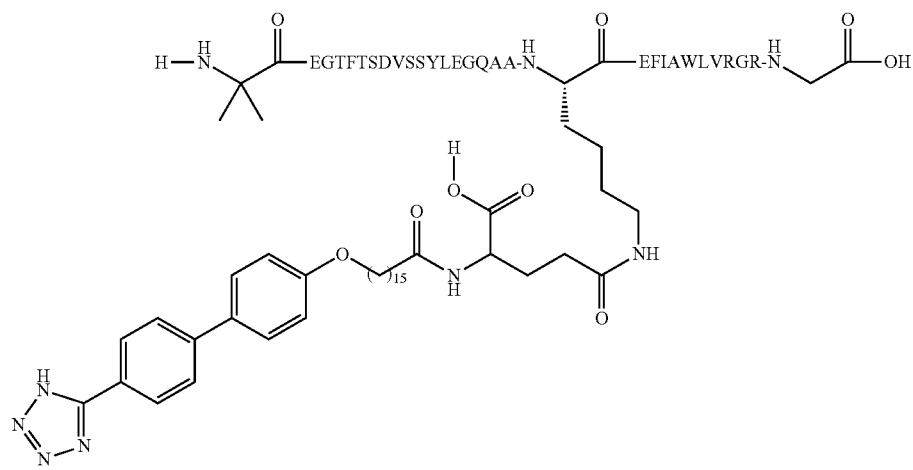

N$^{\epsilon 26}$-[4(S)-4-(19-(1-H-tetrazol-5-yl)nonadecanoylamino)-4-carboxybutyryl][Aib8,Arg34] GLP-1(7-37) (Derivative of SEQ ID NO: 18)

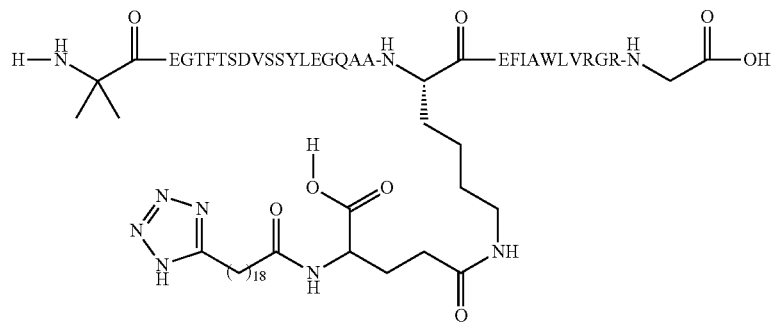

$N^{\epsilon 26}$-[4(S)-4-(2-(2-(2-(4-(N-(16-(1-H-tetrazol-5-yl)hexadecanoyl)sulfamoyl)butyrylamino)ethoxy)ethoxy)acetylamino)-4-carboxybutyryl][Aib8,Arg34] GLP-1(7-37) (Derivative of SEQ ID NO: 18)

or $N^{\epsilon 26}$-[4(S)-4-(2-(2-(2-(6-(N-(16-(1-H-tetrazol-5-yl)hexadecanoyl)sulfamoyl)hexanoylamino)ethoxy)ethoxy)acetylamino)-4-carboxybutyryl][Aib8,Arg34] GLP-1(7-37) (Derivative of SEQ ID NO: 18)

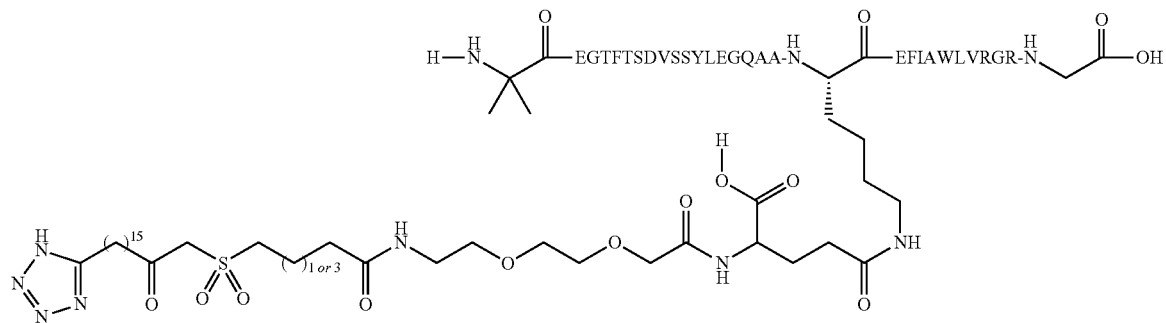

$N^{\epsilon 26}$-[4(S)-4-(2-(2-(2-(2-(2-(2-(4-(N-(16-(1-H-tetrazol-5-yl)hexadecanoyl)sulfamoyl)butyrylamino)ethoxy)ethoxy)acetylamino)ethoxy)ethoxy)acetylamino)-4-carboxybutyryl][Aib8,Arg34] GLP-1(7-37) (Derivative of SEQ ID NO: 18)

or $N^{\epsilon 26}$-[4(S)-4-(2-(2-(2-(2-(2-(2-(6-(N-(16-(1-H-tetrazol-5-yl)hexadecanoyl)sulfamoyl)hexanoylamino)ethoxy)ethoxy)acetylamino)ethoxy)ethoxy)acetylamino)-4-carboxybutyryl][Aib8,Arg34] GLP-1(7-37) (Derivative of SEQ ID NO: 18)

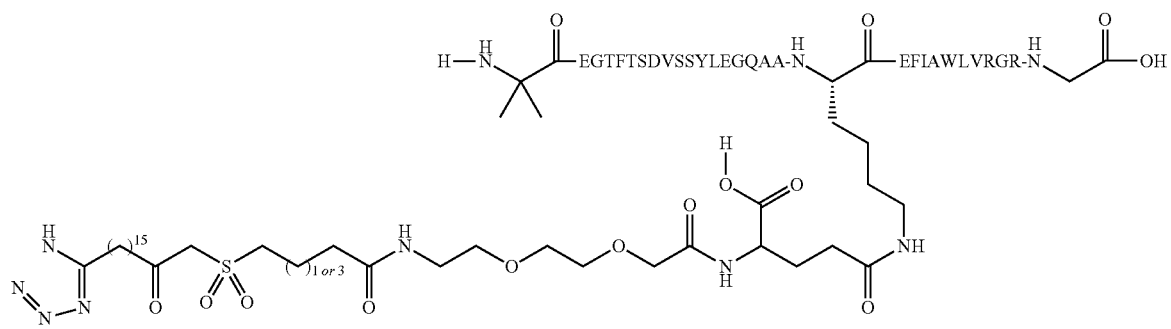

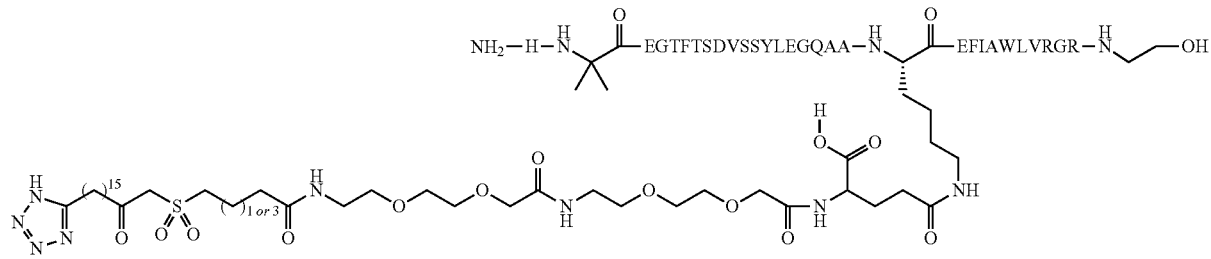

N$^{\epsilon 18}$-6-(16-[1-H-tetrazol-5-yl]hexadecanoylsulfamoyl)hexanoyl [Aib8,Arg26,34] GLP-1(7-37) (Derivative of SEQ ID NO: 23)

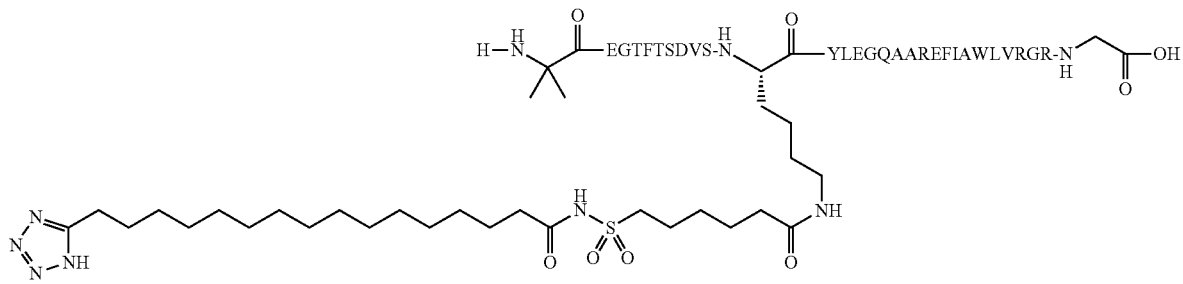

N$^{\epsilon 18}$-[4(S)-4-(16-{-4-[4-(1-H-tetrazol-5-yl)phenyl]phenoxy}hexadecanoylamino)-4-carboxybutyryl][Aib8, Arg26,34] GLP-1(7-37) (Derivative of SEQ ID NO: 23)

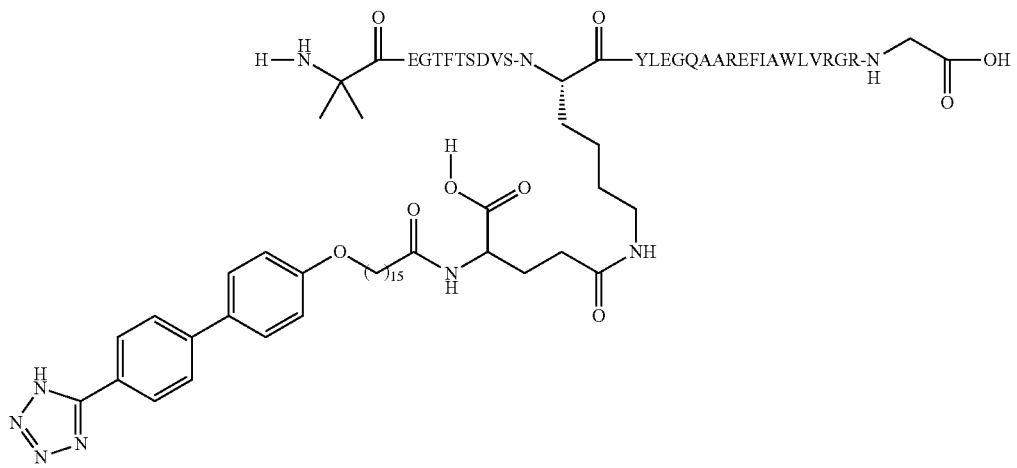

The invention claimed is:

1. A method for increasing the plasma half-life of a molecule, said method comprising converting said molecule into a compound of general formula (I):

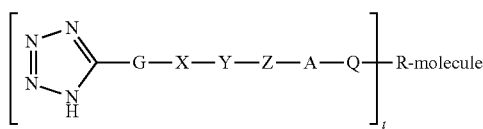

wherein

G, X, and Y independently represent
a bond, —S—, —O—, —NH—, —(CH$_2$)$_{1-15}$—, —C(O)NH—, or
arylene, optionally substituted with one or more alkyl, amino, cycloalkyl, aryl, heteroaryl, halogen, nitro, lower alkoxy, hydroxy, MeCONH—, alkanoyl, or cyano, or
heteroarylene, optionally substituted with one or more alkyl, amino, cycloalkyl, aryl, heteroaryl, halogen, nitro, lower alkoxy, hydroxy, MeCONH—, alkanoyl, or cyano, and Z represents a bond or
—(CH$_2$)$_n$—, —O—(CH$_2$)$_n$—, —S—(CH$_2$)$_n$—, —(OCH$_2$CH$_2$)$_n$—, —(CF$_2$)$_n$—, —O—CH$_2$—(CF$_2$)$_n$—, or —S—CH$_2$—(CF$_2$)$_n$—,
wherein n is 1-40, and A represents
—C(=O)—, —O—C(=O)—, —NH—C(=O)—, —C(C=O)NH—S(=O)$_2$—, —S(=O)$_2$NH—C(=O)—, —(CH$_2$)$_{1-5}$—, —O—(CH$_2$)$_{1-5}$—, or —O—(CH$_2$)$_{1-5}$—C(=O)—, and Q represents a bond or
—[NH—(CH$_2$CH$_2$O)$_m$—(CH$_2$)$_p$-E-C(=O)]$_q$—, or
—O—(CH$_2$CH$_2$O)$_m$—(CH$_2$)$_p$-E-C(=O)—, or
—S—(CH$_2$CH$_2$O)$_m$—(CH$_2$)$_p$-E-C(=O)—, wherein E is a bond, O, S, or NH, and m, p, and q independently are 1-40, and R represents a bond or [—NH(CH$_2$)$_4$CH(NH—)—C(=O)—]$_{1-5}$, and t is 1-40, and the term 'molecule' refers to a compound comprising an amino group or a mercapto group, to which the group A or Q may be covalently linked, wherein the molecule is a therapeutic agent, wherein the therapeutic agent is a polypeptide, and wherein the therapeutic agent is human growth hormone or an analog thereof.

2. A compound of general formula (I):

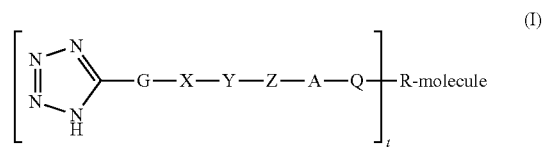

wherein

G, X, and Y independently represent
a bond, —S—, —O—, —NH—, —(CH$_2$)$_{1-10}$—, or
arylene, optionally substituted with one or more alkyl, amino, cycloalkyl, aryl, heteroaryl, halogen, nitro, lower alkoxy, hydroxy, MeCONH—, alkanoyl, or cyano, or
heteroarylene, optionally substituted with one or more alkyl, amino, cycloalkyl, aryl, heteroaryl, halogen, nitro, lower alkoxy, hydroxy, MeCONH—, alkanoyl, or cyano, and Z represents a bond or
—(CH$_2$)$_n$—, —O—(CH$_2$)$_n$—, —S—(CH$_2$)$_n$—, —(OCH$_2$CH$_2$)$_n$—, —(CF$_2$)$_n$—, —O—CH$_2$—(CF$_2$)$_n$—, or —S—CH$_2$—(CF$_2$)$_n$—,
wherein n is 1-40, and A represents
—C(=O)—, —O—C(=O)—, —NH—C(=O)—, —C(C=O)NH—S(=O)$_2$—, —S(=O)$_2$NH—C(=O)—, —(CH$_2$)$_{1-5}$—, —O—(CH$_2$)$_{1-5}$—, or —O—(CH$_2$)$_{1-5}$—C(=O)—, and Q represents a bond or
—[NH—(CH$_2$CH$_2$O)$_m$—(CH$_2$)$_p$-E-C(=O)]$_q$—, or
—O—(CH$_2$CH$_2$O)$_m$—(CH$_2$)$_p$-E-C(=O)—, or
—S—(CH$_2$CH$_2$O)$_m$—(CH$_2$)$_p$-E-C(=O)—, wherein E is a bond, O, S, or NH, and m, p, and q independently are 1-40, and R represents a bond or [—NH(CH$_2$)$_4$CH(NH—)—C(=O)—]$_{1-5}$, and t is 1-40, and the term 'molecule' refers to a compound comprising an amino group or a mercapto group, to which the group A or Q may be covalently linked, wherein the molecule is a therapeutic agent, wherein the therapeutic agent is a polypeptide, and wherein the therapeutic agent is human growth hormone or an analog thereof.

3. A compound according to claim 2, wherein G, X and Y are all a bond.

4. A compound according to claim 2, wherein G, X and Y are all selected from —(CH$_2$)$_{1-10}$—.

5. A compound according to claim 2, wherein t is 1.

6. A compound according to claim 5, wherein

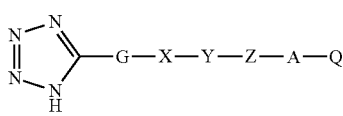

is 16-(5-tetrazolyl)hexadecanoyl,
4-[N-(16-{5-tetrazolyl}hexadecanoyl)sulfamoyl]butyryl,
2-(2-(2-(16-(tetrazol-5-yl)(hexadecanoylamino)ethoxy)ethoxy)acetyl) or
16-(1H-tetrazol-5-yl)hexadecanoic acid [2-(2-{[2-(2-carbamoylmethoxyethoxy)ethylcarbamoyl]methoxy}ethoxy)ethyl]amide.

7. A compound according to claim 2, wherein the molecule is covalently linked to R via the ε-amino group of a lysine residue of the molecule.

8. A compound according to claim 2, wherein the molecule is covalently linked to R via the thiol group of a cysteine residue of the molecule.

9. A compound of general formula (II)

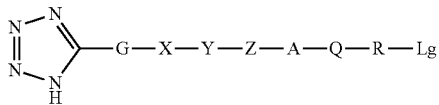

(II)

wherein,

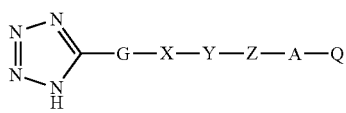

is 16-(5-tetrazolyl)hexadecanoyl,
4-[N-(16-{5-tetrazolyl}hexadecanoyl)sulfamoyl]butyryl,
2-(2-(2-(16-(tetrazol-5-yl)(hexadecanoylamino)ethoxy)ethoxy)acetyl) or
16-(1H-tetrazol-5-yl)hexadecanoic acid [2-(2-{[2-(2-carbamoylmethoxyethoxy)ethylcarbamoyl]methoxy}ethoxy)ethyl]amide;

R is a bond or [—NH(CH$_2$)$_4$CH(NH—)—C(=O)—]$_{1-5}$, and

Lg is a leaving group selected from the group consisting of Cl, Br, I, OH, —OSO$_2$Me, —OSO$_2$CF$_3$, —OTs, —SMe$_2^+$, —OSu, —OBt, —OAt, —OPh, and —O(4-NO$_2$)Ph.

10. A pharmaceutical composition comprising a compound according to claim 2, and a pharmaceutically acceptable excipient.

11. The pharmaceutical composition according to claim 10, which is suited for parenteral administration.

\* \* \* \* \*